US010767219B2

(12) United States Patent
Sabounchi et al.

(10) Patent No.: US 10,767,219 B2
(45) Date of Patent: Sep. 8, 2020

(54) DISPOSABLE, INTEGRATED MICROFLUIDIC CARTRIDGE AND METHODS OF MAKING AND USING SAME

(71) Applicant: Illumina, Inc., San Diego, CA (US)

(72) Inventors: Poorya Sabounchi, Atherton, CA (US); Behnam Javanmardi, Saratoga, CA (US); Tarun Khurana, Fremont, CA (US); Philip Paik, Chula Vista, CA (US); Yan-You Lin, Fremont, CA (US)

(73) Assignee: ILLUMINA, INC., San Diego, CA (US)

( * ) Notice: Subject to any disclaimer, the term of this patent is extended or adjusted under 35 U.S.C. 154(b) by 193 days.

(21) Appl. No.: 15/125,124

(22) PCT Filed: Mar. 11, 2015

(86) PCT No.: PCT/US2015/020029
§ 371 (c)(1),
(2) Date: Sep. 9, 2016

(87) PCT Pub. No.: WO2015/138648
PCT Pub. Date: Sep. 17, 2015

(65) Prior Publication Data
US 2017/0016060 A1   Jan. 19, 2017

Related U.S. Application Data

(60) Provisional application No. 61/987,699, filed on May 2, 2014, provisional application No. 61/951,462, filed on Mar. 11, 2014.

(51) Int. Cl.
*B01L 3/00* (2006.01)
*C12Q 1/6869* (2018.01)
(Continued)

(52) U.S. Cl.
CPC .......... *C12Q 1/6869* (2013.01); *B01L 3/5027* (2013.01); *B01L 3/502707* (2013.01);
(Continued)

(58) Field of Classification Search
CPC ....... C40B 60/06; C40B 20/00; C12Q 1/6869; C12Q 1/68; B01L 3/5027; B01L 3/502; B01L 3/50
(Continued)

(56) References Cited

U.S. PATENT DOCUMENTS 6,172,218 B1   1/2001   Brenner
6,210,891 B1   4/2001   Nyren et al.
(Continued)

FOREIGN PATENT DOCUMENTS

DE   102010002990   9/2011
WO   1991/006678 A1   5/1991
(Continued)

OTHER PUBLICATIONS

XiMU, subminature USB2.0 cameras, ximea, (obtained on Sep. 4, 2018, published by xiMu—Nov. 2016). (Year: 2016).*
(Continued)

*Primary Examiner* — Christine T Mui
(74) *Attorney, Agent, or Firm* — Illumina, Inc.

(57) ABSTRACT

The disclosed embodiments concern microfluidic cartridges for detecting biological reactions. In some embodiments, the microfluidic cartridges are configured to perform sequencing operations on a nucleic acid sample. In one aspect, a microfluidic cartridge includes a stack of fluidics layers defining channels and valves for processing the nucleic acid sample to be sequenced, and a solid state CMOS biosensor integrated in the stack. The biosensor has an active area configured to detect signals of biological reactions, wherein substantially all of the active area is available for reagent
(Continued)

delivery and illumination during operation. In another aspect, a microfluidic cartridge includes: (a) a flow cell including a reaction site area encompassing one or more reaction sites; (b) fluidics channels for delivering reactants to and/or removing reactants from the reaction site area; (c) a biosensor having an active area configured to detect signals of biological reactions in the reaction site area. The reaction site area is proximal to the active area of the biosensor and the reaction site area spans substantially all of the active area of the biosensor. In some embodiments, the fluidics channels do not substantially overlap with the active area of the biosensor. Methods for manufacturing and operating the microfluidic cartridges are also disclosed.

13 Claims, 63 Drawing Sheets

(51) Int. Cl.
  *B01L 7/00* (2006.01)
  *C12Q 1/6806* (2018.01)
  *C40B 60/06* (2006.01)

(52) U.S. Cl.
  CPC .......... *B01L 3/502738* (2013.01); *B01L 7/52* (2013.01); *C12Q 1/6806* (2013.01); *B01L 3/502715* (2013.01); *B01L 2200/10* (2013.01); *B01L 2200/12* (2013.01); *B01L 2300/0636* (2013.01); *B01L 2300/0654* (2013.01); *B01L 2300/0809* (2013.01); *B01L 2300/0867* (2013.01); *B01L 2300/0874* (2013.01); *B01L 2300/0887* (2013.01); *B01L 2300/123* (2013.01); *B01L 2300/165* (2013.01); *B01L 2300/1827* (2013.01); *B01L 2400/0487* (2013.01); *B01L 2400/0644* (2013.01); *B01L 2400/0655* (2013.01)

(58) Field of Classification Search
  USPC .................. 506/2, 36, 33; 422/502, 500, 50
  See application file for complete search history.

(56) References Cited

U.S. PATENT DOCUMENTS

| | | | |
|---|---|---|---|
| 6,258,568 B1 | 7/2001 | Nyren | |
| 6,274,320 B1 | 8/2001 | Rothberg et al. | |
| 6,306,597 B1 | 10/2001 | Macevicz | |
| 6,969,488 B2 | 11/2005 | Bridgham et al. | |
| 7,001,792 B2 | 2/2006 | Sauer et al. | |
| 7,057,026 B2 | 6/2006 | Barnes et al. | |
| 7,211,414 B2 | 5/2007 | Hardin et al. | |
| 7,315,019 B2 | 1/2008 | Turner et al. | |
| 7,329,492 B2 | 2/2008 | Hardin et al. | |
| 7,329,860 B2 | 2/2008 | Feng et al. | |
| 7,405,281 B2 | 7/2008 | Xu et al. | |
| 7,427,673 B2 | 9/2008 | Balasubramanian et al. | |
| 7,595,883 B1 | 9/2009 | El Gamal et al. | |
| 8,906,320 B1 | 12/2014 | Eltoukhy et al. | |
| 2005/0100900 A1 | 5/2005 | Kawashima et al. | |
| 2005/0244870 A1 | 11/2005 | Chee et al. | |
| 2006/0188901 A1 | 8/2006 | Barnes et al. | |
| 2006/0240439 A1 | 10/2006 | Smith et al. | |
| 2006/0281109 A1 | 12/2006 | Barr Ost et al. | |
| 2007/0166705 A1 | 7/2007 | Milton et al. | |
| 2007/0263046 A1 | 11/2007 | Iwasa et al. | |
| 2008/0037008 A1 | 2/2008 | Shepard et al. | |
| 2008/0108082 A1 | 5/2008 | Rank et al. | |
| 2009/0026082 A1 | 1/2009 | Rothberg et al. | |
| 2009/0032401 A1* | 2/2009 | Ronaghi .......... B01L 3/502761 204/549 |
| 2009/0127589 A1 | 5/2009 | Rothberg et al. | |
| 2010/0111768 A1 | 5/2010 | Banerjee et al. | |
| 2010/0137143 A1 | 6/2010 | Rothberg et al. | |
| 2010/0282617 A1 | 11/2010 | Rothberg | |
| 2011/0308313 A1 | 12/2011 | Azimi et al. | |
| 2012/0270305 A1 | 10/2012 | Reed et al. | |
| 2013/0079232 A1 | 3/2013 | Kain et al. | |
| 2013/0116128 A1 | 5/2013 | Shen et al. | |
| 2013/0210682 A1* | 8/2013 | Eltoukhy .......... B01L 3/502715 506/38 |
| 2013/0260372 A1* | 10/2013 | Buermann .......... G01N 21/6428 435/6.1 |

FOREIGN PATENT DOCUMENTS

| | | | |
|---|---|---|---|
| WO | 2004/018497 A2 | 3/2004 | |
| WO | 2005/065814 A1 | 7/2005 | |
| WO | 2006/064199 A1 | 6/2006 | |
| WO | 2007/010251 A1 | 1/2007 | |
| WO | 2007/123744 A2 | 11/2007 | |
| WO | 2009/126257 | 10/2009 | |
| WO | 2012/058096 A1 | 5/2012 | |
| WO | 2015/031849 | 3/2015 | |
| WO | WO 2015/138648 A1 | 9/2015 | |

OTHER PUBLICATIONS

International Search Report and Written Opinion dated Aug. 10, 2015 issued in PCT/US15/20029.
Cockroft, et al., "A Single-Molecule Nanopore Device Detects DNA Polymerase Activity with Single-Nucleotide Resolution," J. Am. Chem. Soc, 130(3), 818-820, Jan. 23, 2008.
Deamer, et al., "Nanopores and nucleic acids: prospects for ultrarapid sequencing," Trends in Biotechnology, 18(4), 147-151, 2000.
Deamer, et al., "Characterization of Nucleic Acids by Nanopore Analysis," ACC Chem Res, 35(10), 817-825, 2002.
Giraud, et al., "Fluorescence lifetime biosensing with DNA microarrays and a CMOS-SPAD imager," Biomedical Optics Express, 1(5), 1302-1308, Nov. 4, 2010.
Healy, K., "Nanopore-based single-molecule DNA analysis," Nanomedicine, 2(4), 459-481, 2007.
Korlach, et al., "Selective aluminum passivation for targeted immobilization of single DNA polymerase molecules in zero-mode waveguide nanostructures," PNAS, 105(4), 1176-1181, Jan. 29, 2008.
Levene, et al., "Zero-Mode Waveguides for Single-Molecule Analysis at High Concentrations," Science, 299, 682-686, Jan. 31, 2003.
Li, et al., "DNA molecules and configurations in a solid-state nanopore microscope," Nature Materials, 2(9), 611-615, Sep. 2003.
Lundquist, et al., "Parallel confocal detection of single molecules in real time," Optics Letters, 33(9), 1026-1028, May 1, 2008.
Metzker, M., "Emerging technologies in DNA sequencing," Genome Research, 15, 1767-1776, 2005.
Ronaghi, et al., "A Sequencing Method Based on Real-Time Pyrophosphate," Science, 281 (5375), 363-365, Jul. 17, 1998.
Ronaghi, et al., "Real-time DNA Sequencing Using Detection of Pyrophosphate Release," Analytical Biochemistry, 24, 84-89, 1996.
Ronaghi, M., "Pyrosequencing sheds light on DNA sequencing," Genome Research, 11, 3-11, 2001.
Ruparel, et al., "Design and synthesis of a 3'-O-allyl photocleavable fluorescent nucleotide as a reversible terminator for DNA sequencing by synthesis," PNAS, 102 (17), 5932-5937, Apr. 26, 2005.
Soni, et al., "Progress toward Ultrafast DNA Sequencing Using Solid-State Nanopores," Clinical Chemistry, 53 (11), 1996-2001, 2007.
Stoppa, et al., "A 32x32-Pixel Array with in-Pixel Photon Counting and Arrival Time Measurement in the Analog Domain," IEEE European Solid-State Device Conference (ESSCIRC), Athens, Greece, IEEE, 204-207, 2009.

* cited by examiner

DISPOSABLE, INTEGRATED MICROFLUIDIC CARTRIDGE AND METHODS OF MAKING AND USING SAME

CROSS-REFERENCE TO RELATED APPLICATIONS

This application is filed pursuant to 35 U.S.C. § 371 as a United States National Phase Application of International Application No. PCT/US2015/020029 entitled: DISPOSABLE, INTEGRATED MICROFLUIDIC CARTRIDGE AND METHODS OF MAKING AND USING SAME, filed Mar. 11, 2015, which claims the benefit of and priority to U.S. Provisional Application Ser. No. 61/951,462, filed Mar. 11, 2014, and U.S. Provisional Application Ser. No. 61/987,699, filed May 2, 2014, the contents of which are incorporated herein by reference in their entireties and for all purposes.

BACKGROUND

It is difficult to manufacture an integrated microfluidic cartridge that has both complimentary metal-oxide-semiconductor (CMOS) technology, e.g., CMOS image sensors, and fluidic channels. In most cases the fluidic channel is designed within the CMOS surface, which reduces active area and leads to complicated flow patterns. Therefore, there is a need for new approaches to integrating CMOS technology into multi-compartment microfluidic cartridges. Further, there is a significant challenge to seal a polymerase chain reaction (PCR) area in a microfluidic cartridge due to microbubbles that are present in the PCR mix, and whereas these microbubbles expand during PCR. Consequently, there is a need for new approaches to sealing PCR areas in microfluidic cartridges.

SUMMARY

The disclosed embodiments concern microfluidic cartridges for detecting biological reactions. In some embodiments, the microfluidic cartridges are configured to perform sequencing operations on a nucleic acid sample. In one aspect, a microfluidic cartridge includes a stack of fluidics layers defining channels and valves for processing the nucleic acid sample to be sequenced, and a solid state CMOS biosensor integrated in the stack. The biosensor has an active area configured to detect signals of biological reactions, wherein substantially all of the active area is available for reagent delivery and illumination during operation. In another aspect, a microfluidic cartridge includes: (a) a flow cell including a reaction site area encompassing one or more reaction sites; (b) fluidics channels for delivering reactants to and/or removing reactants from the reaction site area; (c) a biosensor having an active area configured to detect signals of biological reactions in the reaction site area. The reaction site area is proximal to the active area of the biosensor and the reaction site area spans substantially all of the active area of the biosensor. In some embodiments, the fluidics channels do not substantially overlap with the active area of the biosensor.

In a first general aspect, a microfluidic cartridge is configured to perform sequencing operations on a nucleic acid sample. The microfluidic cartridge includes: (a) a bioassay system comprising a stack of fluidics layers defining channels and valves for processing the nucleic acid sample to be sequenced; and (b) a solid state CMOS biosensor integrated in the stack and fluidically and optically coupled to the bioassay system, the biosensor comprising an active area configured to detect signals of biological reactions, wherein substantially all of the active area is available for reagent delivery and illumination during operation. In some implementations, the microfluidic cartridge further includes a housing at least partially encasing the stack of fluidics layers and the CMOS biosensor. In some implementations, the bioassay system comprises a flow cell mounted on said biosensor.

In a second general aspect, a microfluidic cartridge for detecting biological reactions is disclosed. The microfluidic cartridge includes: (a) a flow cell including a reaction site area encompassing one or more reaction sites; (b) fluidics channels for delivering reactants to and/or removing reactants from the reaction site area; (c) a biosensor having an active area configured to detect signals of biological reactions in the reaction site area. In some implementations, the reaction site area is proximal to the active area of the biosensor, and the reaction site area spans all or substantially all of the active area of the biosensor. In some implementations, the fluidics channels do not substantially overlap or do not overlap with the active area of the biosensor.

In some implementations of the microfluidic cartridge in the second general aspect, the biosensor includes a photo detector. In some implementations, the photo detector is a CMOS or a CCD sensor. In some implementations, the CMOS sensor is about 9200 µm long, about 8000 µm wide, about 800-1000 µm thick, and has about 50 I/O pads.

In some implementations, the microfluidic cartridge of the second general aspect is configured to perform sequencing operations on a nucleic acid sample. The flow cell includes a sequencing chamber, and the detected signals of biological reactions are indicative of nucleotide base types involved in the biological reactions. In some implementations, the sequencing chamber is formed on a sequencing chamber layer, the biosensor is disposed in an opening on a sequencing chamber bottom layer under the sequencing chamber layer, and the fluidics channels are formed on a fluidics channels layer under the sequencing chamber bottom layer. In some implementations, the flow cell includes a substrate of hydrophilic regions for nucleic acid attachment and amplification surrounded by hydrophobic regions. In some implementations, reaction site area spans all of the active area of the biosensor.

In some implementations of the microfluidic cartridge in the first and second general aspect, the cartridge further includes: a PCR region, a reagent mixing and distributing region, and one or more membrane valves that are configured to reversibly stop the PCR region from fluidic communication with the reagent mixing and distribution region or the flow cell including the reaction site area. In some implementations, the microfluidic cartridge further includes a flexible PCB heater. In some implementations, the PCR region includes a plurality of PCR channels. In some implementations, the reagent mixing and distributing region includes a plurality of reagent channels and/or reagent supplies. In some implementations, the cartridge further includes a rotary valve that is configured to fluidly connect the PCR region to the reagent mixing and distributing region. In some implementations, the rotary valve is further configured to fluidly connect the reagent mixing and distributing region to the flow cell including a reaction site area.

In a third general aspect, a stack of fluidics layers of a microfluidic cartridge for sequencing nucleic acid molecules is disclosed. The stack of fluidics layers includes: (a) a sequencing chamber layer having a sequencing chamber area configured for carrying out clustering and sequencing reactions; (b) a sequencing chamber bottom layer disposed under the sequencing chamber layer, the sequencing chamber bottom layer has an opening configured to hold an image sensor with the image sensor's active area disposed under the sequencing chamber area; (c) a flexible printed circuit board (PCB) layer under the sequencing chamber bottom layer; and (d) a fluidics channels layer disposed under the flexible printed circuit board (PCB) layer, the fluidics channels layer including fluidic channels that are configured to deliver reactants to the sequencing chamber area.

In some implementations of the stack of fluidics layers, the sequencing chamber area spans substantially all of the active area of the image sensor. In some implementations, the fluidics channels do not substantially overlap with the active area of the image sensor. In some implementations, the sequencing chamber layer and the sequencing chamber bottom layer include openings for a plurality of membrane valves. In some implementations, the stack of fluidics layers further includes a membrane layer disposed above the sequencing chamber layer. The membrane layer, the openings on the sequencing chamber layer and the sequencing chamber bottom layer, and the flexible PCB layer are configured to form a plurality of membrane valves. In some implementations, at least some of the membrane valves are configured to provide reversible sealing of a PCR region of the microfluidic cartridge from a reagent mixing and distribution region of the microfluidic cartridge.

In a fourth general aspect, methods for operating microfluidic cartridges are provided. In some implementations, a method involves: (a) performing polymerase chain reaction on a sample in a PCR region of the microfluidic cartridge, and/or mixing the sample with one or more reagents in a reagent mixing and distribution region of the microfluidic cartridge; (b) transfer the sample through fluidic channels to a sequencing chamber, wherein the sequencing chamber: (1) is at a different location from the PCR region and/or the reagent mixing and distribution region, and (2) the sequencing chamber does not substantially overlap with the fluidic channels; (c) performing a sequencing reaction on the sample; and (d) imaging the sequencing reaction using an image sensor having an active area adjacent to the sequencing chamber. In some implementations, the sequencing chamber substantially spans all of the active area. In some implementations, the method further involves: sealing the PCR region from the reagent mixing and distribution region when performing the polymerase chain reaction; and transferring the sample from the PCR region to the reagent mixing and distribution region before mixing the sample with one or more reagents.

In a fifth general aspect, a method of manufacturing a microfluidic cartridge is provided. The method involves: (a) forming fluidics layers including a printed circuit board (PCB); (b) attaching an image sensor to the PCB, wherein the image sensor is positioned so that substantially all of the image sensor's active area is accessible for illumination and/or reagent delivery; (c) assembling a stack comprising the fluidics layers and the image sensor, and (d) forming the microfluidic cartridge including the fluidics layers and the image sensor. In some implementations, the image sensor is a CMOS image sensor.

In some implementations, the stack of fluidics layer includes: (a) a sequencing chamber layer comprising a sequencing chamber area configured for carrying out clustering and sequencing reactions; (b) a sequencing chamber bottom layer disposed under the sequencing chamber layer, the sequencing chamber bottom layer comprising an opening configured to contain an image sensor with the image sensor's active area disposed under the sequencing chamber area; (c) a flexible PCB layer including the PCB under the sequencing chamber bottom layer; and (d) a fluidics channels layer disposed under the flexible PCB layer, wherein the fluidics channels layer includes fluidic channels that are configured to deliver reactants to the sequencing chamber area. In some implementations, the fluidic channels do not overlap or at least do not substantially overlap with the sequencing chamber area.

INCORPORATION BY REFERENCE

All patents, patent applications, and other publications, including all sequences disclosed within these references, referred to herein are expressly incorporated herein by reference, to the same extent as if each individual publication, patent or patent application was specifically and individually indicated to be incorporated by reference. All documents cited are, in relevant part, incorporated herein by reference in their entireties for the purposes indicated by the context of their citation herein. However, the citation of any document is not to be construed as an admission that it is prior art with respect to the present disclosure.

BRIEF DESCRIPTION OF THE DRAWINGS

FIGS. 46A and 462B show a perspective view and plan view, respectively, of the sequencing chamber layer of the fluidics layers shown in FIG. 2 and FIG. 14;

DETAILED DESCRIPTION

Figure 1:
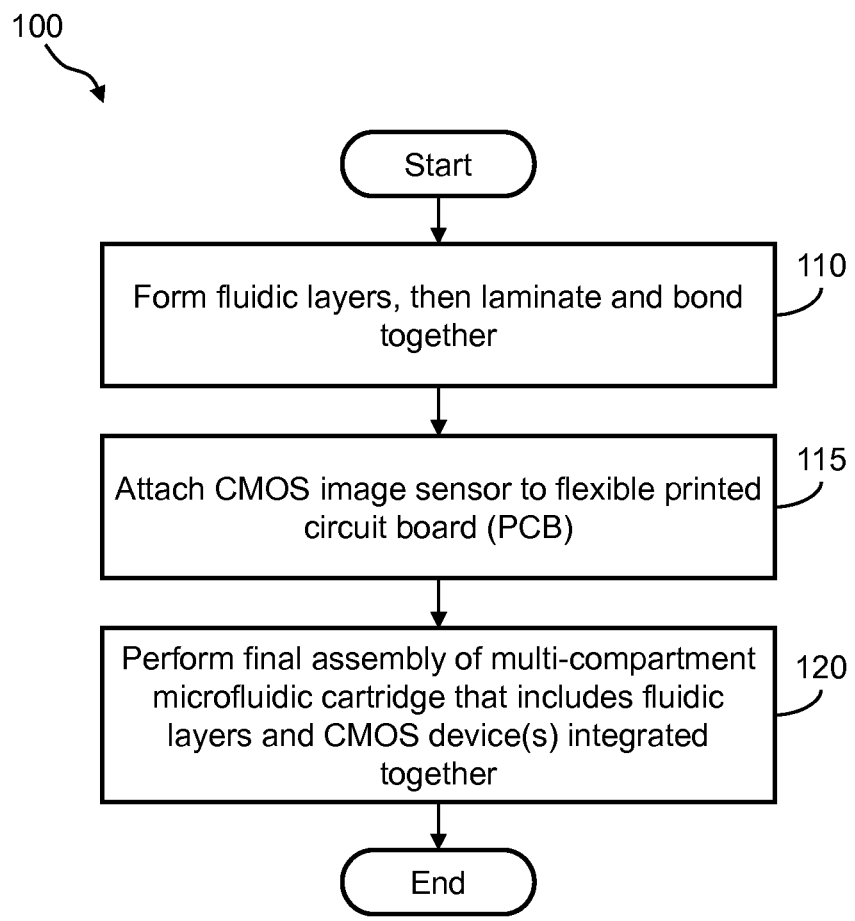
FIG. 1 illustrates a flow diagram of an example of a method of using a flexible printed circuit board (PCB) and roll-2-roll (R2R) printed electronics for the monolithic integration of CMOS technology and digital fluidics.

Unless otherwise indicated, the practice of the methods and systems disclosed herein involves conventional techniques and apparatus commonly used in molecular biology, microbiology, protein purification, protein engineering, protein and DNA sequencing, and recombinant DNA fields that are within the skill of the art. Such techniques and apparatus are known to those of skill in the art and are described in numerous texts and reference works (See e.g., Sambrook et al., "Molecular Cloning: A Laboratory Manual," Third Edition (Cold Spring Harbor), [2001]); and Ausubel et al., "Current Protocols in Molecular Biology" [1987]).

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not intended to limit the disclosure.

Unless defined otherwise herein, all technical and scientific terms used herein have the same meaning as commonly understood by one of ordinary skill in the art. Various scientific dictionaries that include the terms included herein are well known and available to those in the art. Although any methods and materials similar or equivalent to those described herein find use in the practice or testing of the embodiments disclosed herein, some methods and materials are described.

The terms defined immediately below are more fully described by reference to the Specification as a whole. It is to be understood that this disclosure is not limited to the particular methodology, protocols, and reagents described, as these may vary, depending upon the context they are used by those of skill in the art.

Introduction

Sequencing Methods

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques.

"Sequencing-by-synthesis (SBS) techniques" generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail below. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be attached to features in an array and the array can be imaged to capture the chemiluminscent signals that are produced due to incorporation of nucleotides at the features of the array. An image can be obtained after the array is treated with a particular nucleotide type (e.g., A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in International Patent Pub. No. WO 04/018497 and U.S. Pat. No. 7,057,026, the disclosures of which are incorporated herein by reference. This approach is being commercialized by Solexa (now Illumina Inc.), and is also described in International Patent Pub. No. WO 91/06678 and International Patent Pub. No. WO 07/123,744, each of which is incorporated herein by reference. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments each image will show nucleic acid features that have incorporated nucleotides of a particular type. Different features will be present or absent in the different images due to the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluorescent labels can include fluorescent labels linked to the ribose moiety via a 3' ester linkage (Metzker, Genome Res. 15:1767-1776 (2005), which is incorporated herein by reference). Other approaches have separated the terminator chemistry from the cleavage of the fluorescence label (Ruparel et al., Proc Natl Acad Sci USA 102: 5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluorescent label and effectively reverses the termination. Examples of modified nucleotides are also described in U.S. Pat. Nos. 7,427,673, and 7,057,026, the disclosures of which are incorporated herein by reference in their entireties.

Additional exemplary SBS systems and methods which can be utilized with the methods and systems described herein are described in U.S. Patent Pub. No. 2007/0166705, U.S. Patent Pub. No. 2006/0188901, U.S. Pat. No. 7,057, 026, U.S. Patent Pub. No. 2006/0240439, U.S. U.S. Patent Pub. No. 2006/0281109, International Patent Pub. No. WO 05/065814, U.S. Patent Pub. No. 2005/0100900, International Patent Pub. No. WO 06/064199, International Patent Pub. No. WO 07/010,251, U.S. U.S. Patent Pub. No. 2012/0270305 and U.S. Patent Pub. No. 2013/0260372, the disclosures of which are incorporated herein by reference in their entireties.

Some embodiments can utilize detection of four different nucleotides using fewer than four different labels. For example, SBS can be performed utilizing methods and systems described in the incorporated materials of U.S. Patent Pub. No. 2013/0079232, which is incorporated herein by reference in its entirety for the purposes indicated by the context of the citation herein.

As a first example, a pair of nucleotide types can be detected at the same wavelength, but distinguished based on a difference in intensity for one member of the pair compared to the other, or based on a change to one member of the pair (e.g., via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc.). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g., dATP having a label that is detected in the first channel when excited by a first excitation wavelength), a second nucleotide type that is detected in a second channel (e.g., dCTP having a label that is detected in the second channel when excited by a second excitation wavelength), a third nucleotide type that is detected in both the first and the second channel (e.g., dTTP having at least one label that is detected in both channels when excited by the first and/or second excitation wavelength) and a fourth nucleotide type that lacks a label that is not, or minimally, detected in either channel (e.g., dGTP having no label).

Further, as described in the incorporated materials of U.S. Patent Pub. No. 2013/0079232, which is incorporated herein by reference in its entirety for the purposes indicated by the context of the citation here, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that are set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414 (each of which is incorporated herein by reference) or nucleotide incorporations can be detected with zero-mode waveguides as described, for example, in U.S. Pat. No. 7,315,019 (which is incorporated herein by reference) and using fluorescent nucleotide analogs and engineered polymerases as described, for example, in U.S. Pat. No. 7,405,281 and U.S. Patent Pub. No. 2008/0108082 (each of which is incorporated herein by reference). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in U.S. Patent Pub. No. 2009/0026082; U.S. Patent Pub. No. 2009/0127589; U.S. Patent Pub. No. 2010/0137143; or U.S. Patent Pub. No. 2010/0282617, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

An advantage of the methods set forth herein is that they provide for rapid and efficient detection of a plurality of target nucleic acid in parallel.

Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in U.S. Patent Pub. No. 2010/0111768 A1 and U.S. patent application Ser. No. 13/273,666, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, Calif.) and devices described in U.S. patent application Ser. No. 13/273,666, which is incorporated herein by reference.

CMOS Technology

Complimentary metal-oxide-semiconductor (CMOS) is a technology for manufacturing integrated circuit, including digital logic circuits (e.g., microprocessors) and analog circuits (e.g., CMOS image sensors).

"Activity detector" means any device or component that is capable of detecting the activity that is indicative of a desired reaction. An activity detector may be able detect predetermined events, properties, qualities, or characteristics within a predefined volume or area. For example, an activity detector may be able to capture an image of the predefined volume or area. An activity detector may be able detect an ion concentration within a predefined volume of a solution or along a predefined area. Exemplary activity detectors include charged-coupled devices (CCD's) (e.g., CCD cameras); photomultiplier tubes (PMT's); molecular characterization devices or detectors, such as those used with nanopores; microcircuit arrangements, such as those described in U.S. Pat. No. 7,595,883, which is incorporated herein by reference in the entirety; and CMOS-fabricated sensors having field effect transistors (FET's), including chemically sensitive field effect transistors (chemFET), ion-sensitive field effect transistors (ISFET), and/or metal oxide semiconductor field effect transistors (MOSFET). Exemplary activity detectors are described, for example, in International Patent Pub. No. WO2012/058095, which is incorporated herein by reference in its entirety for the purposes indicated by the context of the citation here.

"Biosensor" means any structure having a plurality of reaction sites. A biosensor may include a solid-state imaging device (e.g., CCD or CMOS imager) and, optionally, a flow cell mounted thereto. The flow cell may include at least one flow channel that is in fluid communication with the reaction sites. As one specific example, the biosensor is configured to fluidically and electrically couple to a bioassay system. The bioassay system may deliver reactants to the reaction sites according to a predetermined protocol (e.g., sequencing-by synthesis) and perform a plurality of imaging events. An area encompassing the reaction sites is referred to as a "reaction site area." For example, the bioassay system may direct solutions to flow along the reaction sites in the reaction site area. In some embodiments of this disclosure, the reaction site area is different and separate from fluidics channels directing solutions to and from the reaction site area. In some applications, at least one of the solutions may include four types of nucleotides having the same or different fluorescent labels. The nucleotides may bind to corresponding oligonucleotides located at the reaction sites. The bioassay system may then illuminate the reaction sites using an excitation light source (e.g., solid-state light sources, such as light-emitting diodes or LEDs). The excitation light may have a predetermined wavelength or wavelengths, including a range of wavelengths. The excited fluorescent labels provide emission signals that may be detected by the light detectors.

In one aspect, the solid-state imager includes a CMOS image sensor comprising an array of light detectors that are configured to detect the emission signals. In some embodiments, each of the light detectors has only a single pixel and wherein a ratio of the pixels to the detection paths defined by the filter walls is substantially one-to-one. Exemplary biosensors are described, for example, in U.S. patent application Ser. No. 13/833,619, which is incorporated herein by reference in its entirety for the purposes indicated by the context of the citation here.

"Detection surface" means any surface that includes an optical detector. The detector can be based upon any suitable technology, such as those including a charge coupled device (CCD) or a complementary metal-oxide-semiconductor (CMOS). In particular embodiments a CMOS imager having a single-photon avalanche diode (CMOS-SPAD) can be used, for example, to distinguish fluorophores using fluorescence lifetime imaging (FLIM). Exemplary CMOS based systems that can be used for FLIM are described in U.S. Patent Pub. No. 2008/0037008 A1; Giraud et al., Biomedical Optics Express 1: 1302-1308 (2010); or Stoppa et al., IEEE European Solid-State Device Conference (ESSCIRC), Athens, Greece, IEEE, pp. 204-207 (2009), each of which is incorporated herein by reference in its entirety. Other useful detection devices that can be used include, for example, those described in U.S. Pat. No. 7,329,860 and U.S. Patent Pub. No. 2010/0111768, each of which is incorporated herein by reference in its entirety.

In addition, it will be appreciated that other signal detecting devices as known in the art can be used to detect signals produced in a method set forth herein. For example detectors used to detect pyrophosphate or protons are particularly useful. Pyrophosphate release can be detected using detectors such as those commercially available from 454 Life Sciences (Branford, Conn., a Roche Company) or described in U.S. Patent Pub. No. 2005/0244870, which is incorporated herein by reference in its entirety. Exemplary systems for detecting primer extension based on proton release include those that are commercially available from Ion Torrent (Guilford, Conn., a Life Technologies subsidiary) or described in U.S. Patent Pub. Nos. 2009/0026082; 2009/0127589; 2010/0137143; and 2010/0282617, each of which is incorporated herein by reference in its entirety. Exemplary detection surfaces and detectors are described, for example, in Min-Jui Richard et al., U.S. Patent Pub. No. 20130116128, entitled "Integrated Sequencing Apparatuses and Methods of Use," published on May 9, 2013, each of which is incorporated herein by reference in its entirety for the purposes indicated by the context of the citation here.

"Sequencing module" means a CMOS chip that has been adapted for sequencing applications. In some embodiments, the module can comprise a surface comprising a substrate of hydrophilic regions for nucleic acid attachment and amplification surrounded by hydrophobic regions. For example, dynamic pads having a hydrophilic patch, such as those described above, can be used. Alternatively or additionally, a collection of dynamic pads including some that are in a hydrophilic state while surrounding pads are in a hydrophobic state can form a hydrophilic regions surrounded by a hydrophobic region. The surface for nucleic acid attachment would optionally comprise a plurality of isolated regions such that each isolated region contains a plurality of nucleic acid molecules that is preferably derived from one nucleic acid molecule for sequencing. For example, the hydrophilic region can include a gel. The hydrophilic regions could be smooth, textured, porous, non-porous, etc. The hydrophobic regions are preferably located between the hydrophilic regions. Reagents move across the surface by way of any number of forces.

Disposable, Integrated Microfluidic Cartridge

The present disclosure provides a disposable, integrated microfluidic cartridge and methods of making and using same. The method of making the disposable, integrated microfluidic cartridge utilizes a flexible printed circuit board (PCB) and roll-2-roll (R2R) printed electronics for the monolithic integration of CMOS technology and digital fluidics. Namely, the disposable, integrated microfluidic cartridge includes a stack of fluidics layers in which a CMOS sensor is integrated, all installed in a housing. Accordingly, conventional injection molded fluidics can be integrated with flexible PCB technology. The fluidics layers are formed using materials that are suitable for use in a R2R printed electronics process for creating electronic devices on a roll of flexible plastic or metal foil. Further, the fluidics layers include a polymerase chain reaction (PCR) region and a reagent mixing and distribution region. The fluidics layers also include a set of membrane valves by which the PCR region can be completely sealed off.

The method of using the disposable, integrated microfluidic cartridge includes performing multiplex PCR on the cartridge and downstream mixing needed for sequencing.

The present disclosure provides a CMOS flow cell, wherein most or up to about 100% of the biosensor active area is accessible for reagent delivery and illumination.

FIG. 1 illustrates a flow diagram of an example of a method 100 of using a flexible printed circuit board (PCB) and roll-2-roll (R2R) printed electronics for the monolithic integration of CMOS technology and digital fluidics. Namely, using method 100, multilayer laminated fluidics can be integrated with flexible PCB technology (see FIG. 2). Further, using the structure formed from applying method 100, conventional injection molded fluidics can be integrated with flexible PCB technology (see FIGS. 13 through 32). Method 100 may include, but is not limited to, the following steps.

Figure 2:
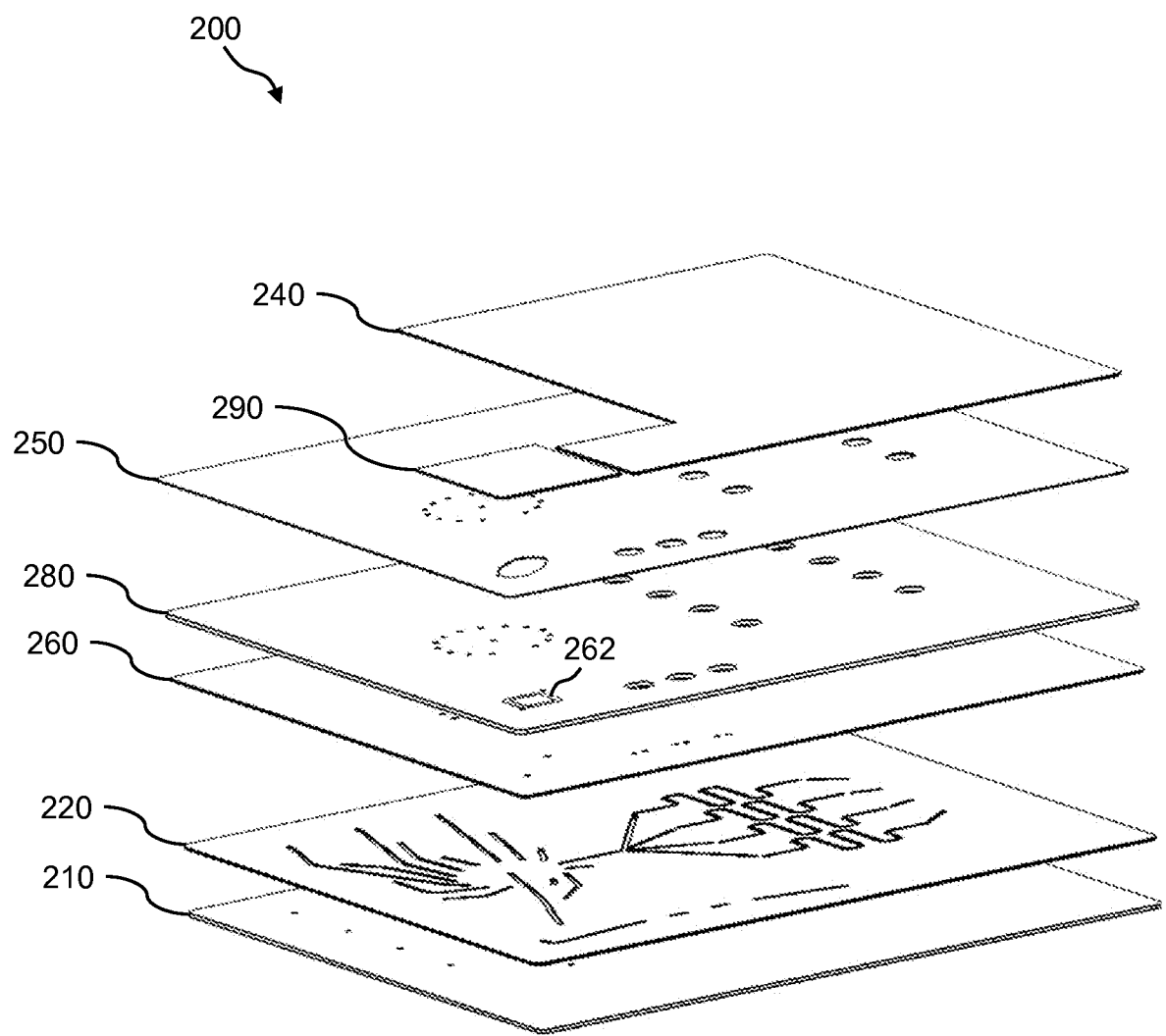
FIG. 2 illustrates an exploded view of an example of a fluidics stack having certain layers that can be laminated and bonded together using the method of FIG. 1.

At a step 110, the fluidic layers are formed and then laminated and bonded together. For example, FIG. 2 illustrates an exploded view of a set of fluidics layers 200 that can be laminated and bonded together in this step. In this example, fluidics layers 200 comprises, in order, an inlet/outlet ports layer 210, a fluidics channels layer 220, a flexible PCB layer 260, a sequencing chamber bottom layer 280, a sequencing chamber layer 250, and a membrane layer 240 that is coplanar with a sequencing chamber top layer 290. Inlet/outlet ports layer 210, fluidics channels layer 220, flexible PCB layer 260, sequencing chamber bottom layer 280, sequencing chamber layer 250, membrane layer 240, and sequencing chamber top layer 290 are suitable for forming using a R2R printed electronics process. In some implementations, other layers may also be formed using R2R processes. Moreover, suitable processes for forming layers on PCB other than R2R may be used to form the fluidics layers in some implementations.

Inlet/outlet ports layer 210 can be formed of, for example, polycarbonate, poly(methyl methacrylate) (PMMA), cyclic olefin copolymer (COC), and/or polyimide. Inlet/outlet ports layer 210 can be from about 25 μm to about 1000 μm thick in one example, or is about 250 μm thick in another example. An arrangement of openings (or holes) is provided in inlet/outlet ports layer 210. The openings (or holes) provide fluid paths the can serve as inlet ports and/or outlet ports to, for example, various liquid supply reservoirs (not shown). More details of inlet/outlet ports layer 210 are shown and described herein below with reference to FIGS. 42A and 42B.

Fluidics channels layer 220 can be formed of, for example, polycarbonate, PMMA, COC, and/or polyimide. Fluidics channels layer 220 can be from about 25 μm to about 1000 μm thick in one example, or is about 250 μm thick in another example. An arrangement of fluidics channels is provided in fluidics channels layer 220. The fluidics channels provide fluid paths from one destination to another along fluidics layers 200. Because fluidics channels layer 220 is sandwiched between inlet/outlet ports layer 210 and flexible PCB layer 260, fluid can be confined within the fluidics channels by inlet/outlet ports layer 210 on the bottom and by flexible PCB layer 260 on the top. In one example, fluidics channels layer 220 is used to perform PCR and downstream mixing needed for sequencing. More details of fluidics channels layer 220 are shown and described herein below with reference to FIGS. 43A and 43B.

Flexible PCB layer 260 can be formed of, for example, polycarbonate, PMMA, COC, and/or polyimide. Flexible PCB layer 260 can be from about 30 μm to about 300 μm thick in one example, or is about 200 μm thick in another example. An arrangement of openings (or holes) is provided in flexible PCB layer 260. The openings (or holes) provide fluid paths the can serve as inlets and/or outlets of membrane valves that are used to control the flow of liquid in the fluidics channels of fluidics channels layer 220. More details of flexible PCB layer 260 are shown and described herein below with reference to FIGS. 44A and 44B.

Sequencing chamber bottom layer 280 can be formed of, for example, polycarbonate, PMMA, COC, and/or polyimide. Sequencing chamber bottom layer 280 can be from about 25 μm to about 1000 μm thick in one example, or is about 250 μm thick in another example. An arrangement of openings is provided in sequencing chamber bottom layer 280 for forming the membrane valves within the stack of fluidics layers 200. Sequencing chamber bottom layer 280 also includes a CMOS device, such as a CMOS image sensor 262, that is located in proximity to the sequencing chamber of sequencing chamber layer 250. Sequencing chamber bottom layer 280 is coplanar with the CMOS device and acts as the fluid connecting layer to the inlet/outlet of the sequencing chamber of sequencing chamber layer 250. More details of sequencing chamber bottom layer 280 can be shown and described herein below with reference to FIGS. 45A and 45B.

Sequencing chamber layer 250 can be formed of, for example, polycarbonate, PMMA, COC, and/or polyimide. Sequencing chamber layer 250 can be from about 50 μm to about 300 μm thick in one example, or is about 100 μm thick in another example. An arrangement of openings is provided in sequencing chamber layer 250 for forming the membrane valves within the stack of fluidics layers 200. Sequencing chamber layer 250 also includes a sequencing chamber. More details of sequencing chamber layer 250 are shown and described herein below with reference to FIGS. 46A and 46B.

Membrane layer 240 can be formed of, for example, silicone elastomer. Membrane layer 240 can be from about 25 μm to about 1000 μm thick in one example, or is about 250 μm thick in another example. Membrane layer 240 serves as the elastic membrane for opening and closing the membrane valves within the stack of fluidics layers 200, wherein the membrane valves are created by the combination of, in order, flexible PCB layer 260, sequencing chamber bottom layer 280, sequencing chamber layer 250, and membrane layer 240. More details of membrane valves are shown and described herein below with reference to FIGS. 9A, 9B, 10A and 10B. More details of membrane layer 240 are shown and described herein below with reference to FIGS. 47A and 47B.

Sequencing chamber top layer 290 is formed of a low auto-fluorescent material that has good optical properties, such as COC. Sequencing chamber top layer 290 can be from about 25 μm to about 1000 μm thick in one example, or is about 250 μm thick in another example. Sequencing chamber top layer 290 is used to cover the sequencing chamber in sequencing chamber layer 250. More details of sequencing chamber top layer 290 are shown and described herein below with reference to FIGS. 47A and 47B.

Figure 3:
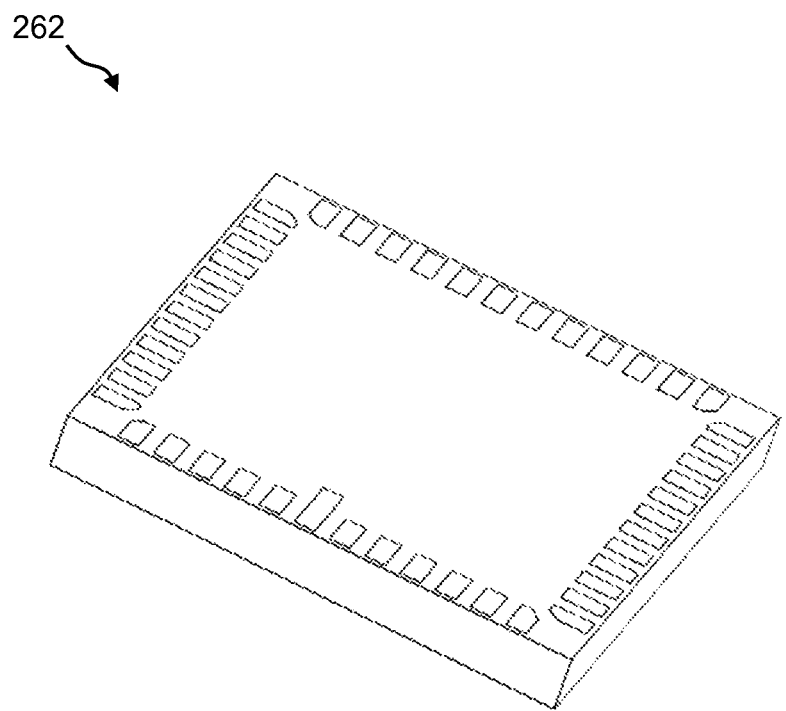
FIG. 3 illustrates a perspective view of an example of a CMOS device that can be integrated into the fluidics layers of a microfluidic cartridge using the method of FIG. 1.

Referring now again to FIG. 1, at a step 115, a CMOS device is attached to the flexible PCB. For example, a CMOS image sensor 262 (see FIG. 2) is attached to sequencing chamber bottom layer 280 of fluidics layers 200. FIG. 3 illustrates a perspective view of an example of CMOS image sensor 262. In one example, CMOS image sensor 262 is about 9200 μm long, about 8000 μm wide, and about 800-1000 μm thick; and can have about 50 I/O pads. CMOS image sensor 262 can comprise a pixel array. In one example, the pixel array is 4384×3292 pixels, with overall dimensions of 7272 μm×5761 μm.

Figure 4A:
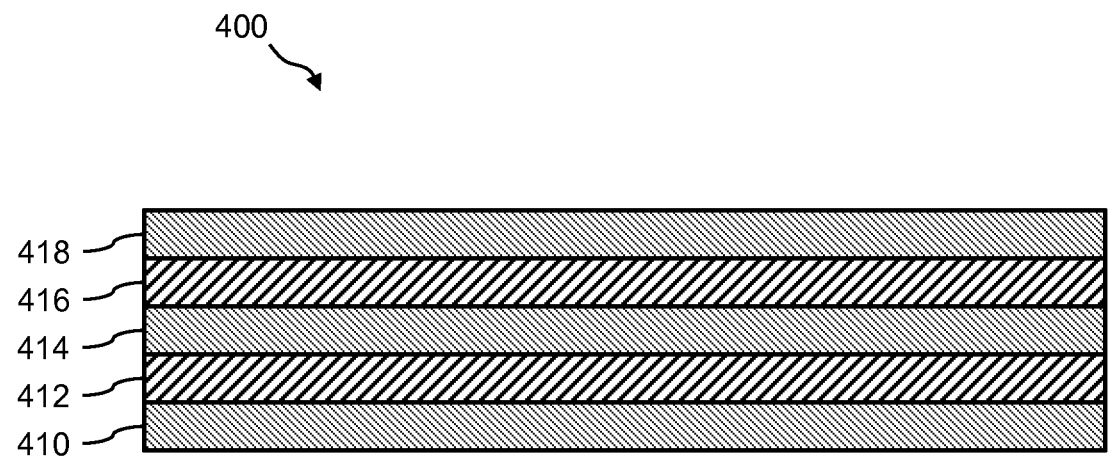
FIGS. 4A, 4B, 5, 6, and 7 illustrate side views of a structure and showing an example of a process of attaching a CMOS device to a flexible PCB using the method of FIG. 1.

Continuing step 115, FIGS. 4A, 4B, 5, 6, and 7 illustrate side views of a structure 400, which shows an example of a process of attaching a CMOS device to a flexible PCB. Structure 400 is a multilayer structure. Referring now to FIG. 4A, the initial formation of structure 400 begins with a flexible PCB. For example, the flexible PCB includes, in order, a polyimide layer 410, a PCB heater layer 412, a polyimide layer 414, a PCB wiring layer 416, and a polyimide layer 418. Namely, FIG. 4 shows a flexible PCB having a PCB heater layer and a PCB wiring layer, aka coupon foil.

Figure 4B:
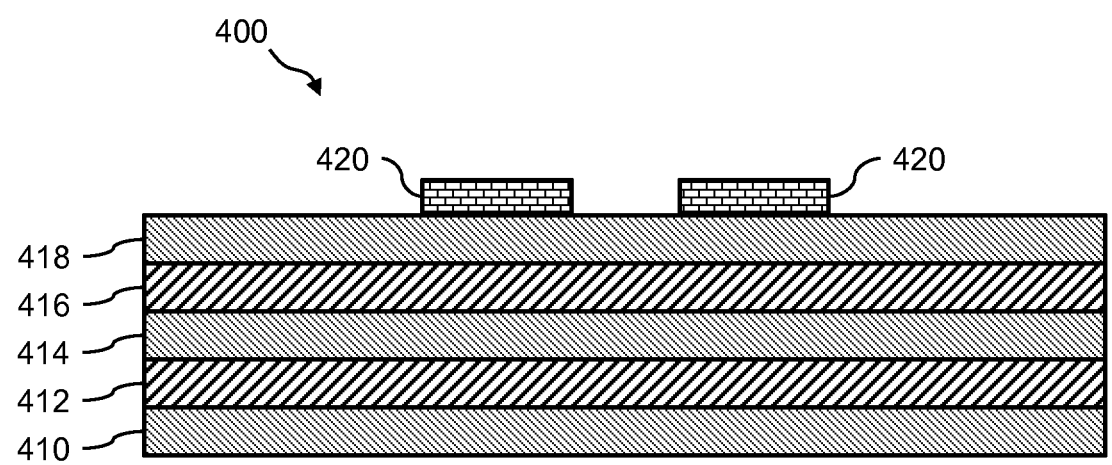

Next and referring now to FIG. 4B, a low-temperature isotropic conductive adhesive (low-temp ICA) 420 is dispensed atop polyimide layer 418.

Figure 5:
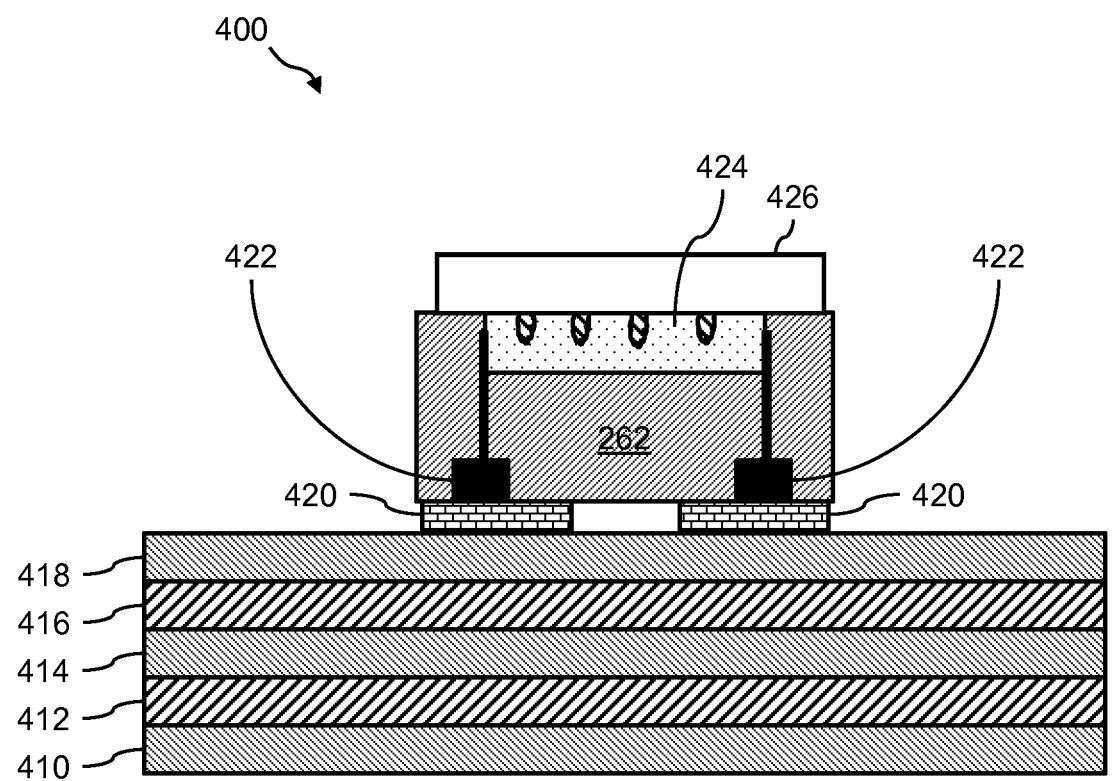

Next and referring now to FIG. 5, a CMOS device, such as CMOS image sensor 262, is placed on the coupon foil; namely, atop low-temp ICA 420. In one example, CMOS image sensor 262 is placed atop low-temp ICA 420 using a pick and place process that is well known. FIG. 5 shows I/O pads 422 of CMOS image sensor 262 are in contact with low-temp ICA 420 and thereby electrically connected to PCB wiring layer 416. FIG. 5 also shows that CMOS image sensor 262 includes a biolayer 424 that is facing away from polyimide layer 418. A protection film 426 can be placed atop biolayer 424 until ready for use.

Figure 6:
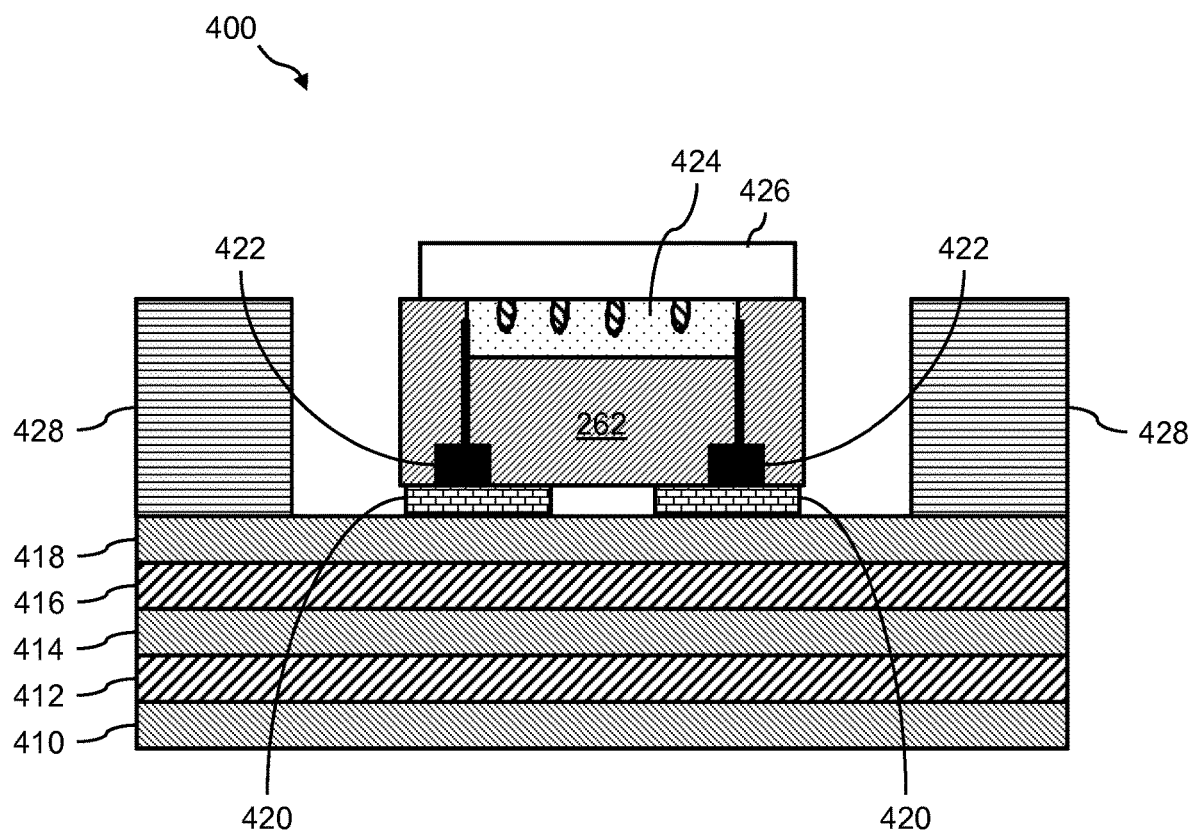

Next and referring now to FIG. 6, a set of fluidic layers 428 is provided atop polyimide layer 418 of the flexible PCB. Namely, a laminated polycarbonate film is provided that is coplanar to the CMOS surface. An example of fluidic layers 428 is fluidics layers 200 shown in FIG. 2.

Figure 7:
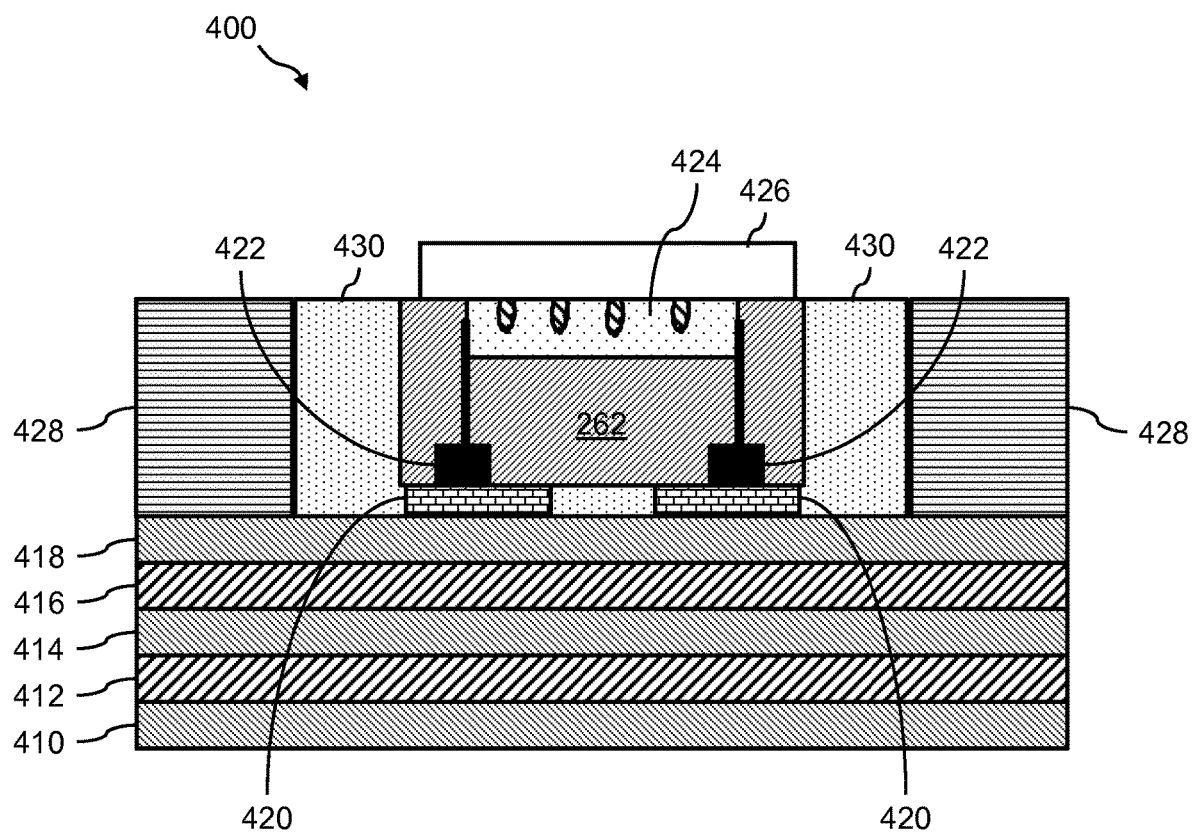

Next and referring now to FIG. 7, the flip-chip bonding of CMOS image sensor 262 on the coupon foil is completed by dispensing under-fill epoxy adhesive 430 in the gaps around CMOS image sensor 262.

Figure 8:
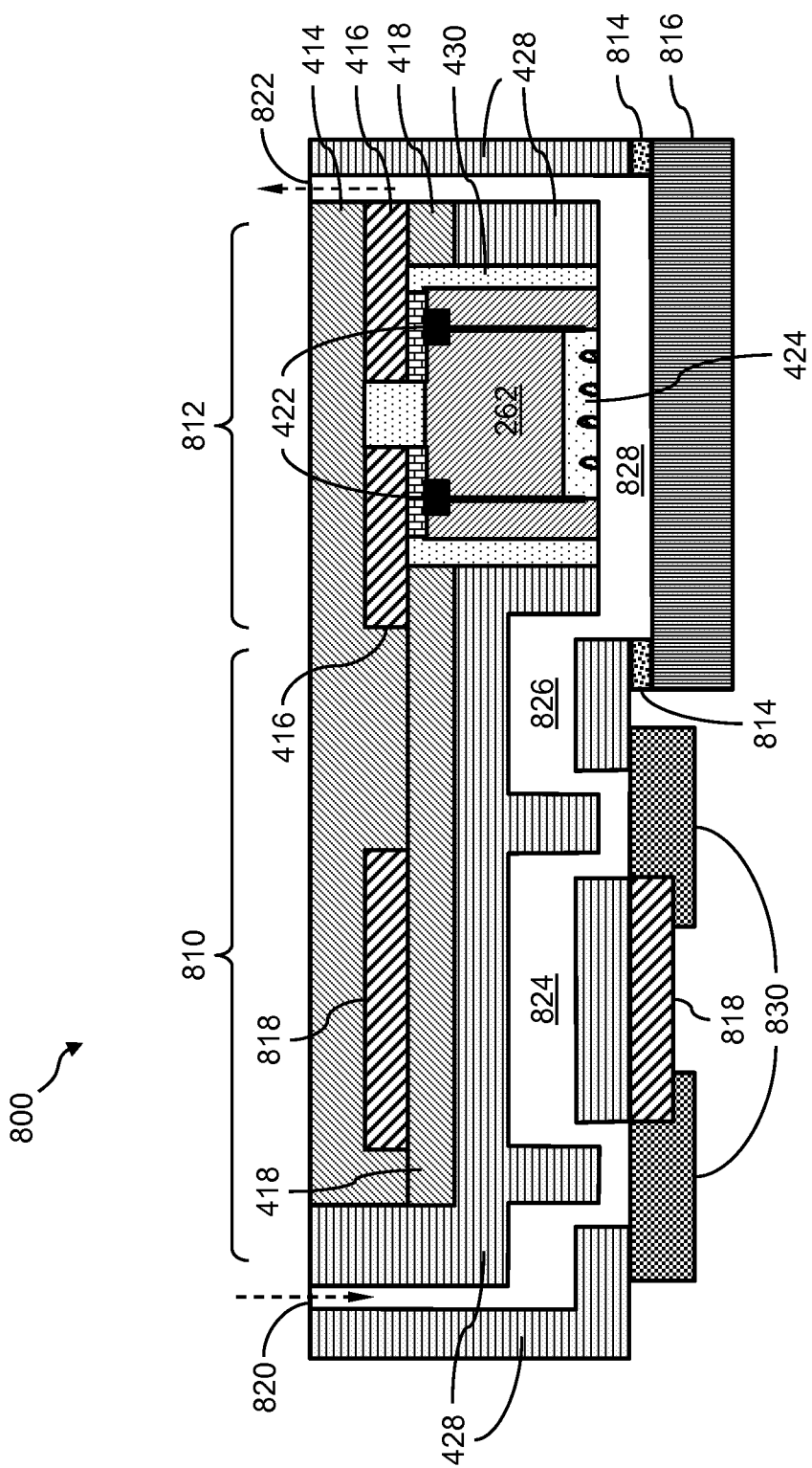
FIG. 8 illustrates a side view of an example of a structure formed using the method of FIG. 1, wherein the fluidics layers and a CMOS device are integrated together in a microfluidic cartridge.

Referring now again to FIG. 1, at a step 120, the final assembly of a microfluidic cartridge that includes fluidic layers and CMOS device(s) integrated together is performed. For example, FIG. 8 illustrates a side view of an example of a microfluidic cartridge 800. Microfluidic cartridge 800 includes a fluidics portion 810 and a CMOS portion 812, which is based on structure 400 shown in FIG. 7. Final assembly steps may include, for example, dispensing (printing) the under-fill epoxy adhesive 430, removing the protection film 426, laminating a low-temperature non-conductive adhesive 814 (e.g., UV or thermal non-conductive adhesive) at CMOS portion 812, laminating a low-autofluorescent cyclic olefin copolymer (COC) layer 816 to CMOS portion 812 of microfluidic cartridge 800, and laminating a flexible PCB heater 818 on both sides of fluidics portion 810. In the process of forming microfluidic cartridge 800, a self-aligned process flow is often used so that the surfaces of the CMOS device and the fluidic layers are flush with each other.

A fluid path is formed through microfluidic cartridge 800. Namely, a sample inlet 820 is provided at the input of fluidics portion 810 and an outlet 822 is provided downstream of CMOS portion 812. Sample inlet 820 supplies a PCR chamber 824. Then PCR chamber 824 supplies a reagent distribution region 826. Then reagent distribution region 826 supplies a sequencing chamber 828. Biolayer 424 of CMOS image sensor 262 is oriented toward sequencing chamber 828. Then sequencing chamber 828 supplies outlet 822. Further, microfluidic cartridge 800 includes certain membrane valves 830 that control the flow of liquid in and out of PCR chamber 824.

Figure 9A:
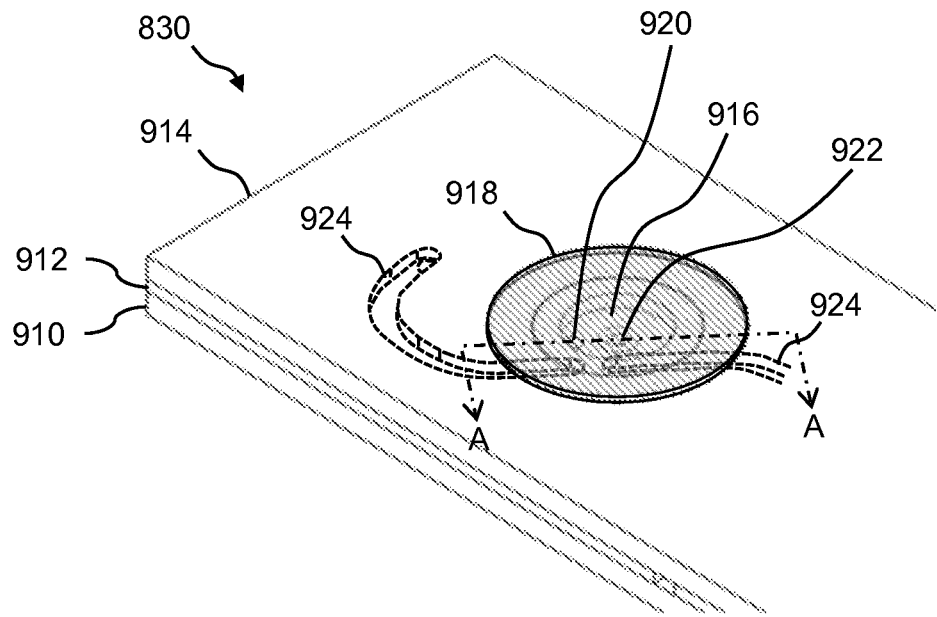
FIGS. 9A and 9B illustrate perspective views of an example of a membrane valve, wherein membrane valves can be integrated into the fluidics layers.
Figure 9B:
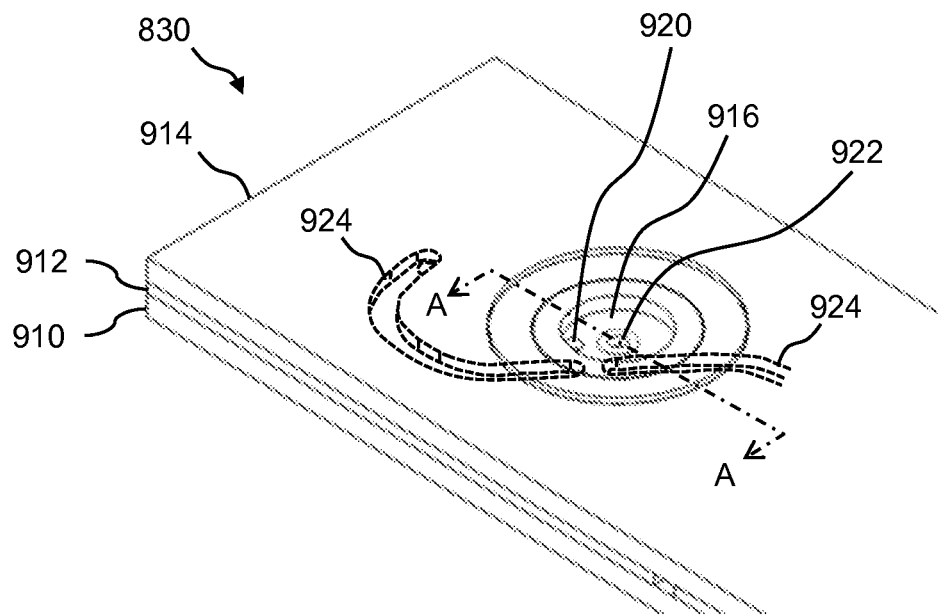

FIGS. 9A and 9B illustrate perspective views of an example of membrane valve 830, wherein membrane valves can be integrated into, for example, fluidics layers 200. Referring now to FIG. 9A is a perspective view of membrane valve 830. In this example, membrane valve 830 includes, in order, a base layer 910, a fluidics channel layer 912, and a reservoir layer 914. Base layer 910, fluidics channel layer 912, and reservoir layer 914 can be formed of, for example, polycarbonate, PMMA, COC, and/or polyimide. Reservoir layer 914 has a recessed region that creates a small reservoir 916 in reservoir layer 914. A membrane layer 918 is stretched across reservoir 916. Reservoir 916 has an inlet 920 and an outlet 922, which provide a flow path to respective fluidics channels 924. In order to better show the features of reservoir 916 as well as inlet 920 and outlet 922, FIG. 9B shows membrane valve 830 without membrane layer 918 covering reservoir 916. Membrane layer 918 is formed of an elastomeric membrane material (e.g., silicone elastomer) that is flexible and stretchable.

Figure 10A:
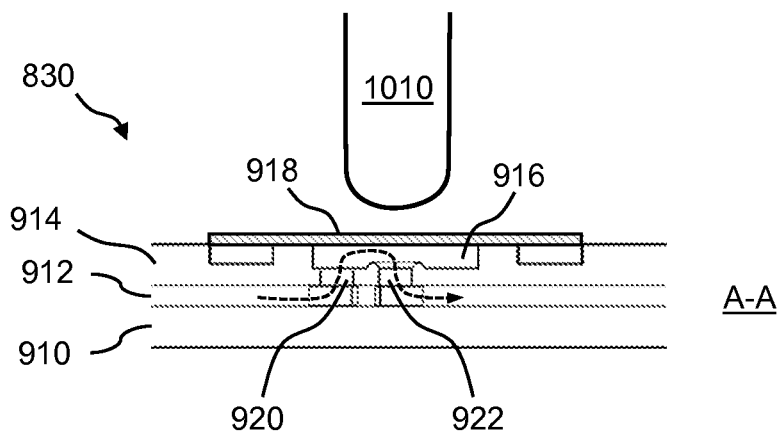
FIGS. 10A and 10B illustrate cross-sectional views of the membrane valve in the open and closed states, respectively.
Figure 10B:
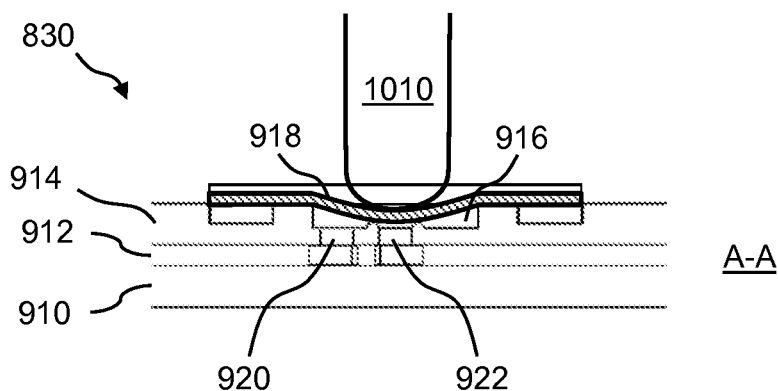

FIGS. 10A and 10B each show a cross-sectional view of membrane valve 830 taken along line A-A of FIG. 9A. An actuator, such as an actuator 1010, can be used to open and close membrane valve 830. For example, FIG. 10A shows membrane valve 830 in the open state in which actuator 1010 is not engaged with membrane layer 918. By contrast, FIG. 10B shows membrane valve 830 in the closed state in which actuator 1010 is engaged with membrane layer 918.

Namely, the tip of actuator 1010 is used to push the center portion of membrane layer 918 against outlet 922 and thereby blocking the flow of liquid therethrough. Membrane valve 830 (i.e., membrane valves 242, 244, and 246) can be actuated using, for example, mechanical or air actuation, such as solenoids or pneumatic pumps.

Figure 11:
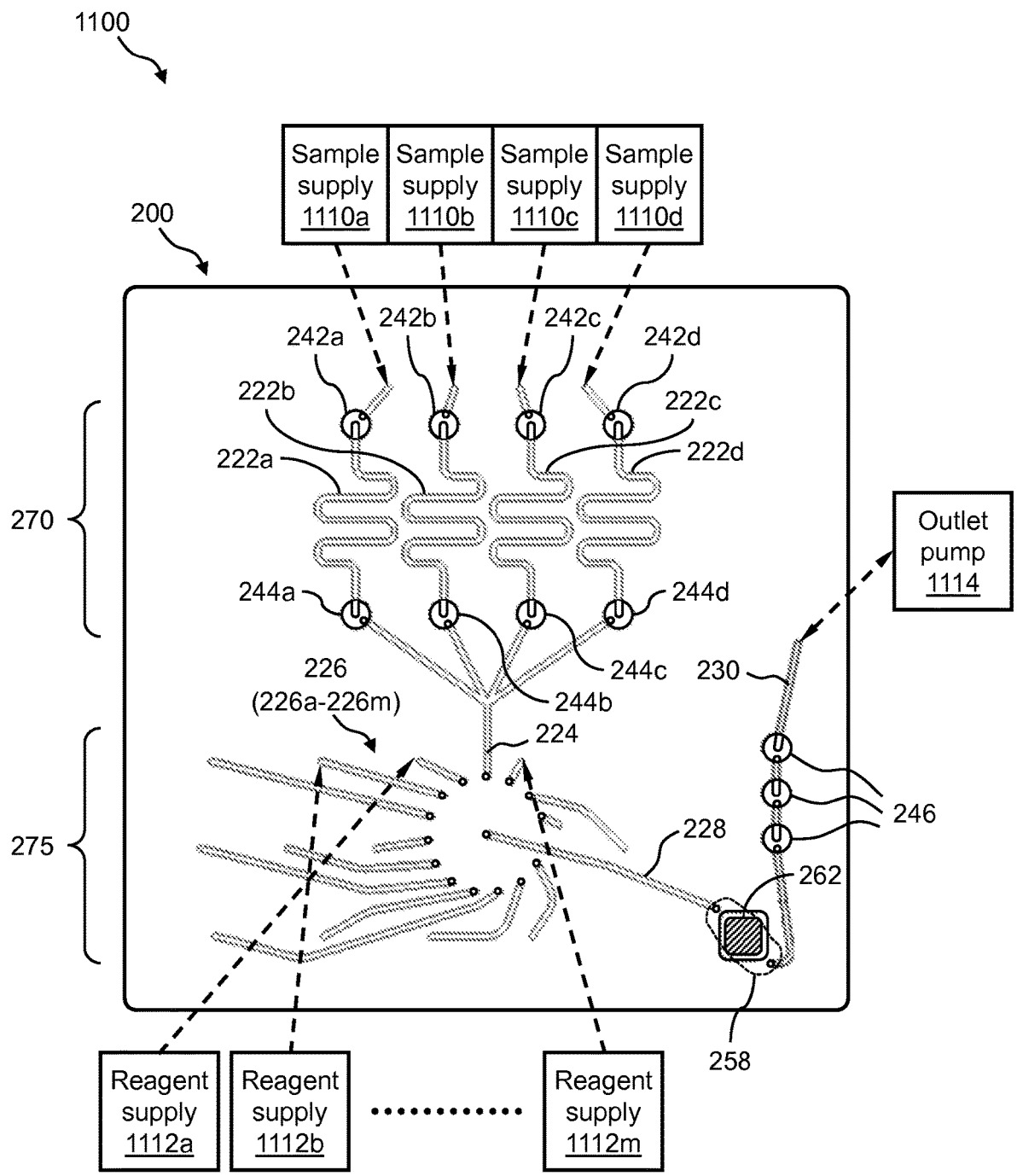
FIG. 11 illustrates a schematic diagram of an example of a microfluidic cartridge that includes both CMOS technology and digital fluidics integrated together.

FIG. 11 illustrates a schematic diagram of an example of a microfluidic cartridge 1100 that includes both CMOS technology and digital fluidics integrated together. Namely, microfluidic cartridge 1100 includes fluidics layers 200 that are fluidly and operatively connected to four sample supplies 1110 (e.g., sample supplies 1110a, 1110b, 1110c, 1110d), thirteen reagent supplies 1112 (e.g., reagent supplies 1112a-1112m), and an outlet pump 1114. Fluidics layers 200 include a PCR region 270 and a reagent mixing and distribution region 275. PCR region 270 includes, for example, four PCR channels 222 (e.g., PCR channels 222a, 222b, 222c, 222d). The inlets of PCR channels 222a, 222b, 222c, and 222d are supplied by sample supplies 1110a, 1110b, 1110c, and 1110d, respectively. Because microfluidic cartridge 1100 includes four PCR channels 222 that are supplied by the four sample supplies 1110, microfluidic cartridge 1100 is configured for 4× sample multiplexing.

The inputs of the four PCR channels 222 are controlled using four membrane valves 242. Namely, the inputs of PCR channels 222a, 222b, 222c, and 222d are controlled using membrane valves 242a, 242b, 242c, and 242d, respectively. Similarly, the outputs of the four PCR channels 222 are controlled using four membrane valves 244. Namely, the outputs of PCR channels 222a, 222b, 222c, and 222d are controlled using membrane valves 244a, 244b, 244c, and 244d, respectively. The outputs of the four PCR channels 222 supply a common PCR output channel 224, which then supplies reagent mixing and distribution region 275. The presence of membrane valves 242 and membrane valves 244 in fluidics layers 200 allow PCR region 270 to be completely sealed off.

Reagent mixing and distribution region 275 includes an arrangement of thirteen reagent channels 226 (e.g., reagent channels 226a-226m). Further, the thirteen reagent channels 226a-226m are supplied via the thirteen reagent supplies 1112a-1112m, respectively. A rotary valve assembly (not shown) is used to fluidly connect a certain PCR channel 222 to a certain reagent supply 1112. In so doing, a certain PCR Mix can be created. The rotary valve assembly (not shown) is also used to fluidly connect a certain PCR Mix to a sequencing feed channel 228, which supplies an inlet of a sequencing chamber 258. Further, CMOS image sensor 262 is positioned at sequencing chamber 258.

A sequencing outlet channel 230 is provided at the outlet of sequencing chamber 258. An outlet pump 1114 is fluidly and operatively connected to sequencing outlet channel 230. Outlet pump 1114 is used to provide positive or negative pressure in order to move liquid in any direction along the flow paths of fluidics layers 200. Further, a series of three membrane valves 246 are provided along the length of sequencing outlet channel 230. Membrane valves 242, 244, and 246 can be implemented according to membrane valve 830 that is shown and described in FIGS. 9A, 9B, 10A, and 10C.

The three membrane valves 246 at sequencing outlet channel 230 can be used as pumps in place of or in combination with outlet pump 1114. Therefore, in one embodiment, microfluidic cartridge 1100 includes outlet pump 1114 only and the three membrane valves 246 are omitted. In another embodiment, microfluidic cartridge 1100 includes the three membrane valves 246 only and outlet pump 1114 is omitted. In yet another embodiment, microfluidic cartridge 1100 includes both outlet pump 1114 and the three membrane valves 246. In still another embodiment, microfluidic cartridge 1100 includes any other type of pumping mechanism in place of outlet pump 1114 and/or the three membrane valves 246. More details of an example of implementing microfluidic cartridge 1100 are shown and described herein below with reference to FIGS. 12 through 47B.

Figure 12:
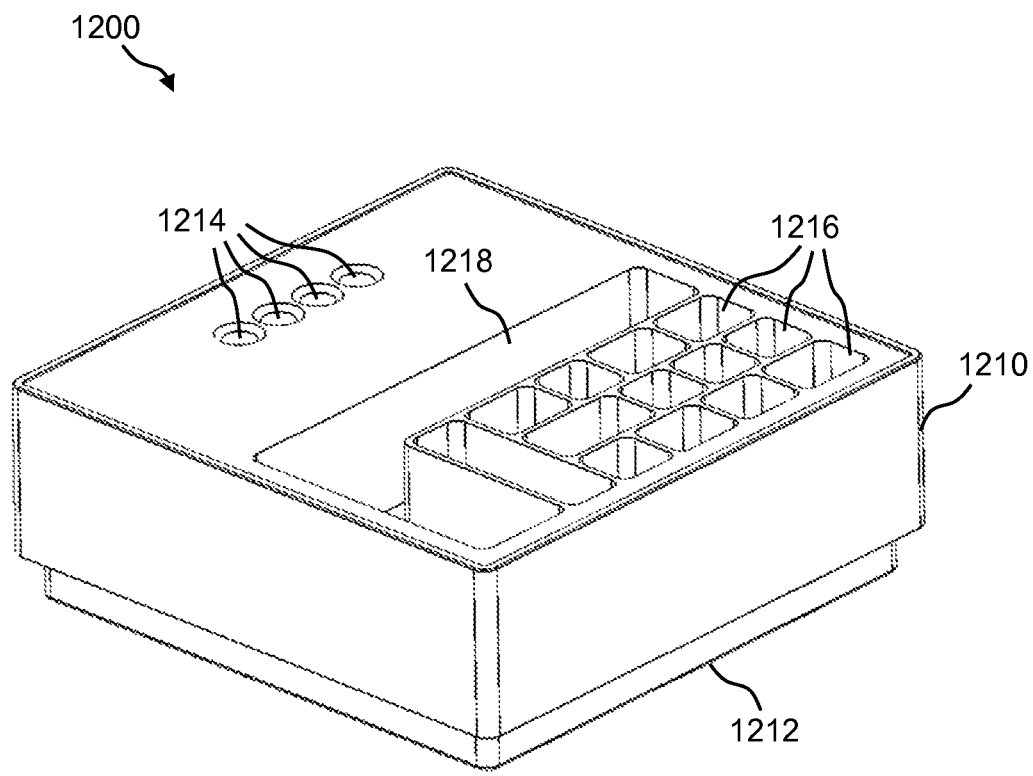
FIGS. 12 and 13 illustrate perspective views of a microfluidic cartridge assembly, which is one example of the physical instantiation of the integrated microfluidic cartridge shown in FIG. 11.
Figure 13:
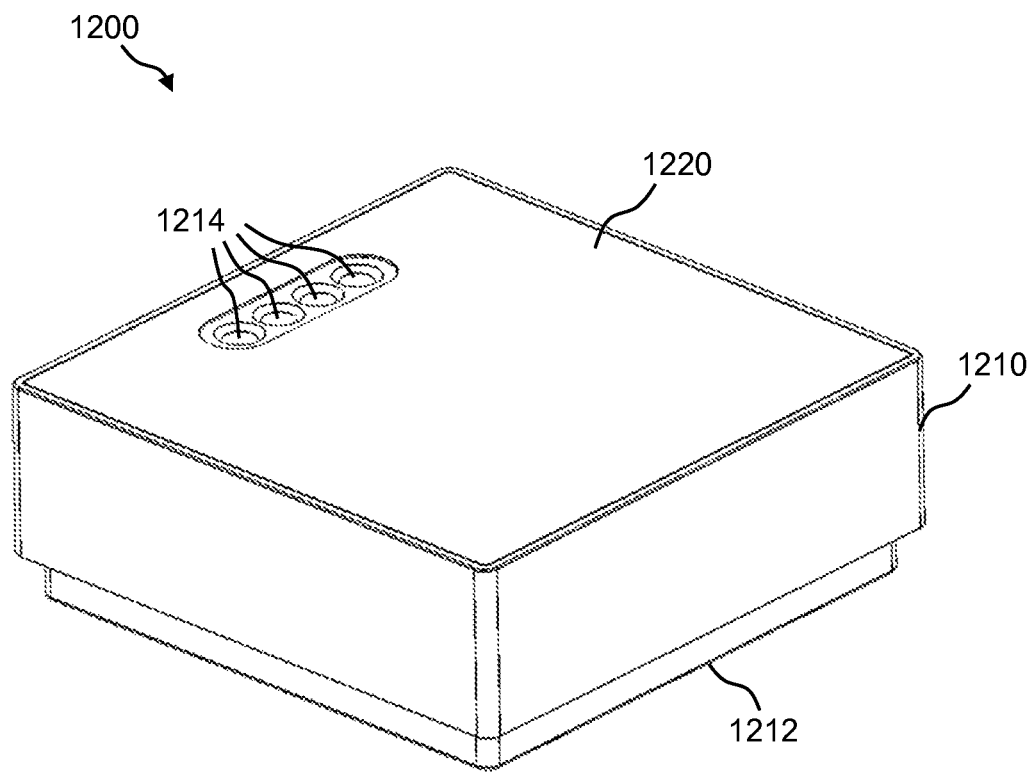

FIGS. 12 and 13 illustrate perspective views of a microfluidic cartridge assembly 1200, which is one example of the physical instantiation of the integrated microfluidic cartridge 1100 shown in FIG. 11. Microfluidic cartridge assembly 1200 is an example of conventional injection molded fluidics that is integrated with flexible PCB technology. In this example, microfluidic cartridge assembly 1200 is a multi-compartment microfluidic cartridge that includes a housing 1210 fastened atop a base plate 1212. Housing 1210 and base plate 1212 can be formed, for example, of molded plastic and fastened together via screws (see FIG. 19). The overall height of microfluidic cartridge assembly 1200 can be, for example, from about 12 mm to about 100 mm. The overall length of microfluidic cartridge assembly 1200 can be, for example, from about 100 mm to about 200 mm. The overall width of microfluidic cartridge assembly 1200 can be, for example, from about 100 mm to about 200 mm.

Figure 14A:
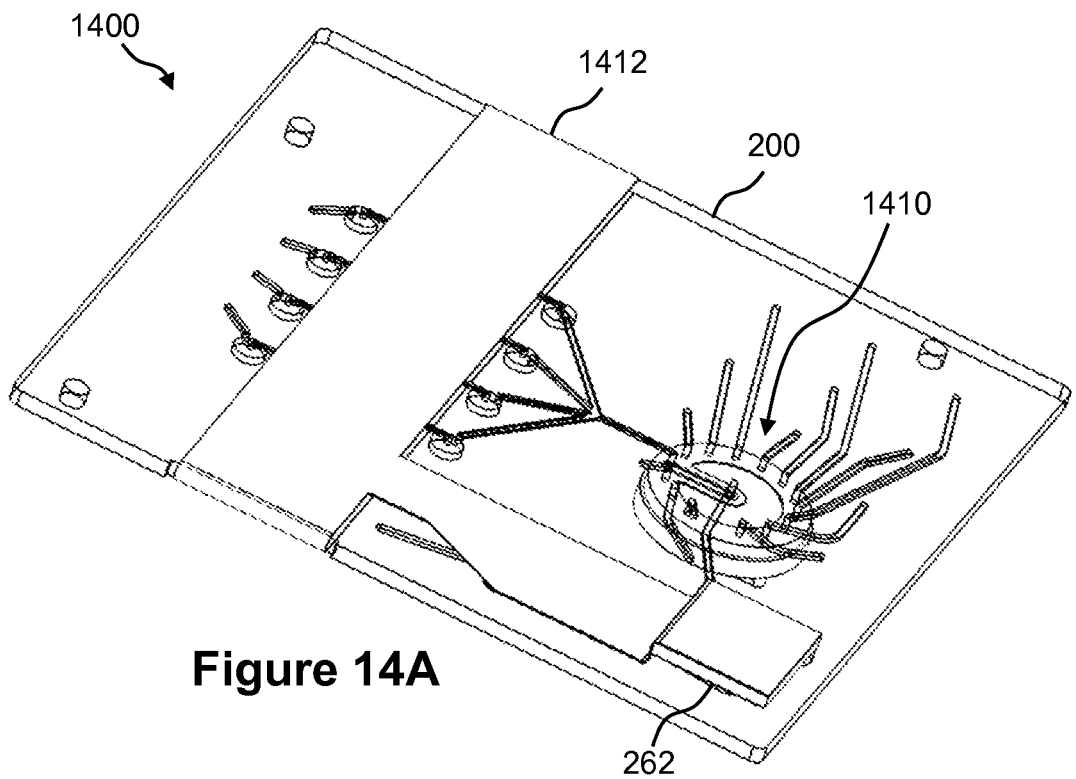
FIGS. 14A and 14B illustrate perspective views of an example of a fluidics assembly that is installed in the microfluidic cartridge assembly shown in FIGS. 12 and 13.
Figure 14B:
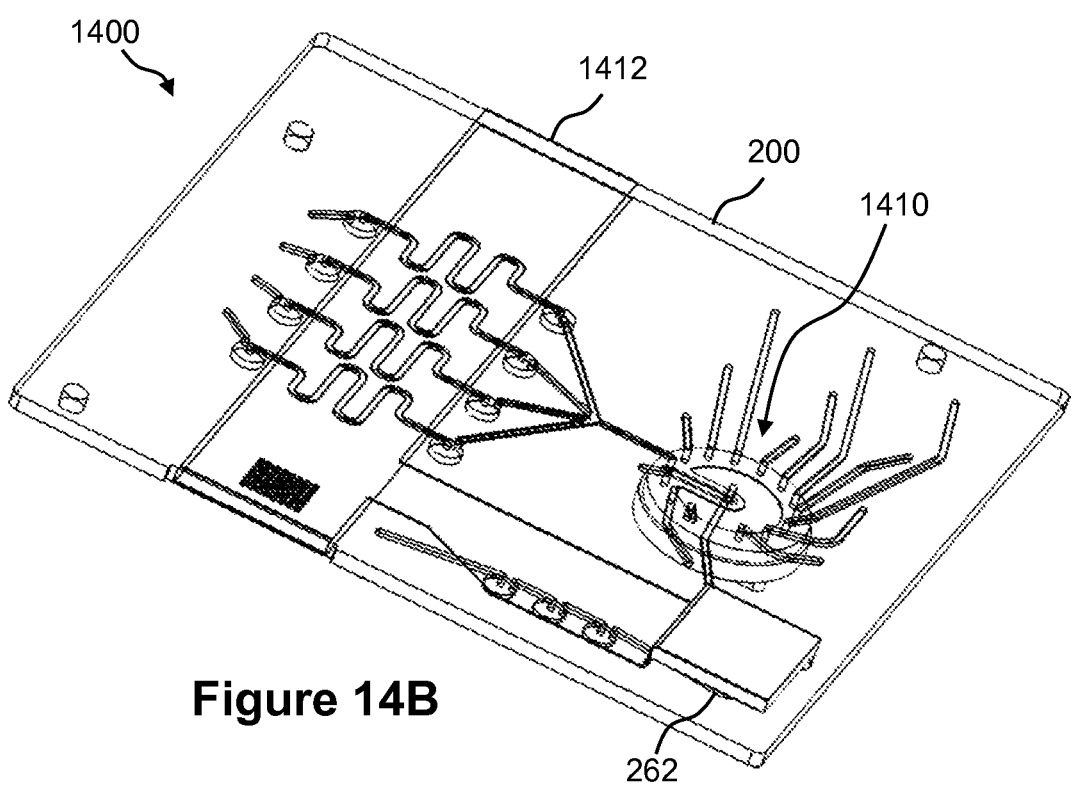

Inside of housing 1210 is a fluidics assembly 1400, which is shown in FIGS. 14A and 14B. Namely, FIGS. 14A and 14B illustrate perspective views of an example of fluidics assembly 1400, which is installed in microfluidic cartridge assembly 1200 shown in FIGS. 12 and 13. Fluidics assembly 1400 is based on the integrated microfluidic cartridge 1100 shown in FIG. 11. Namely, fluidics assembly 1400 includes fluidics layers 200 that is shown and described in FIGS. 2 and 11. Fluidics assembly 1400 also includes a rotary valve assembly 1410 that is arranged with respect to the thirteen reagent channels 226a-226m in reagent mixing and distribution region 275 of fluidics layers 200. The length of fluidics layers 200 can be, for example, from about 100 mm to about 200 mm. The width of fluidics layers 200 can be, for example, from about 100 mm to about 200 mm.

Further, fluidics assembly 1400 includes a flexible PCB heater 1412 that wraps around both sides of PCR region 270 of fluidics layers 200. Two individually controlled heater traces are provided in flexible PCB heater 1412 such that there is one heater trace on one side of PCR region 270 and another heater trace on the other side of PCR region 270. Flexible PCB heater 1412 is an example of the flexible PCB heater 818 of microfluidic cartridge 800 shown in FIG. 8. More details of an example of a heater tracer are shown and described herein below with reference to FIGS. 15A and 15B. More details of an example of flexible PCB heater 1412 are shown and described herein below with reference to FIGS. 41A, 41B, and 41C.

Referring now again to FIGS. 12 and 13, housing 1210 of microfluidic cartridge assembly 1200 also includes four sample loading ports 1214 (e.g., sample loading ports 1214a, 1214b, 1214c, 1214d) that substantially align with inputs of the four PCR channels 222 (e.g., PCR channels 222a, 222b, 222c, 222d) of fluidics layers 200. Housing 1210 of microfluidic cartridge assembly 1200 also includes thirteen reagent reservoirs 1216 that supply the thirteen reagent channels 226 (e.g., reagent channels 226a-226m) of fluidics layers 200. The thirteen reagent reservoirs 1216 can be the same size or different. For example, the reagent reservoirs 1216 can hold volumes of liquid ranging from about 0.001 ml to about 0.150 ml.

Housing 1210 of microfluidic cartridge assembly 1200 also includes a waste reservoir 1218 that is supplied by sequencing outlet channel 230. Waste reservoir 1218 can hold a volume of liquid ranging, for example, from about 25 ml to about 100 ml. FIG. 13 shows that reagent reservoirs 1216 and waste reservoir 1218 may be covered and sealed with, for example, a foil seal 1220.

Figure 15A:
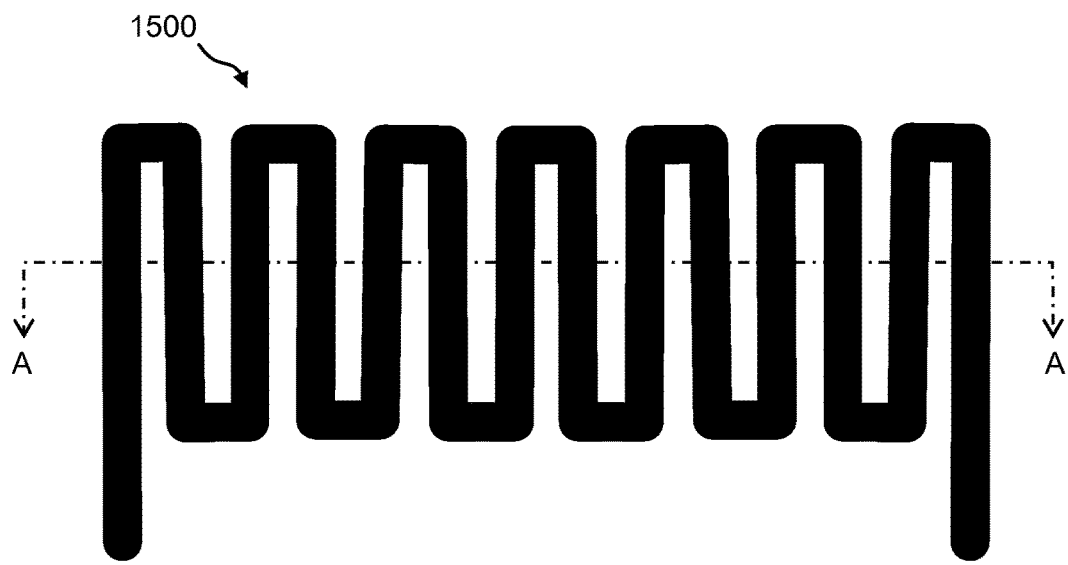
FIGS. 15A and 15B illustrate a plan view and a cross-sectional view, respectively, of an example of a heater trace that can be installed in the fluidics assembly shown in FIGS. 14A and 14B.
Figure 15B:
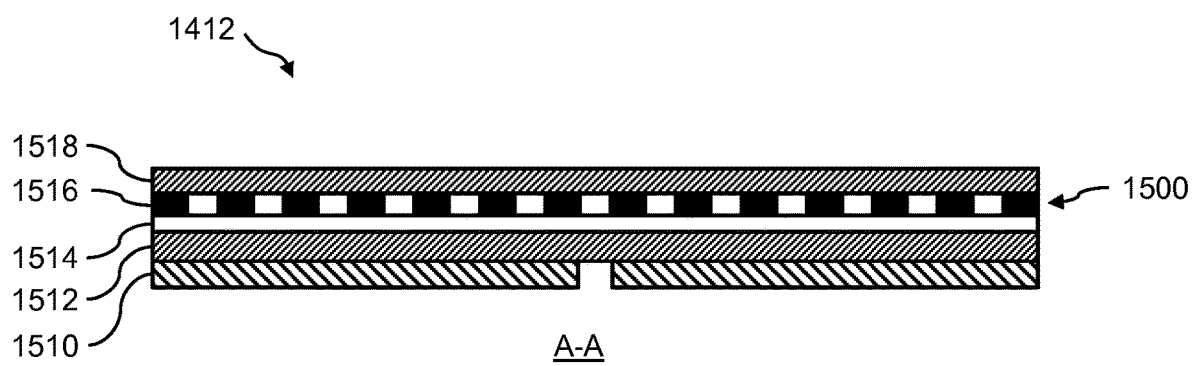

FIGS. 15A and 15B illustrate a plan view and a cross-sectional view, respectively, of an example of a heater trace 1500 that can be installed in fluidics assembly 1400 shown in FIGS. 14A and 14B. Namely, FIG. 15A shows a plan view of an example of heater trace 1500, which is has a serpentine type of layout. FIG. 15B shows a cross-sectional view of one side of flexible PCB heater 1412 of fluidics assembly 1400, which includes heater trace 1500. Flexible PCB heater 1412 is a multilayer structure that includes, for example, in order, a single-sided flexible copper layer 1510, an adhesive layer 1512, a dielectric layer 1514, a copper heater layer 1516 in which heater trace 1500 is patterned, and a Kapton® layer 1518. Copper heater layer 1516 shows the cross-section of heater trace 1500 taken along the line A-A of FIG. 15A.

Figure 16:
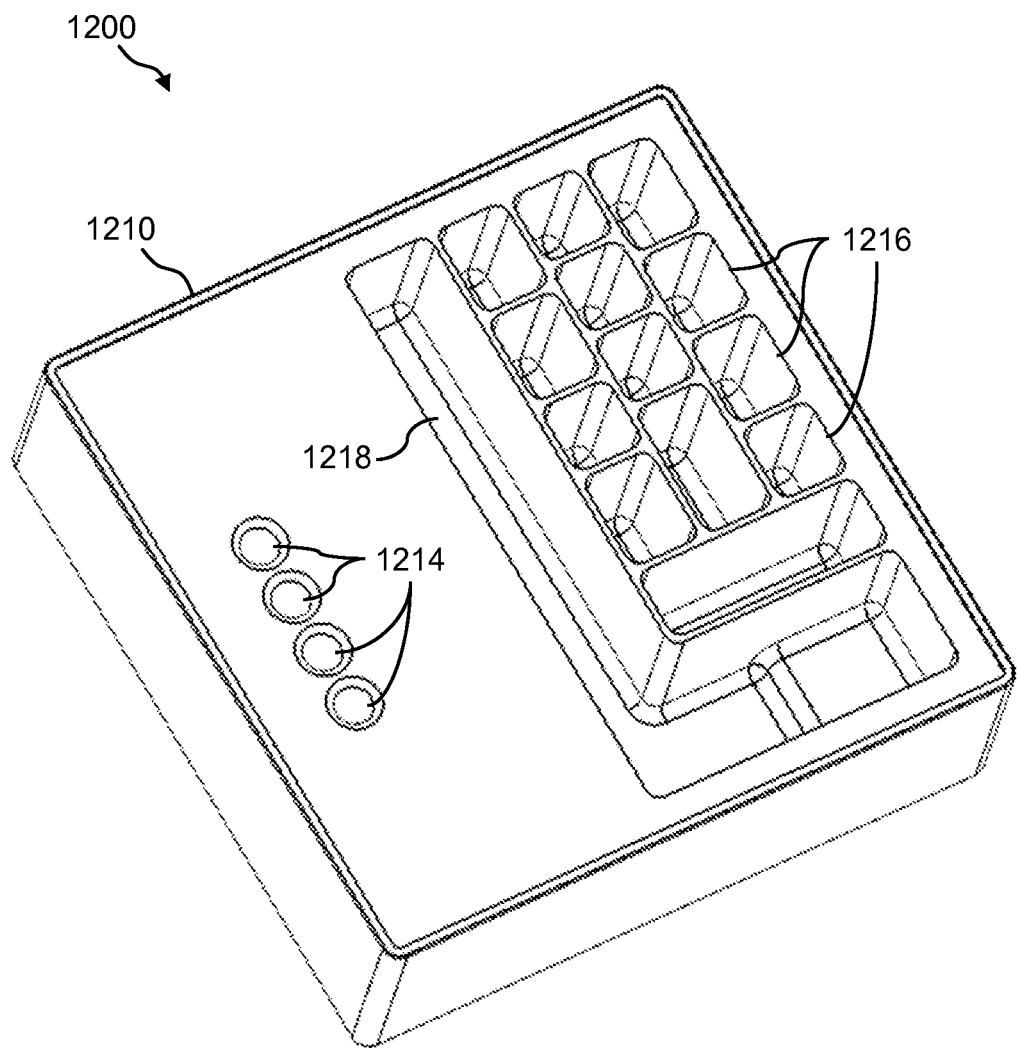
FIGS. 16, 17, 18, 19, 20A and 20B illustrate various other views of the microfluidic cartridge assembly of FIG. 12, showing more details thereof.
Figure 17:
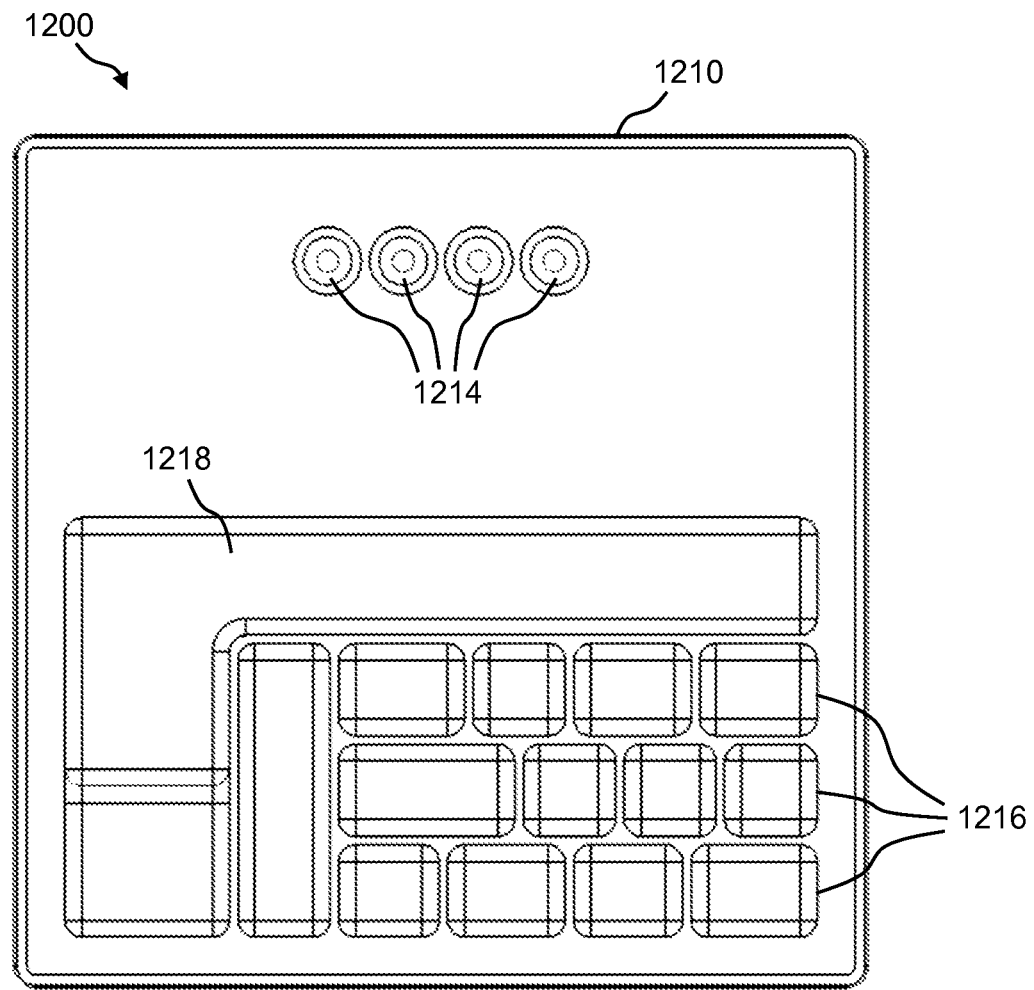
Figure 18:
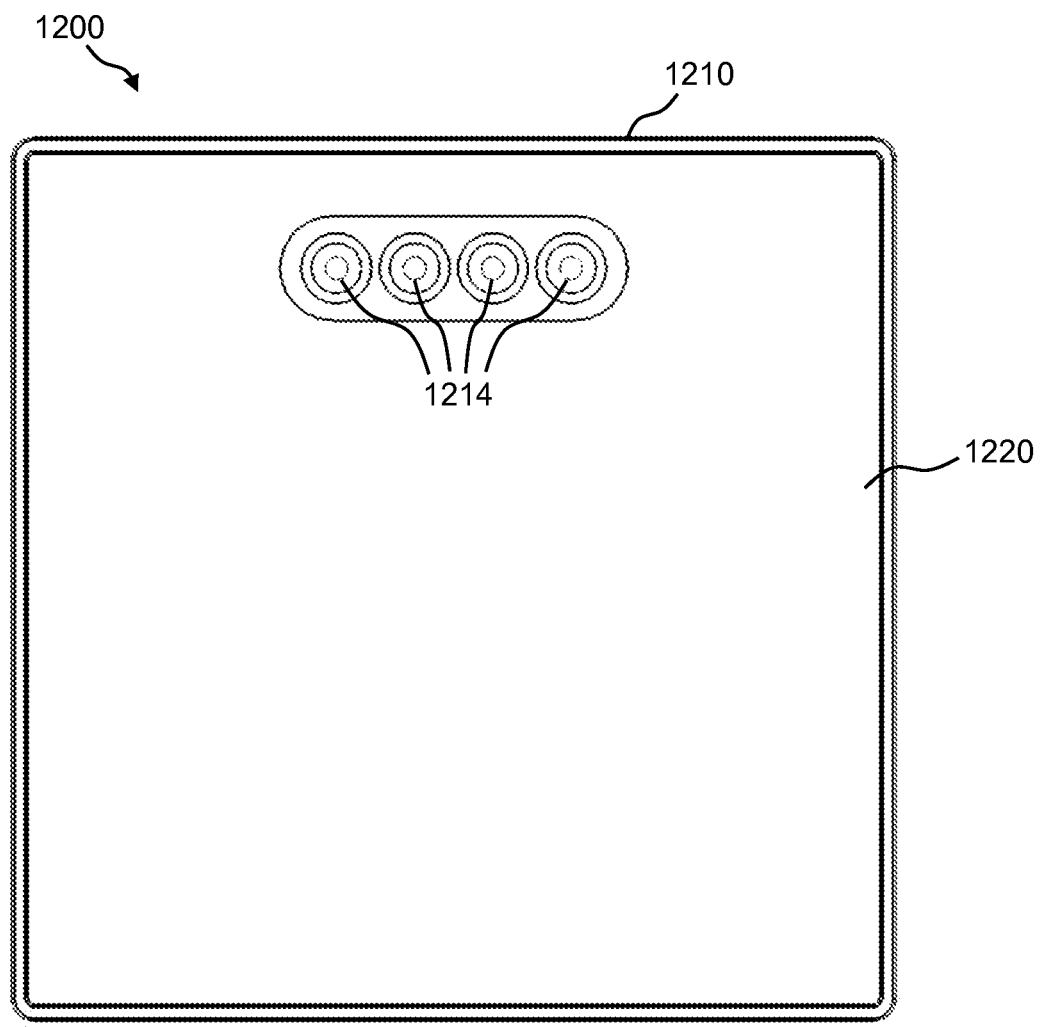

FIGS. 16, 17, 18, 19, 20A and 20B illustrate various other views of microfluidic cartridge assembly 1200 of FIG. 12, showing more details thereof. Namely, FIG. 16 shows a perspective view and FIG. 17 shows a plan view of the housing 1210-side of microfluidic cartridge assembly 1200, both showing more details of the configuration of the thirteen reagent reservoirs 1216 and waste reservoir 1218. FIG. 18 shows a plan view of the housing 1210-side of microfluidic cartridge assembly 1200 with the foil seal 1220 installed. Foil seal 1220 has an opening so that the four sample loading ports 1214 remain exposed and accessible.

Figure 19:
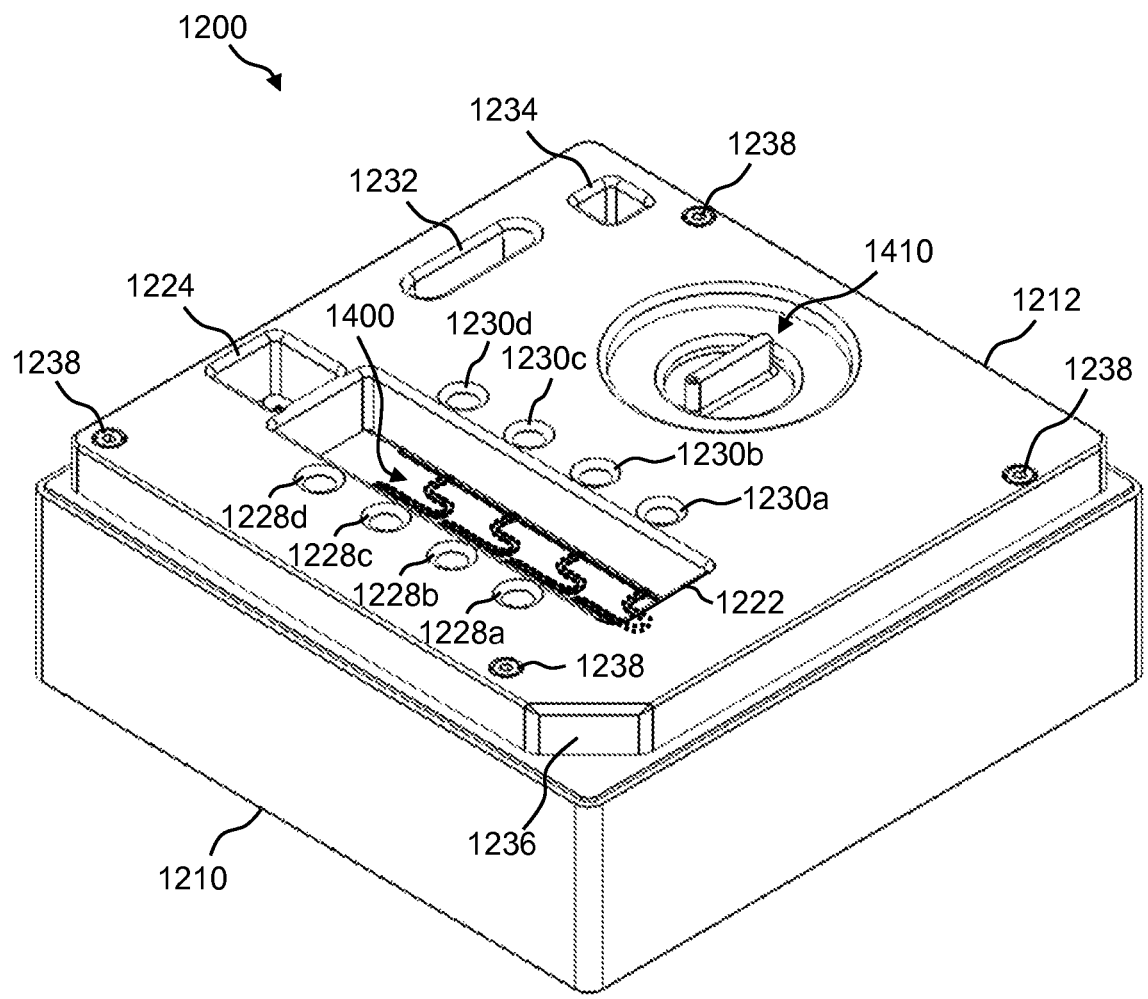
Figure 20A:
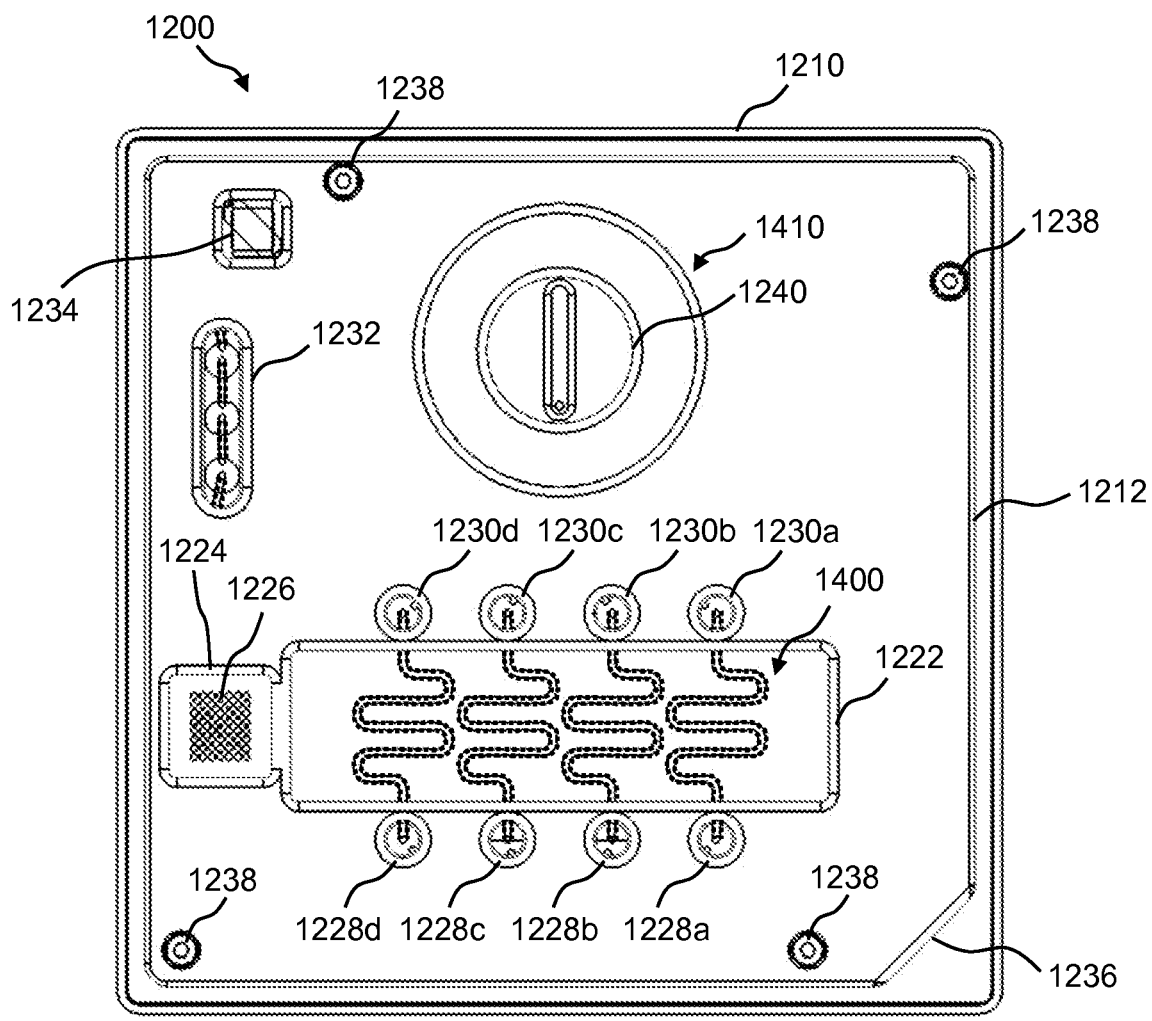
Figure 20B:
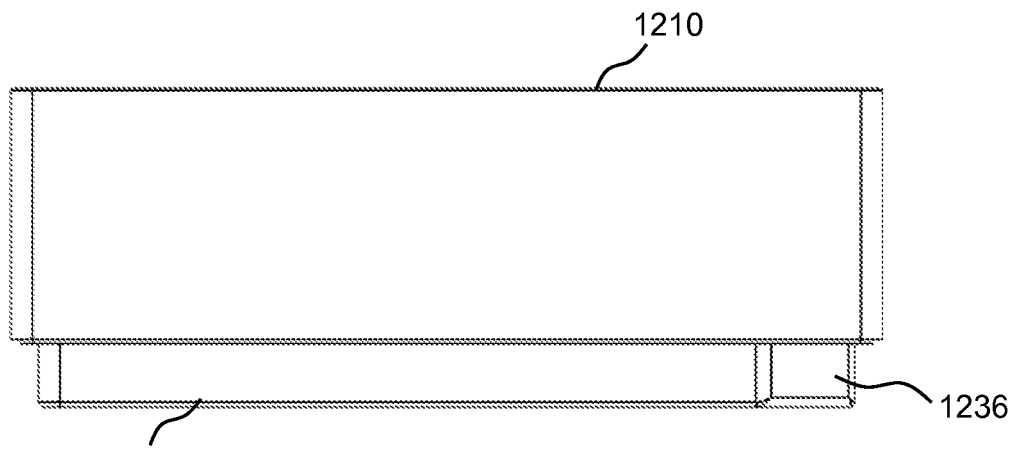

FIG. 19 shows a perspective view of the base plate 1212-side of microfluidic cartridge assembly 1200. FIG. 20A shows a plan view of the base plate 1212-side of microfluidic cartridge assembly 1200. FIG. 20B shows a side view of microfluidic cartridge assembly 1200. FIGS. 19, 20A, and 20B show more details of base plate 1212. Namely, base plate 1212 includes an opening 1222 and an opening 1224 for revealing portions of PCR region 270 of fluidics layers 200 of fluidics assembly 1400. Shown through opening 1224 is a set of I/O pads 1226 for contacting flexible PCB heater 1412 of fluidics assembly 1400.

Along one edge of opening 1222 are four openings 1228 for accessing and actuating the four membrane valves 242 of fluidics layers 200 of fluidics assembly 1400. Namely, opening 1228a substantially aligns with membrane valve 242a. Opening 1228b substantially aligns with membrane valve 242b. Opening 1228c substantially aligns with membrane valve 242c. Opening 1228d substantially aligns with membrane valve 242d.

Along the opposite edge of opening 1222 are four openings 1230 for accessing and actuating the four membrane valves 244 of fluidics layers 200 of fluidics assembly 1400. Namely, opening 1230a substantially aligns with membrane valve 244a. Opening 1230b substantially aligns with membrane valve 244b. Opening 1230c substantially aligns with membrane valve 244c. Opening 1230d substantially aligns with membrane valve 244d.

Additionally, base plate 1212 includes an opening 1232 for accessing and actuating the membrane valves 246 of fluidics layers 200 of fluidics assembly 1400. Base plate 1212 also includes an opening 1234 at sequencing chamber 258. One corner of base plate 1212 has a bevel 1236, which is used for orienting microfluidic cartridge assembly 1200 in, for example, the instrument deck of a microfluidics system (not shown). FIGS. 19 and 20A also show four screws 1238 that are used to fasten base plate 1212 to housing 1210. Further, rotary valve assembly 1410 is shown with respect to reagent mixing and distribution region 275 of fluidics layers 200 of fluidics assembly 1400. Rotary valve assembly 1410 includes a knob that has a grip portion 1240 by which a user or an apparatus may turn a flow controller portion 1242 (see FIG. 22).

Figure 21:
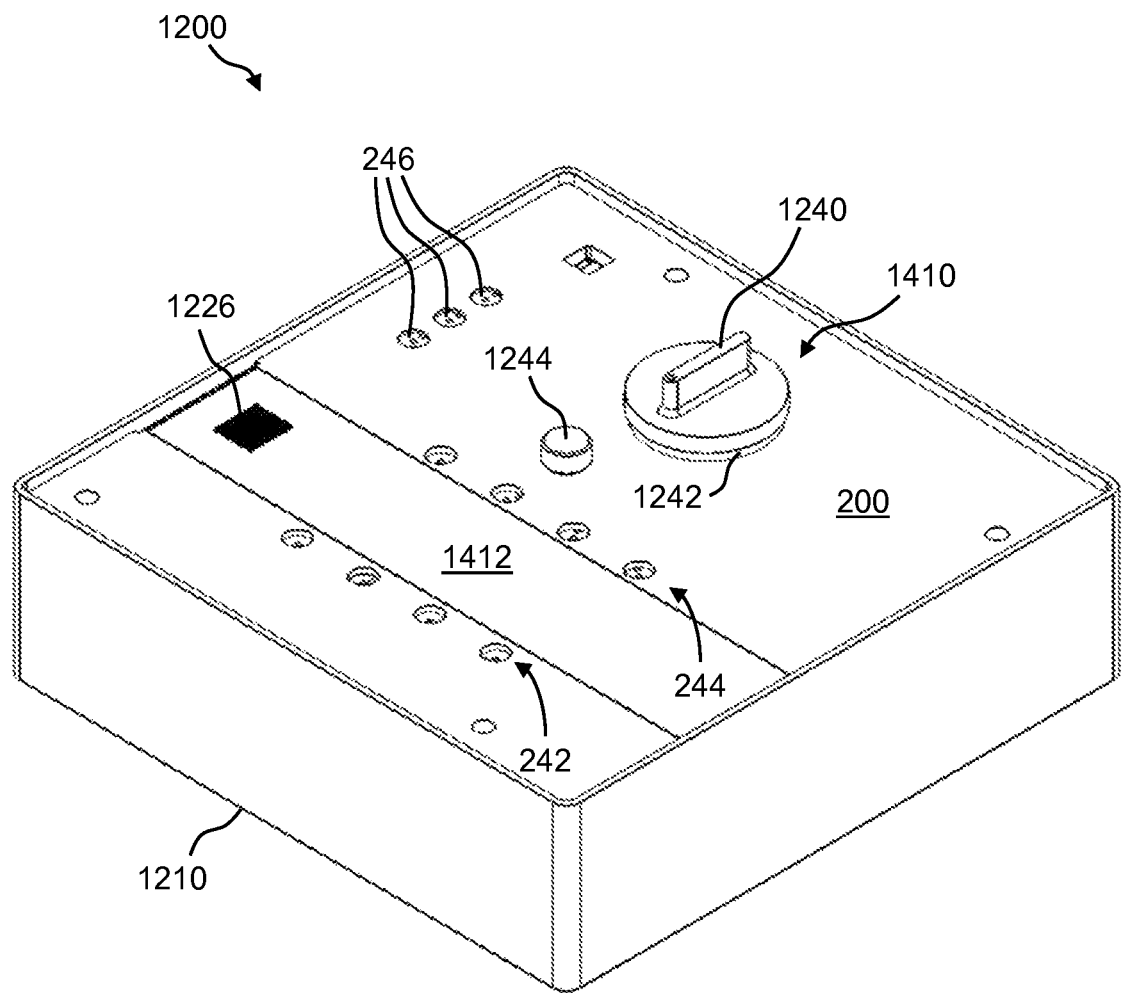
FIGS. 21 through 29 illustrate a process of deconstructing of the microfluidic cartridge assembly of FIG. 12 as a means to reveal the interior components thereof.

Starting with microfluidic cartridge assembly 1200 oriented base plate 1212-side up, FIGS. 21 through 29 essentially show a step-by-step deconstruction of microfluidic cartridge assembly 1200 as a means to reveal the placement and installation of the interior components thereof. First, FIG. 21 shows microfluidic cartridge assembly 1200 with base plate 1212 removed in order to reveal fluidics assembly 1400. In so doing, the flexible PCB layer 260-side of fluidics layers 200 is visible. Further, one side of flexible PCB heater 1412 is visible. Also revealed is a spacer 1244 between fluidics layers 200 and base plate 1212. In FIG. 21, membrane valves 242, 244, and 246 are visible.

Figure 22:
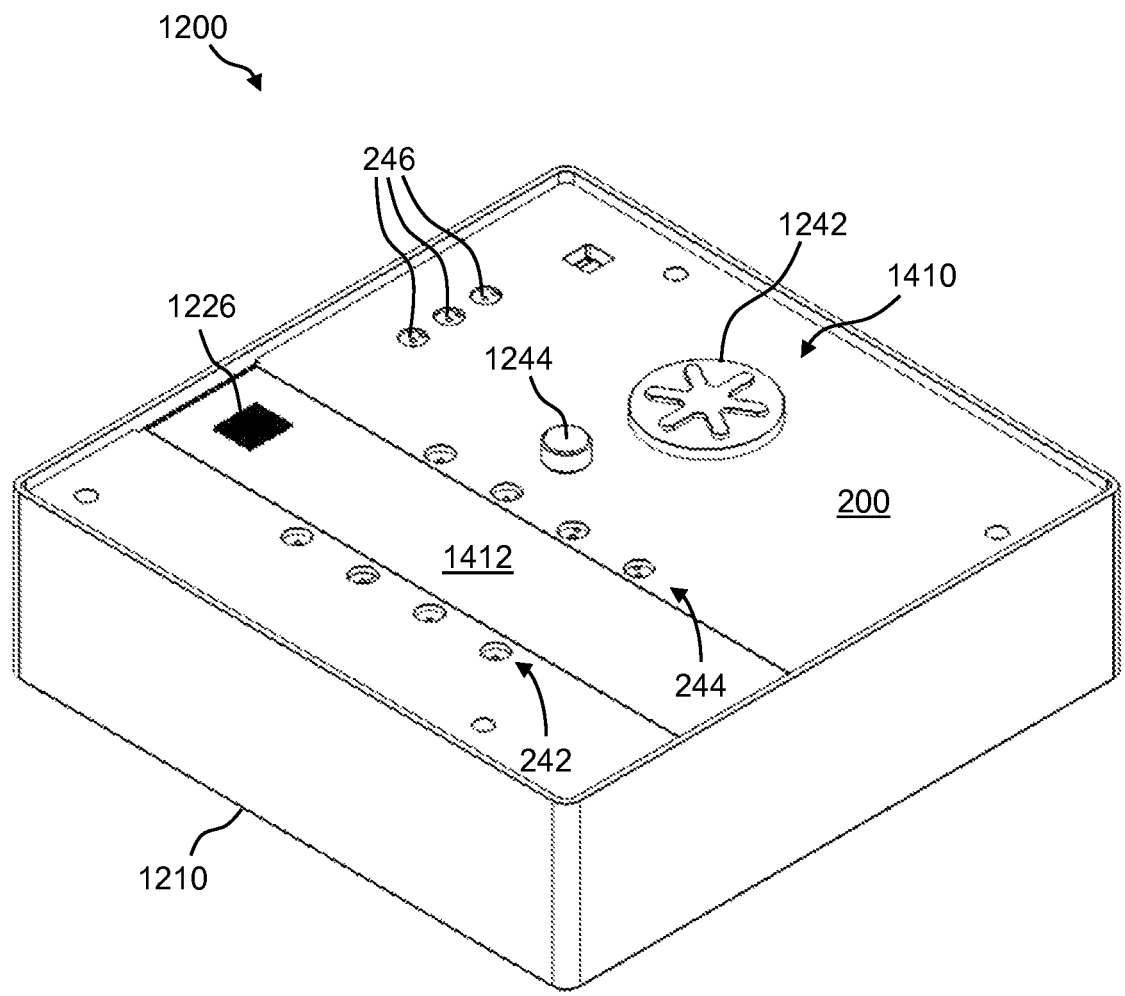

Referring now to FIG. 22, grip portion 1240 of rotary valve assembly 1410 has been removed so that flow controller portion 1242 is now visible. The underside (not shown) of grip portion 1240 is designed to engage with flow controller portion 1242 so that flow controller portion 1242 can be rotated to direct the flow of liquid through one of the thirteen reagent channels 226.

Figure 23:
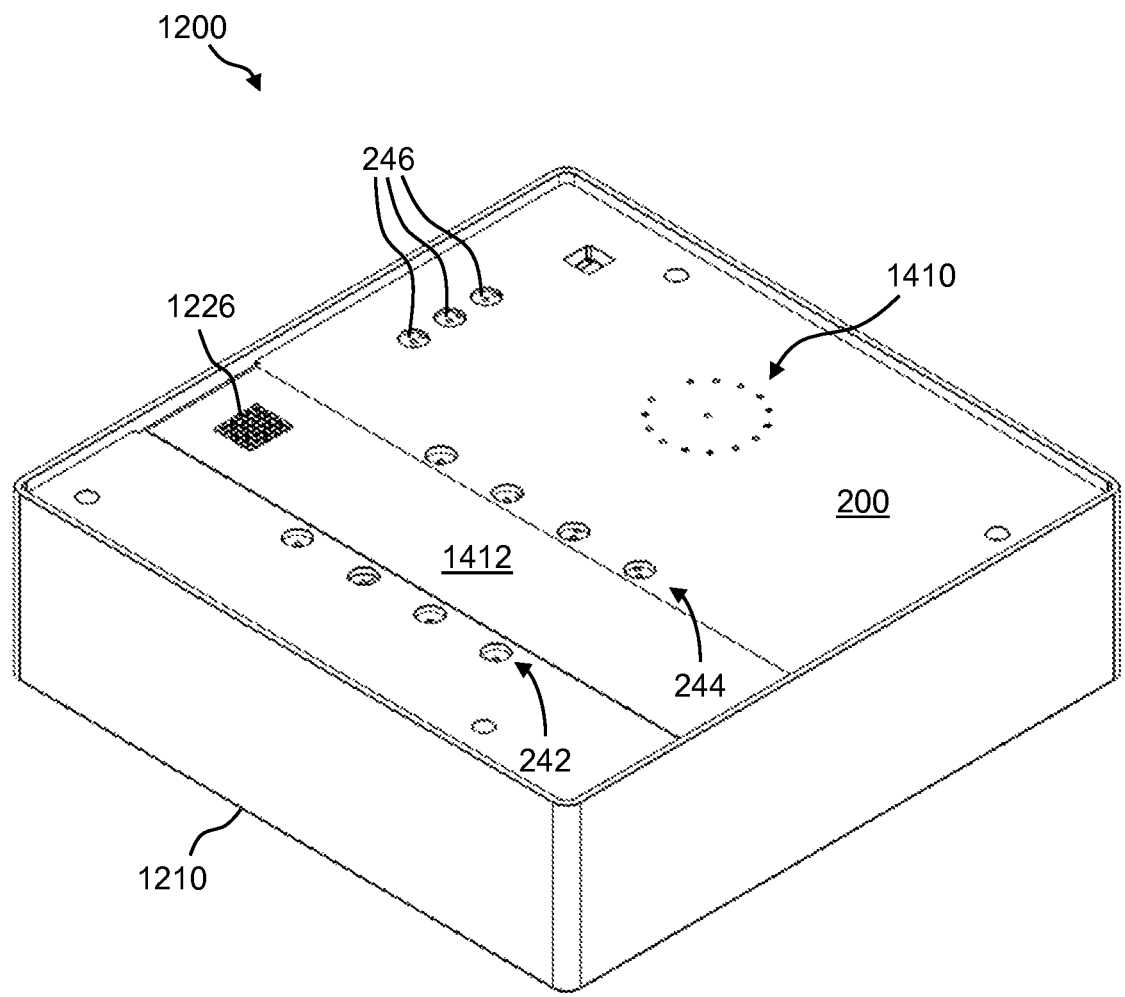

Referring now to FIG. 23, flow controller portion 1242 of rotary valve assembly 1410 has been removed so that the fluid paths associated with PCR output channel 224, reagent channels 226, and sequencing feed channel 228 of fluidics layers 200 are visible.

Figure 24:
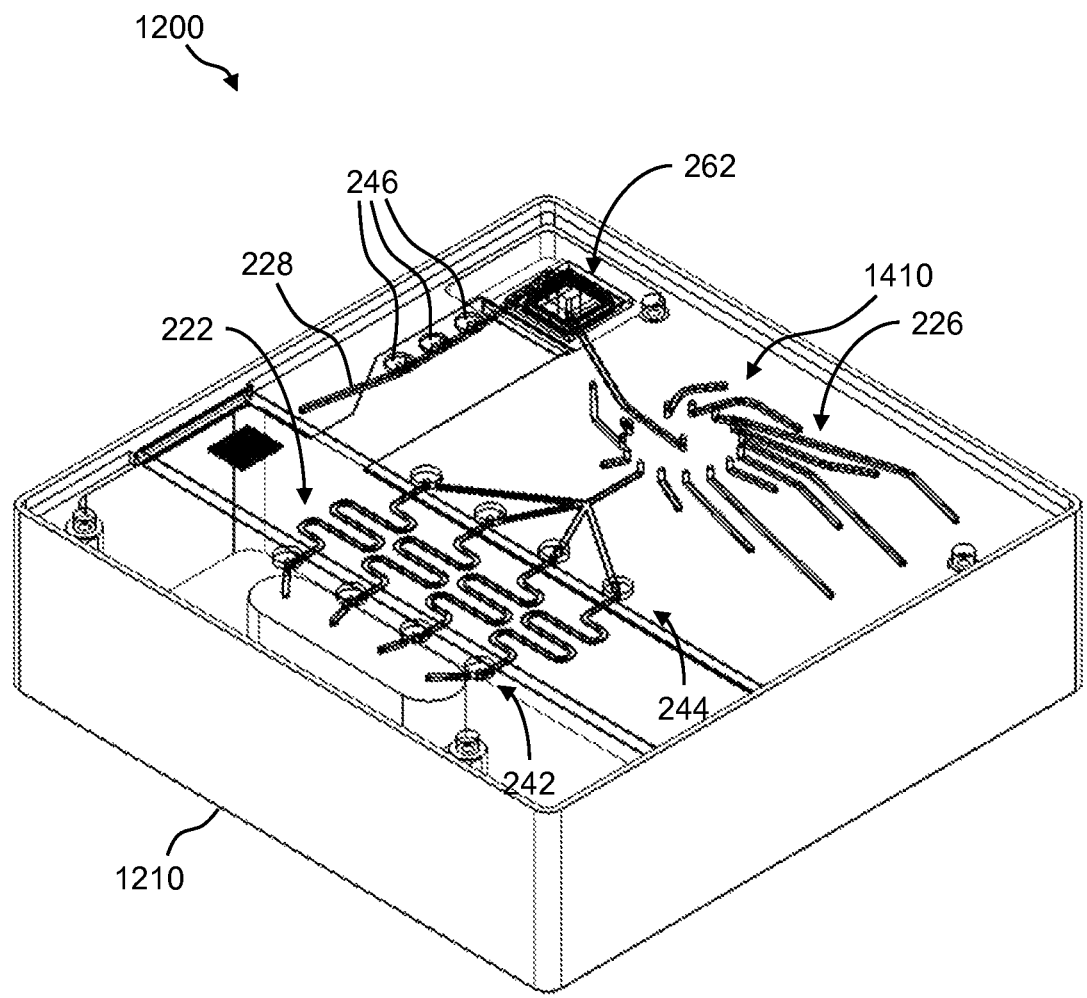

Referring now to FIG. 24, fluidics layers 200 are shown with transparency so that the fluid paths are visible within microfluidic cartridge assembly 1200.

Figure 25:
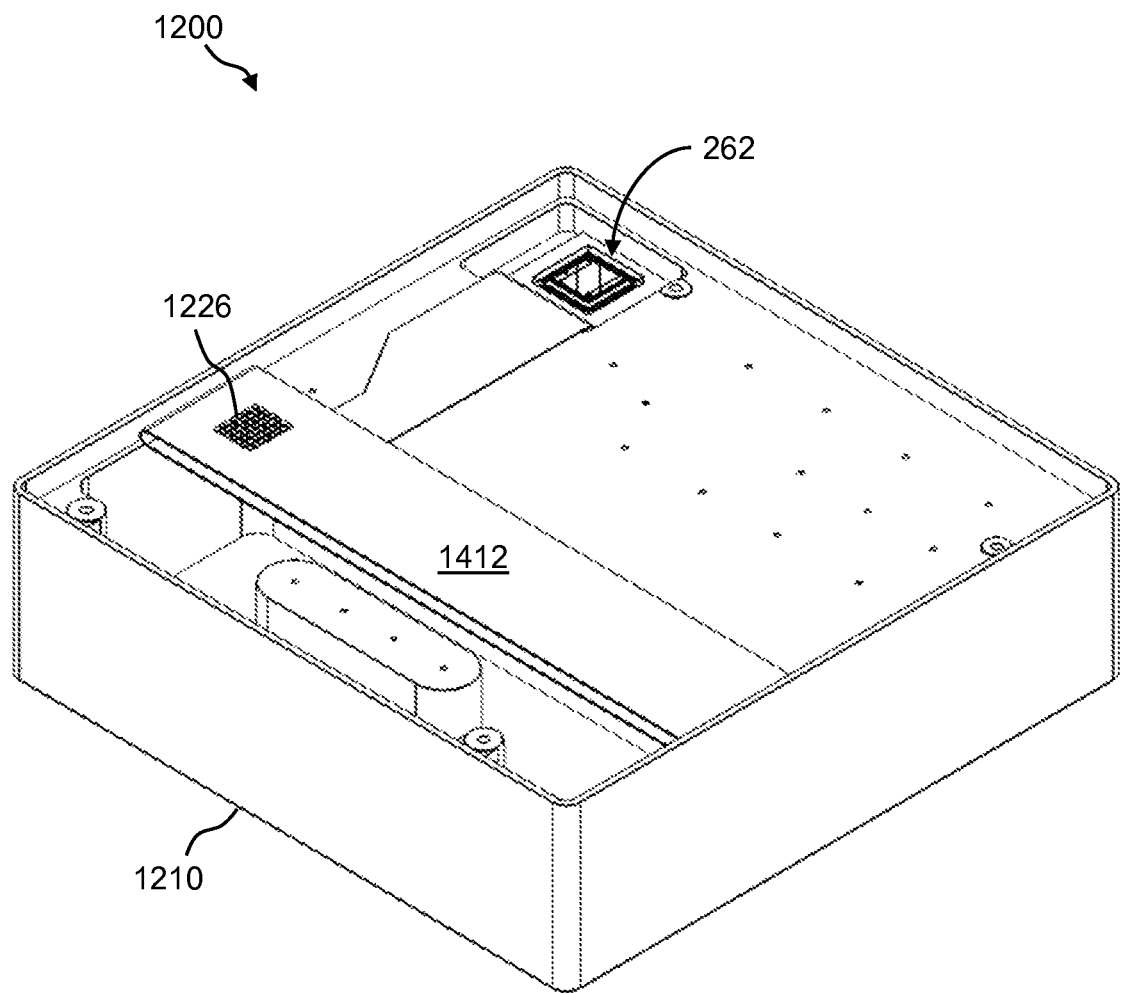
Figure 26:
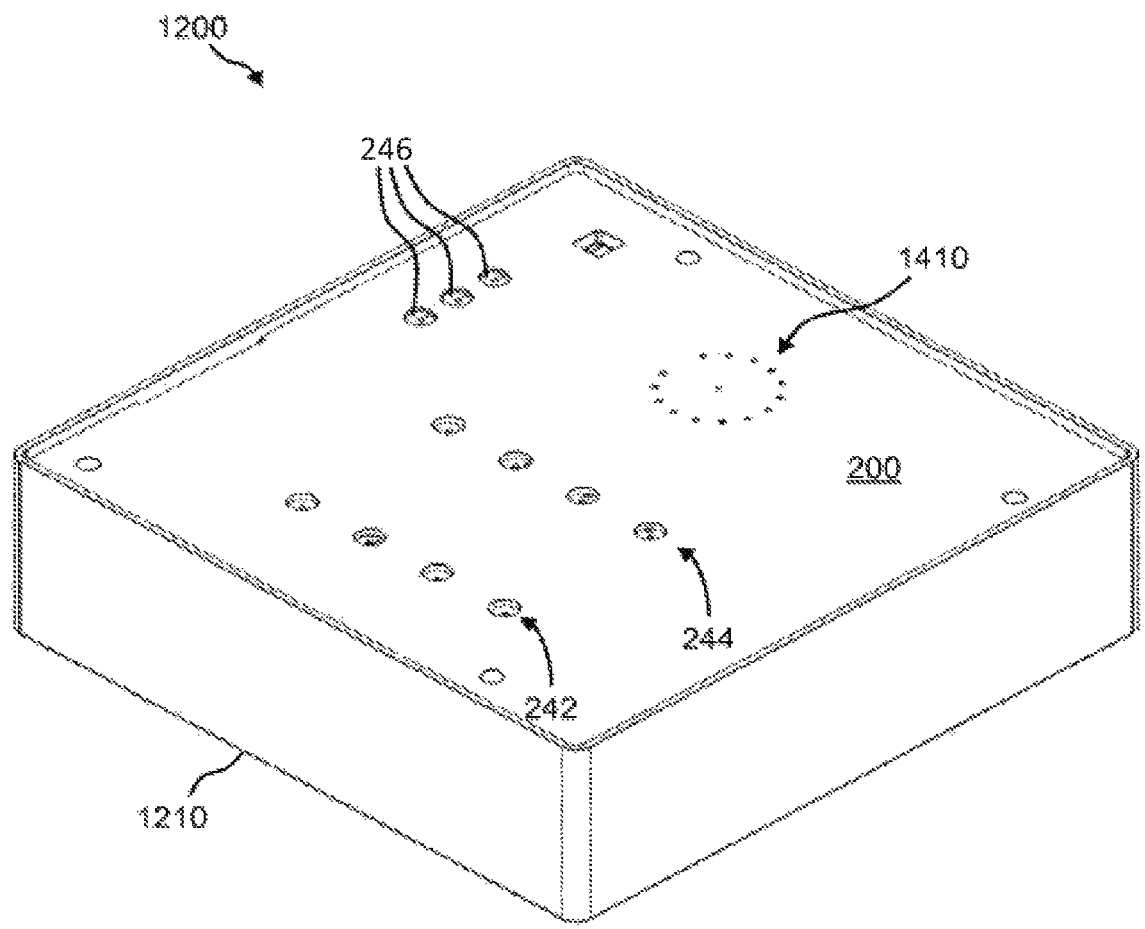

Referring now to FIG. 25, fluidics layers 200 has been removed and flexible PCB heater 1412 is shown alone within housing 1210. Referring now to FIG. 26, flexible PCB heater 1412 has been removed and fluidics layers 200 is shown alone within housing 1210.

Figure 27:
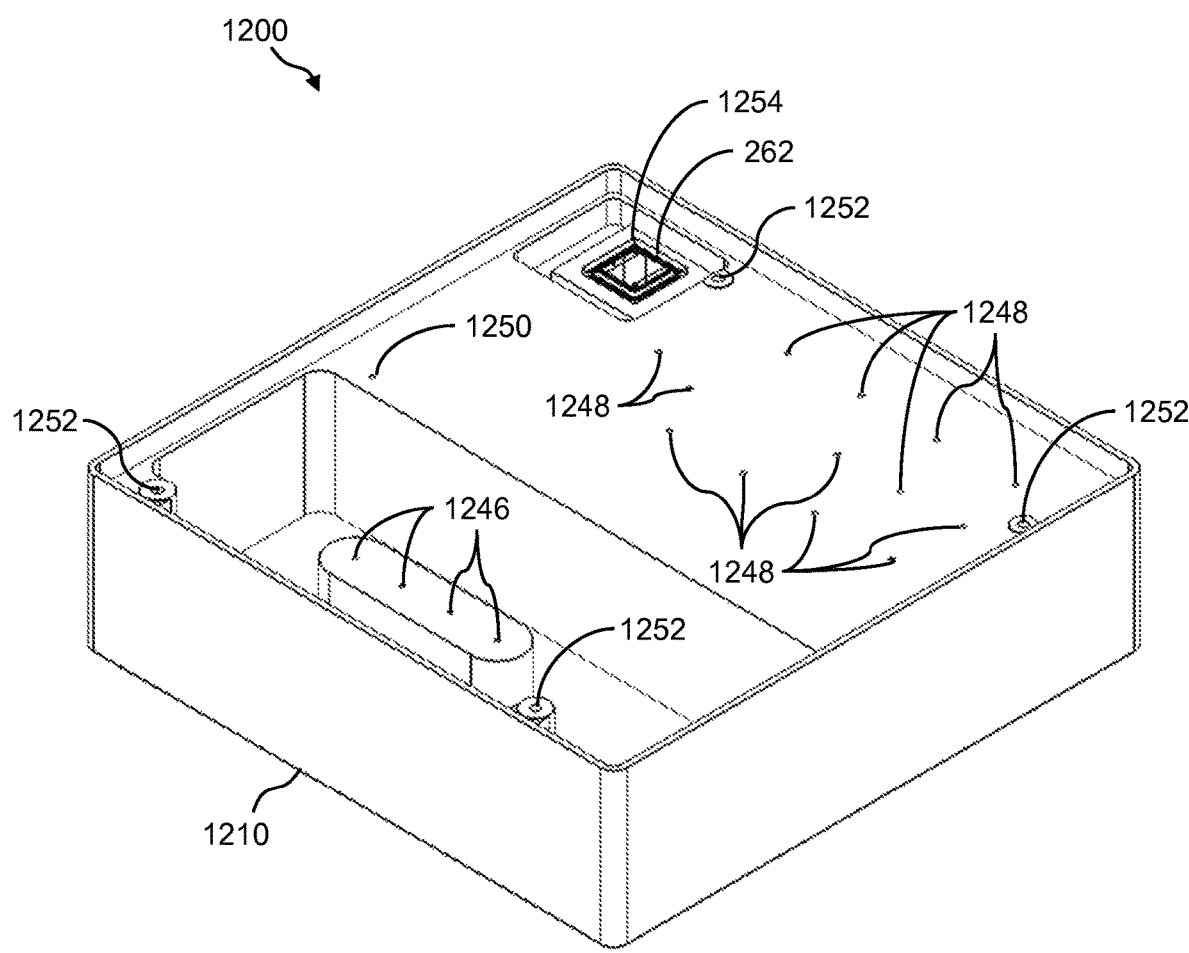
Figure 28:
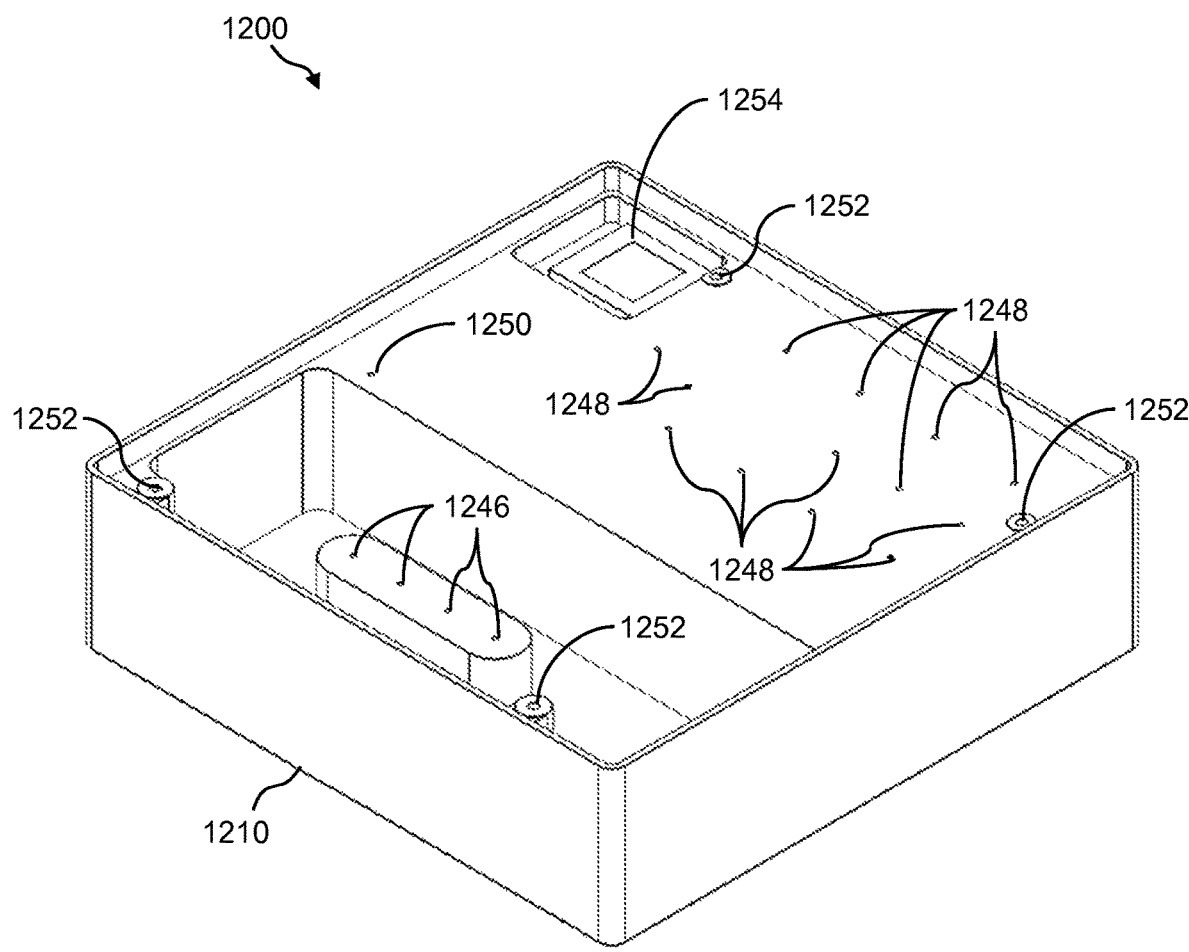
Figure 29:
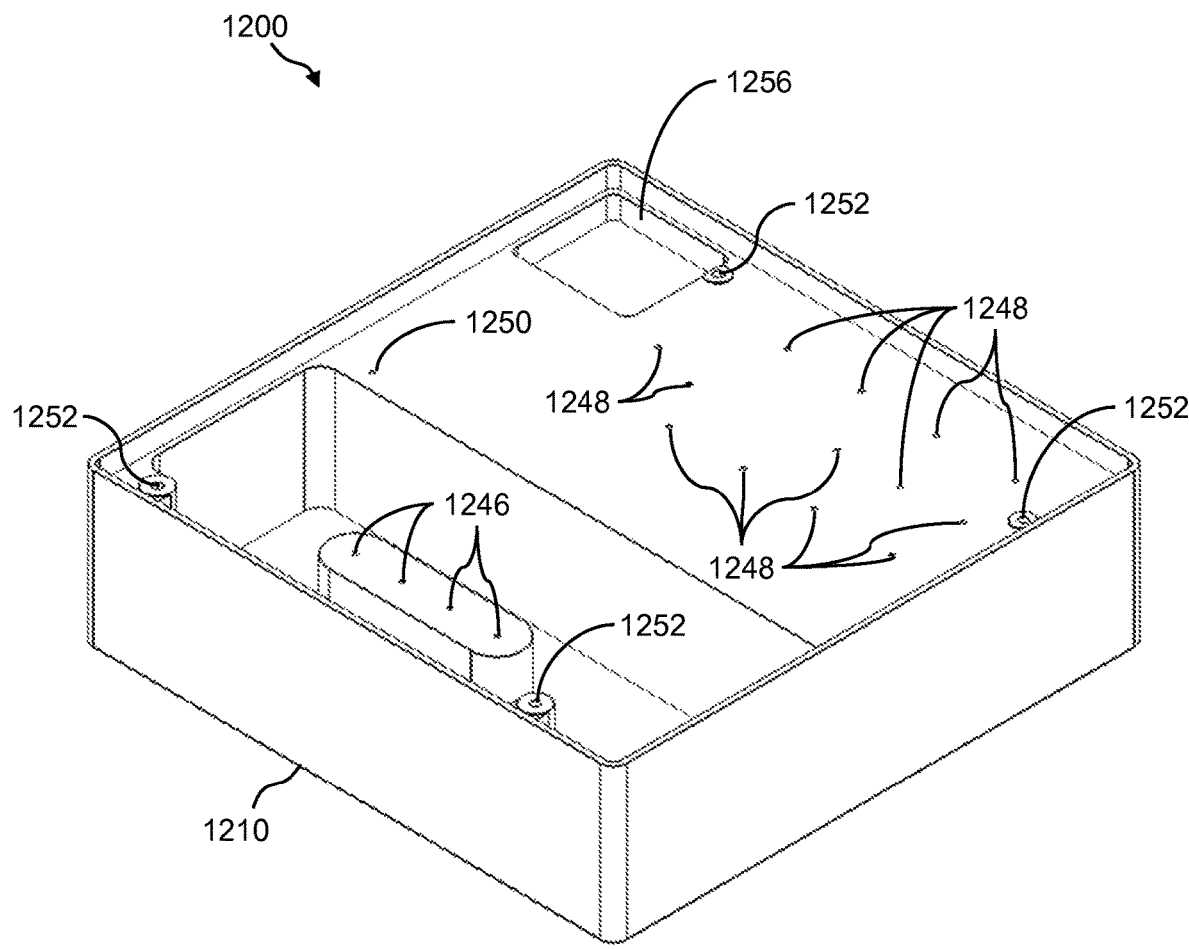

Referring now to FIG. 27, both fluidics layers 200 and flexible PCB heater 1412 have been removed from housing 1210. FIG. 27 also shows four treaded holes 1252 for receiving screws 1238. Further, FIG. 27 shows CMOS image sensor 262 and a portion of a protective cap 1254 that is covering CMOS image sensor 262. Referring now to FIG. 28, CMOS image sensor 262 has been removed so that protective cap 1254 is fully visible. Referring now to FIG. 29, protective cap 1254 has been removed showing a clearance region 1256 in housing 1210 that is associated with CMOS image sensor 262.

Figure 30:
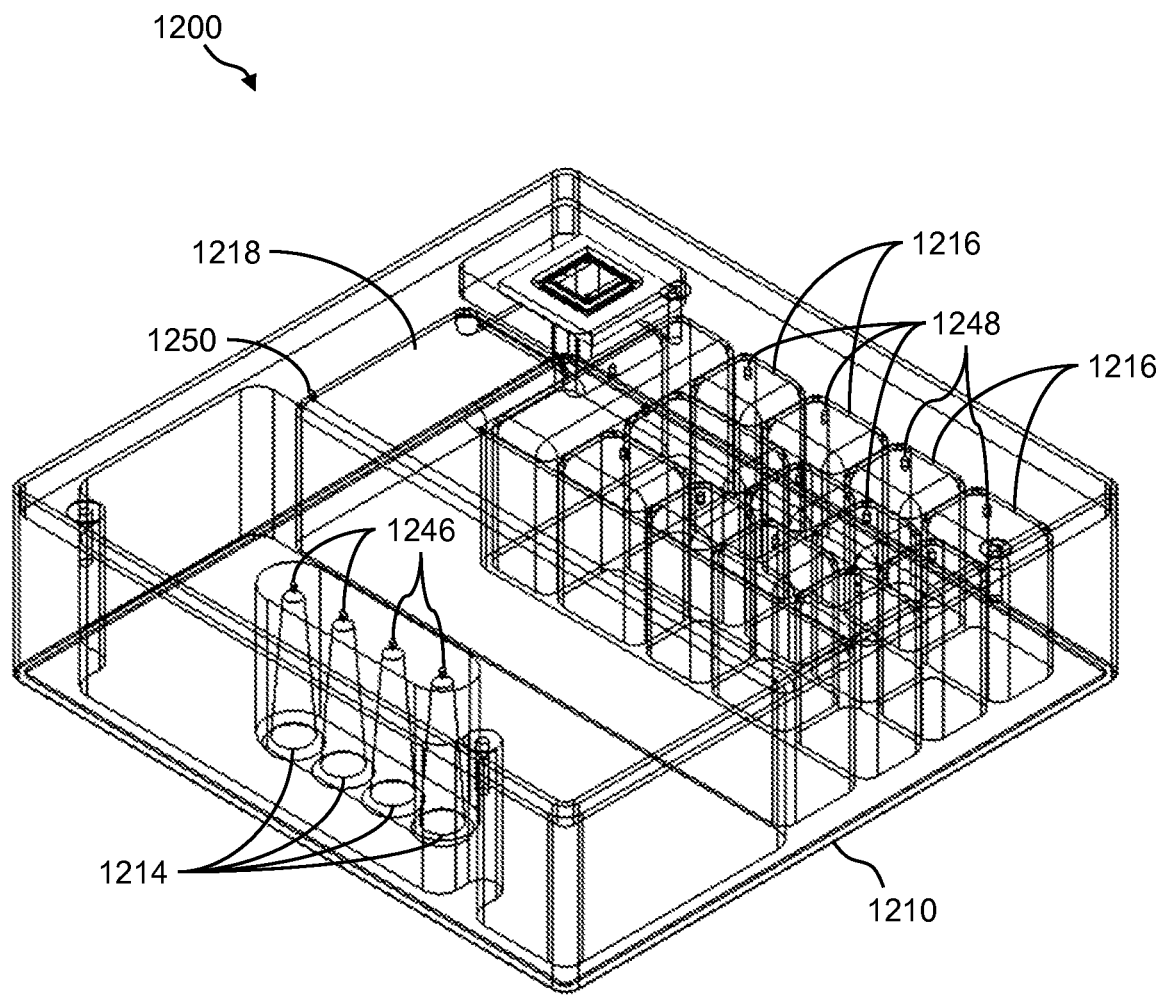
FIG. 30 shows a transparent perspective view of a portion of the microfluidic cartridge assembly of FIG. 12 and showing the various reagent fluid reservoirs and sample loading ports thereof.

FIG. 30 shows a transparent perspective view of housing 1210 of microfluidic cartridge assembly 1200 in order to show the positions of the openings with respect to sample loading ports 1214, reagent reservoirs 1216, and waste reservoir 1218. Namely, in this view one can see the positions of openings 1246 with respect to sample loading ports 1214, the positions of openings 1248 with respect to reagent reservoirs 1216, and the position of opening 1250 with respect to waste reservoir 1218.

Figure 31:
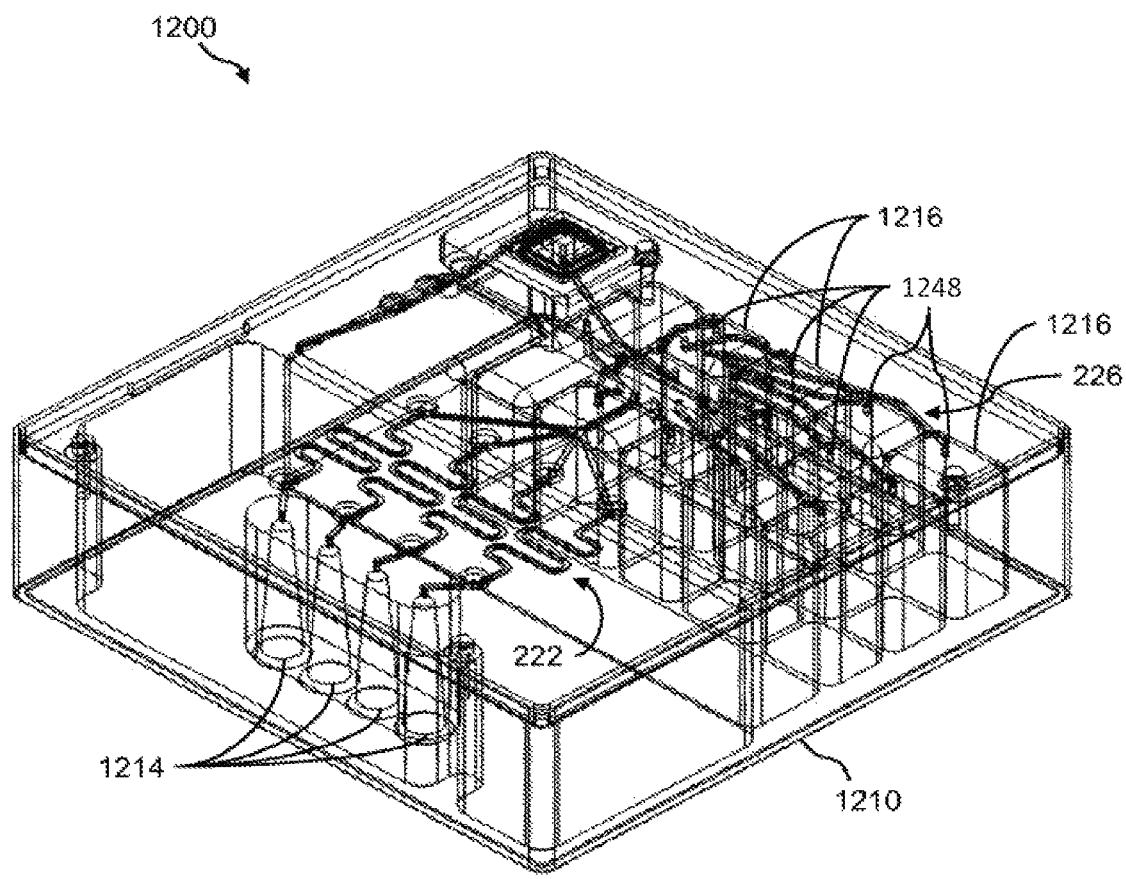
FIG. 31 shows another transparent perspective view of a portion of the microfluidic cartridge assembly of FIG. 12 and further showing the fluidics channels thereof.
Figure 32:
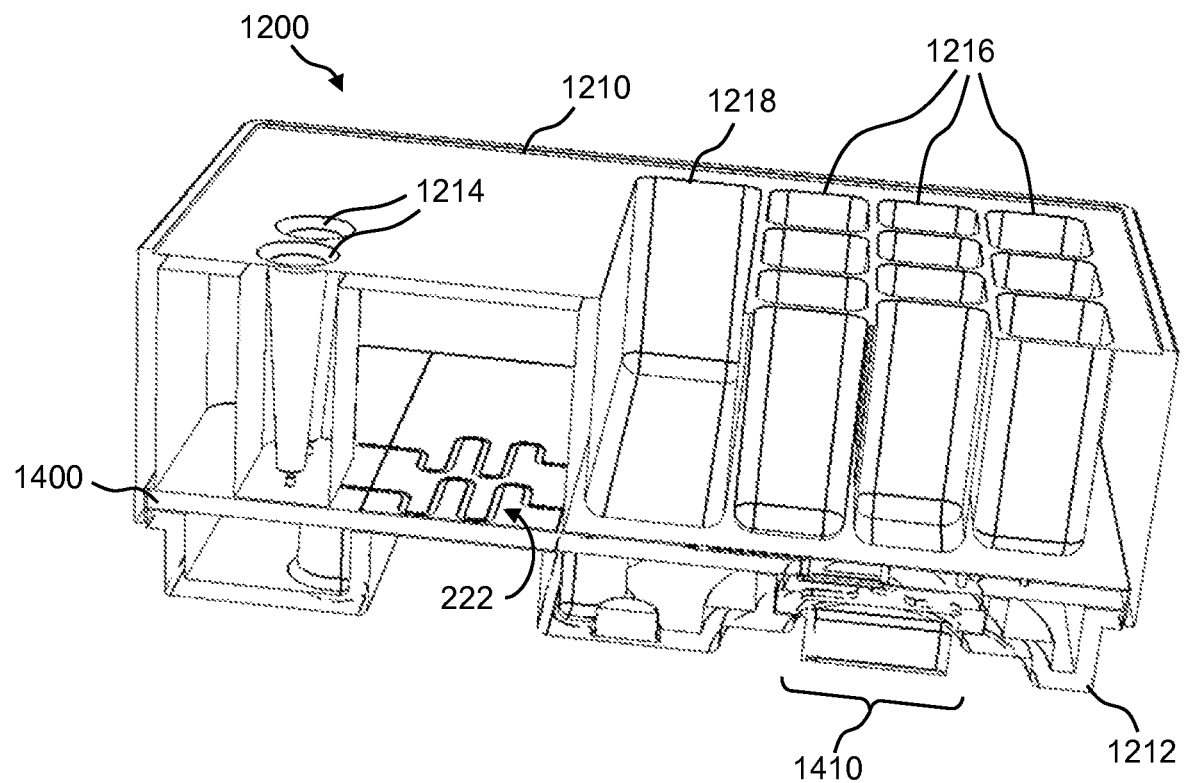
FIG. 32 shows a cross-sectional view of the microfluidic cartridge assembly of FIG. 12, which shows more details thereof.

FIG. 31 shows a transparent perspective view of housing 1210 of microfluidic cartridge assembly 1200 with the various fluidics channels overlaid thereon. Namely, in this view one can see the positions of the various fluidics channels with respect to sample loading ports 1214, reagent reservoirs 1216, and waste reservoir 1218. FIG. 32 shows a cross-sectional view of microfluidic cartridge assembly 1200 of FIG. 12, which shows more details thereof.

Figure 33A:
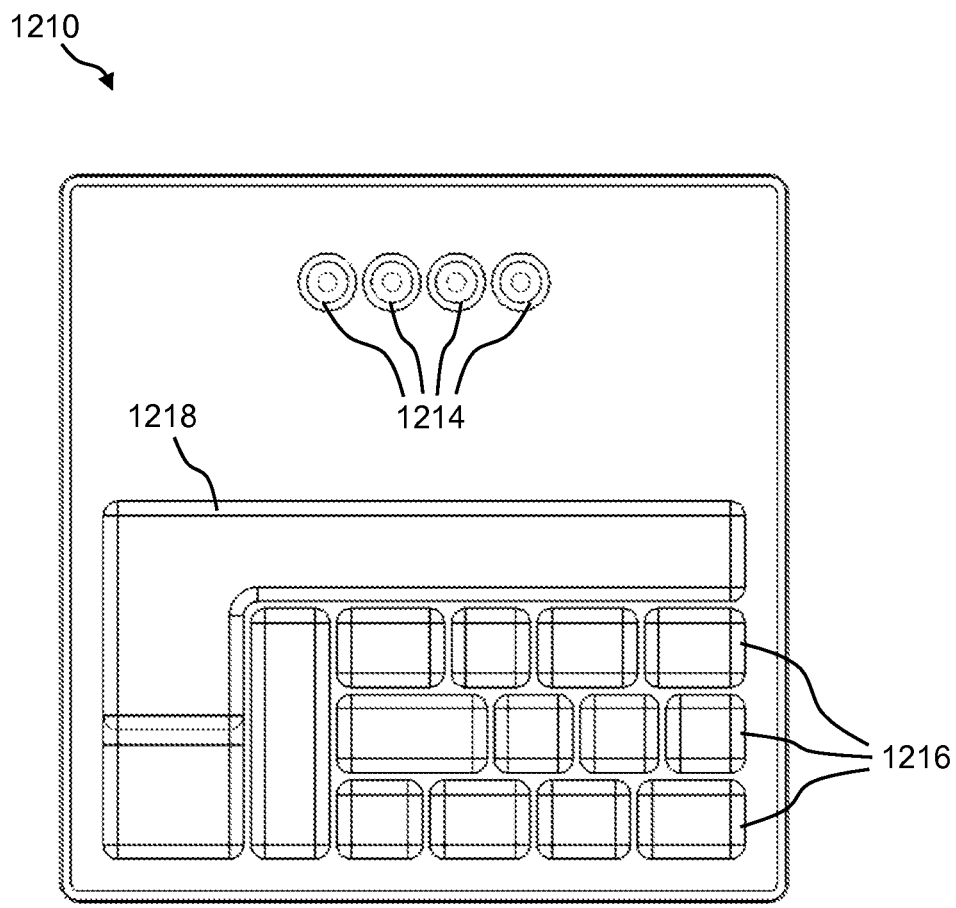
FIGS. 33A, 33B, 34A, 34B, and 35 show various views of the housing of the microfluidic cartridge assembly of FIG. 12, which shows more details thereof.
Figure 33B:
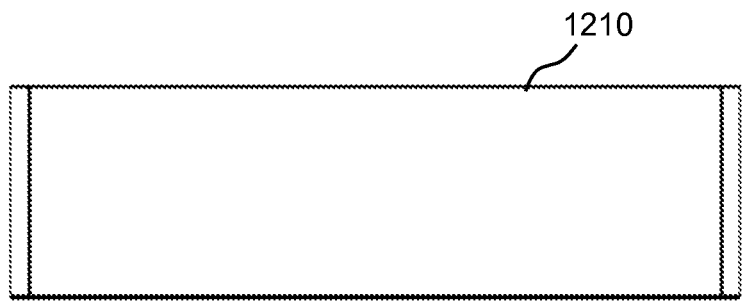
Figure 34A:
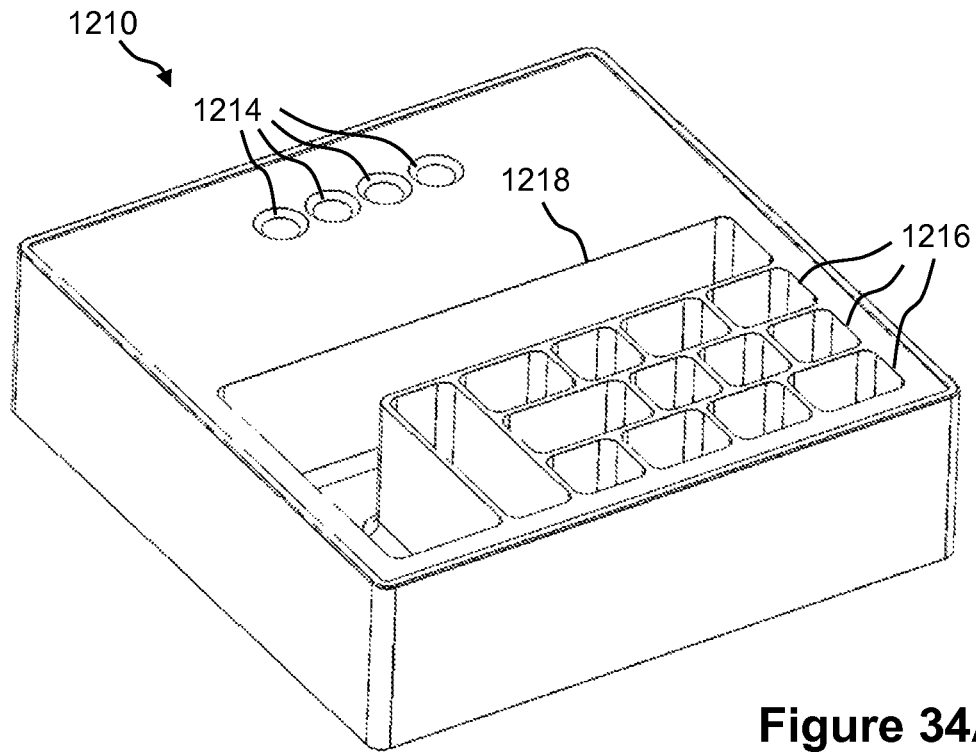
Figure 34B:
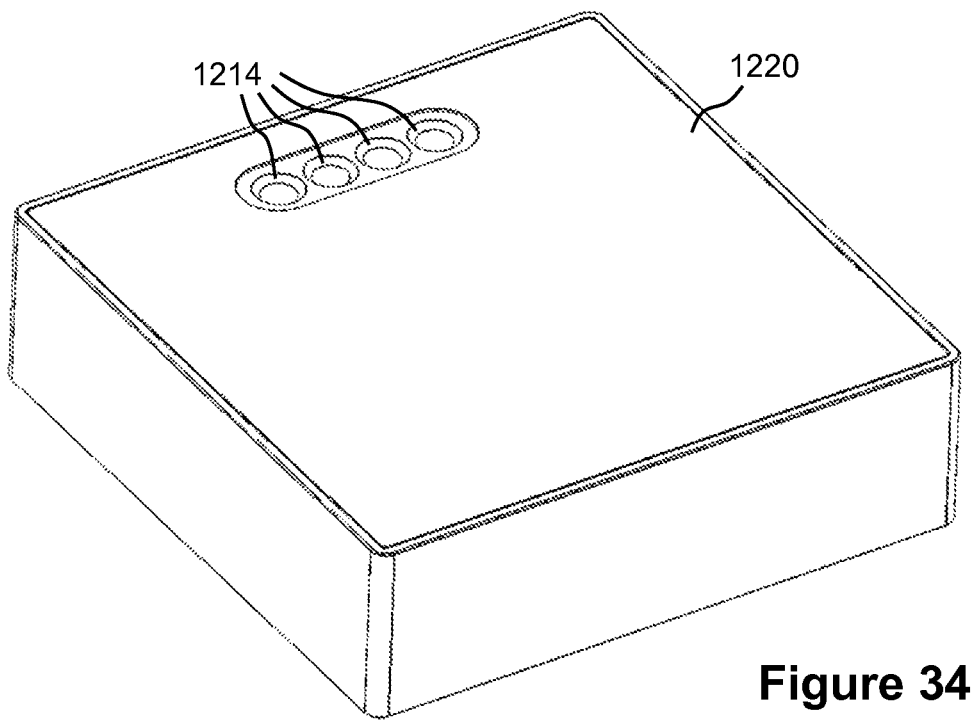
Figure 35:
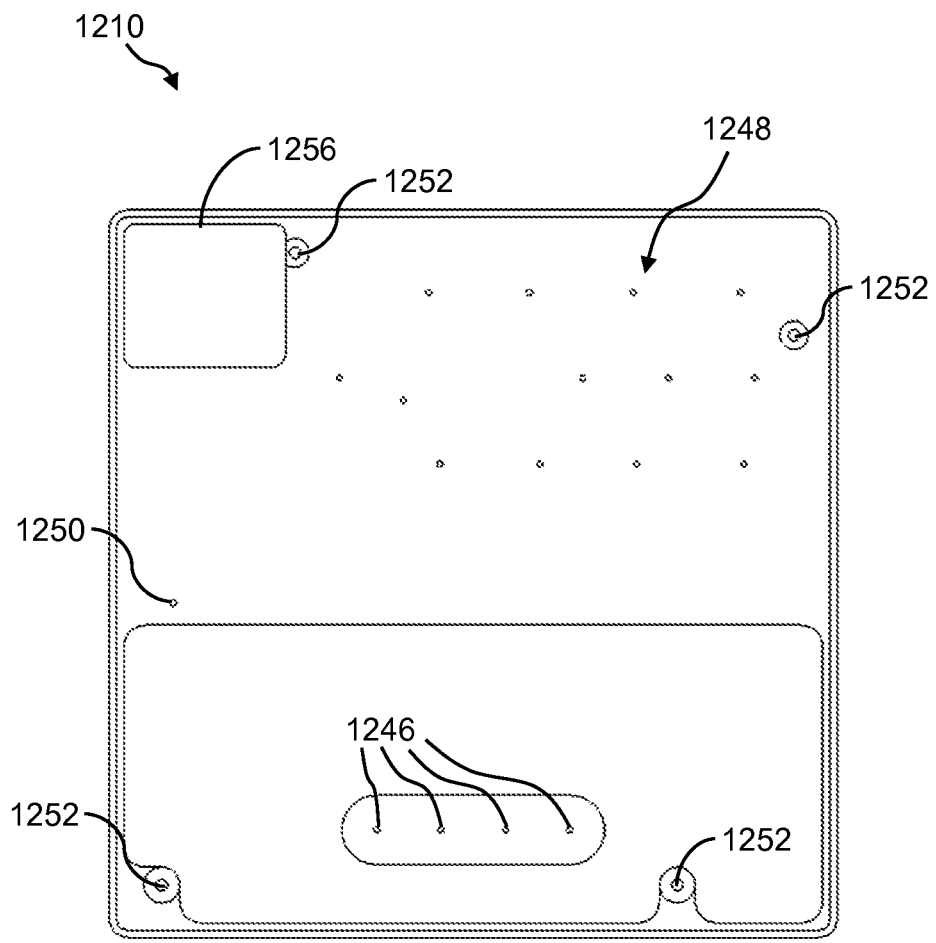

FIGS. 33A, 33B, 34A, 34B, and 35 show various views of housing 1210 of microfluidic cartridge assembly 1200 of FIG. 12, which shows more details thereof. Namely, FIGS. 33A and 33B show a plan view and a side view, respectively, of housing 1210. In one example, housing 1210 is from about 12 mm to about 100 mm in height, from about 100 mm to about 200 mm in length, from about 100 mm to about 200 mm in width. FIG. 34A shows a perspective view of housing 1210 without foil seal 1220 installed. FIG. 34B shows a perspective view of housing 1210 with foil seal 1220 installed. While FIGS. 33A, 33B, 34A, and 34B show the outside of housing 1210, FIG. 35 shows a plan view of the inside of housing 1210.

Figure 36:
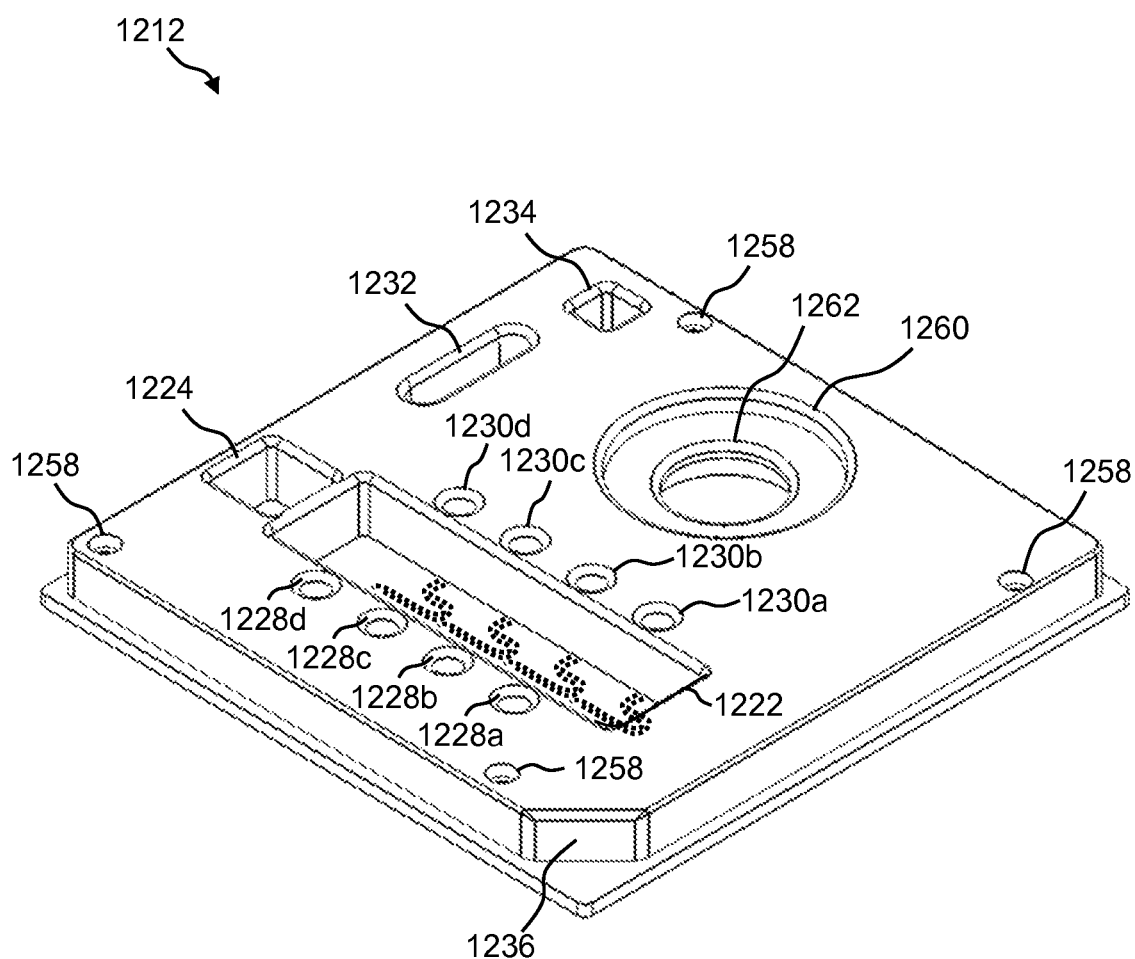
FIGS. 36, 37, 38A, 38B, and 39 show various views of the base plate of the microfluidic cartridge assembly of FIG. 12, which shows more details thereof.
Figure 37:
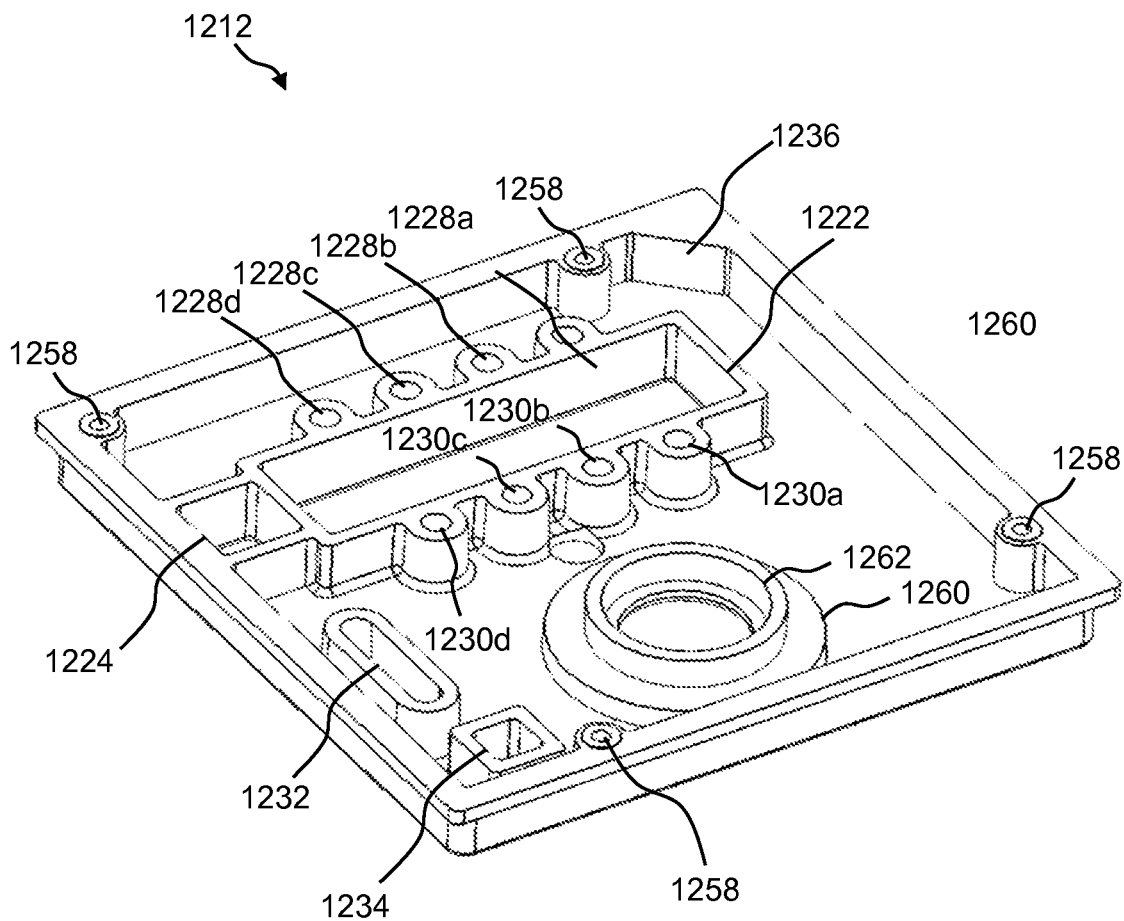
Figure 38A:
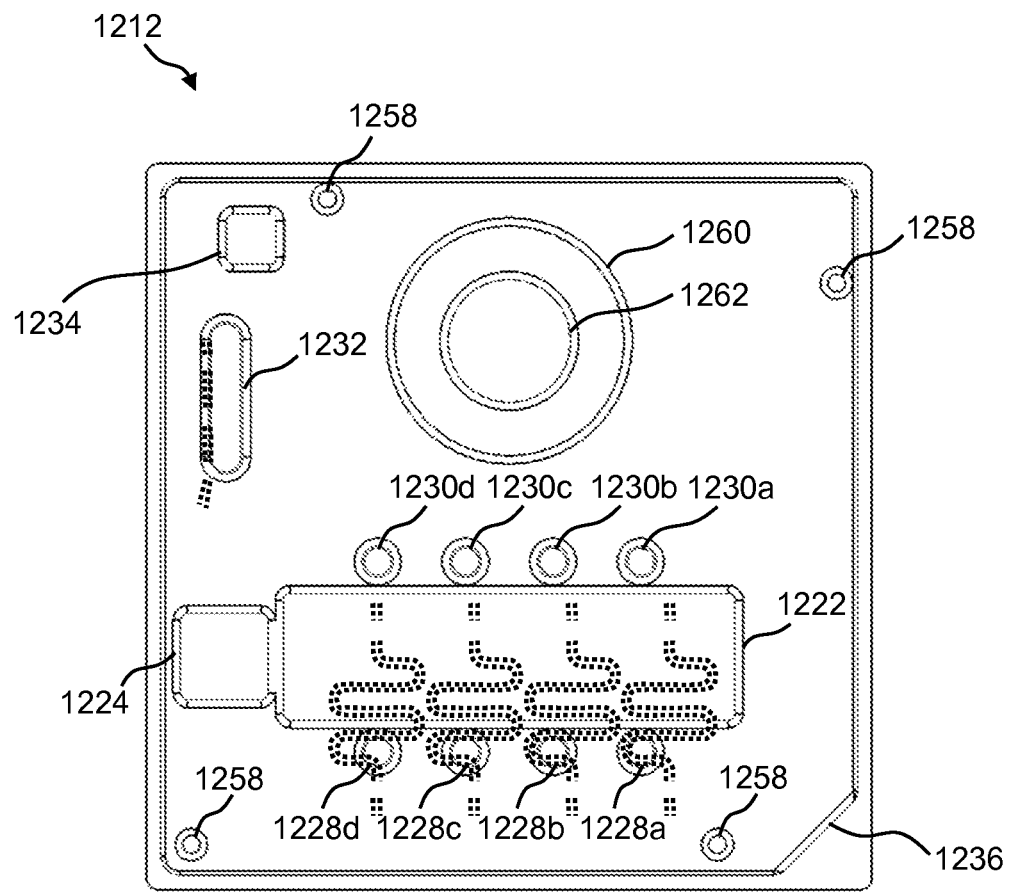
Figure 38B:
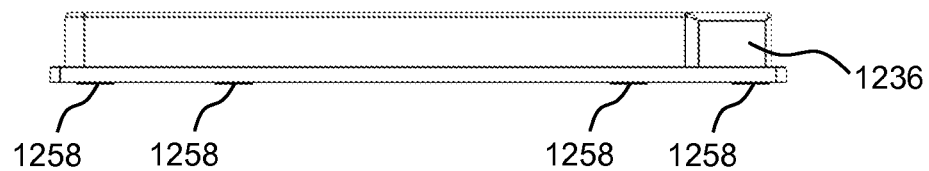
Figure 39:
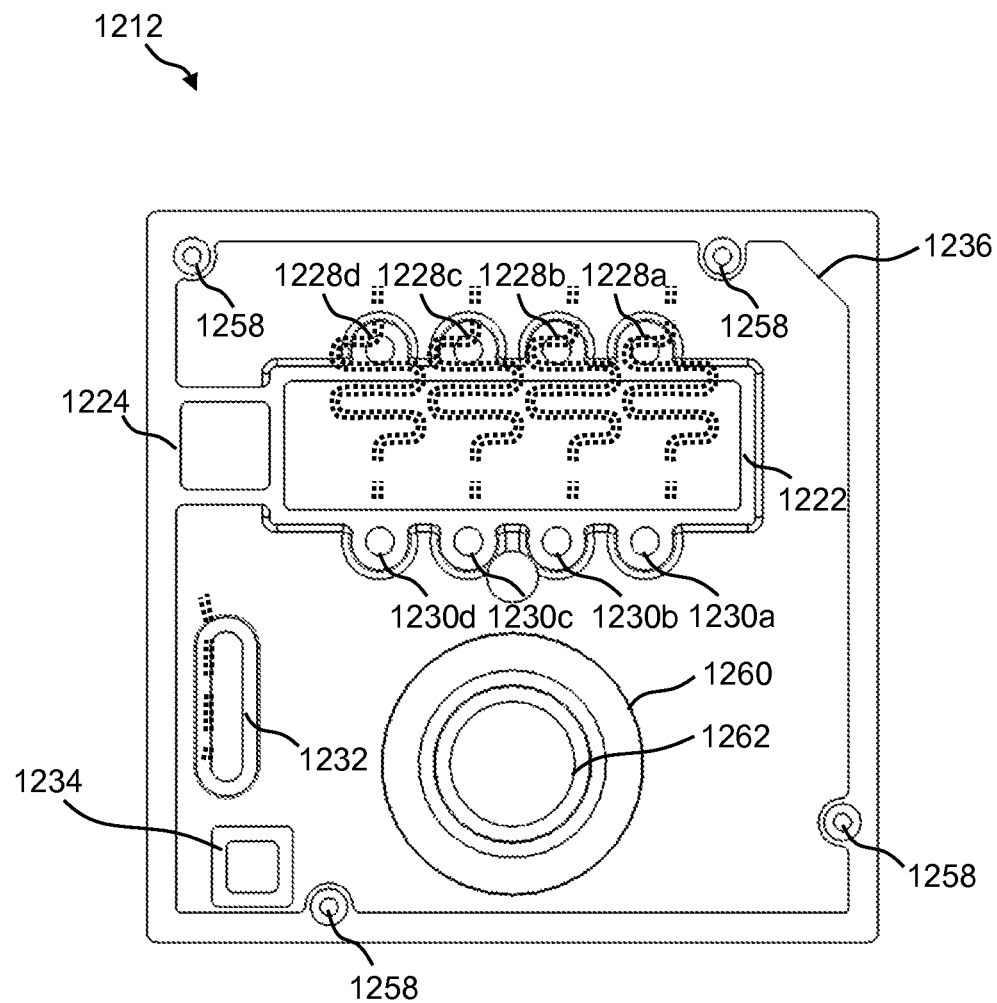

FIGS. 36, 37, 38A, 38B, and 39 show various views of base plate 1212 of microfluidic cartridge assembly 1200 of FIG. 12, which shows more details thereof. Namely, FIGS. 36 and 37 show perspective views of the outside and inside, respectively, of base plate 1212. FIG. 38A shows a plan view of the outside of base plate 1212, while FIG. 38B shows a side view of base plate 1212. FIGS. 36, 37, 38A, 38B, and 39 show that base plate 1212 further includes four holes 1258 for receiving screws 1238, a recessed region 1260 with an opening 1262 at its center for receiving grip portion 1240 and flow controller portion 1242 of rotary valve assembly 1410.

Figure 40A:
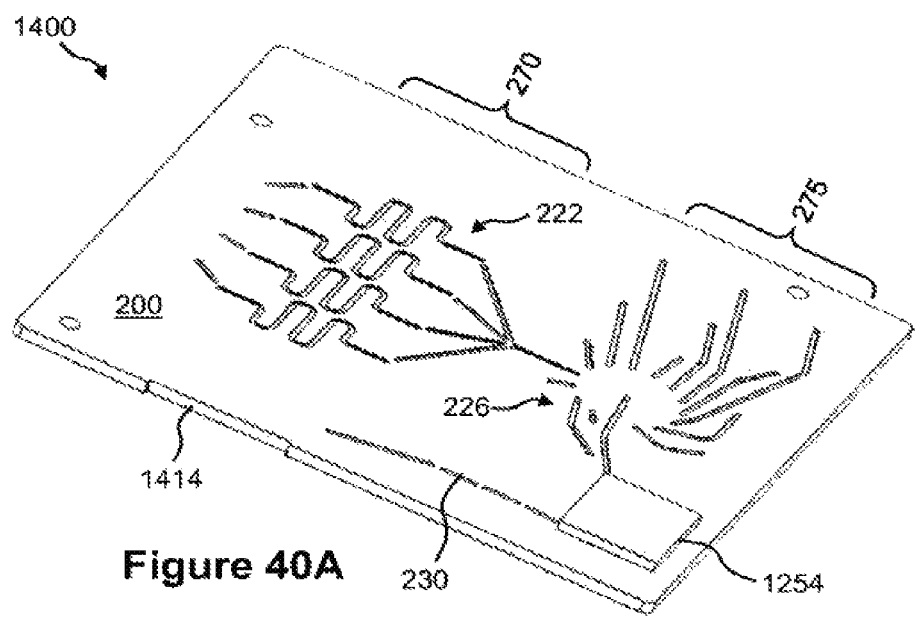
FIGS. 40A and 40B illustrate other perspective views of the fluidics assembly of the microfluidic cartridge assembly showing more details thereof.
Figure 40B:
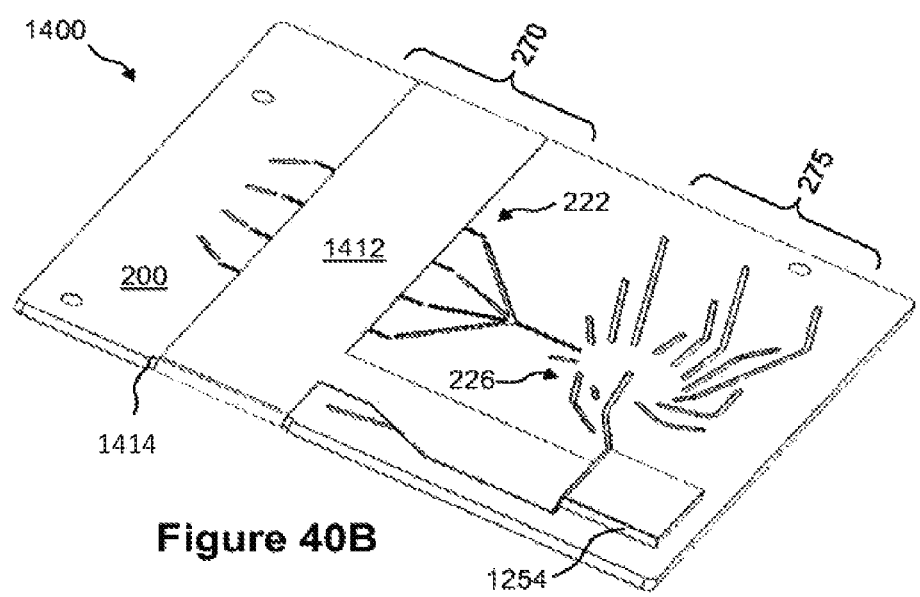

FIGS. 40A and 40B illustrate other perspective views of fluidics assembly 1400 of microfluidic cartridge assembly 1200 showing more details thereof. Namely, FIGS. 40A and 40B each show a perspective view of fluidics assembly 1400. FIG. 40A shows fluidics assembly 1400 without flexible PCB heater 1412, whereas FIG. 40B shows fluidics assembly 1400 with flexible PCB heater 1412 installed. Further, there is a notch 1414 on one edge of fluidics layers 200 and within PCR region 270. Notch 1414 is designed to receive flexible PCB heater 1412.

Figure 41A:
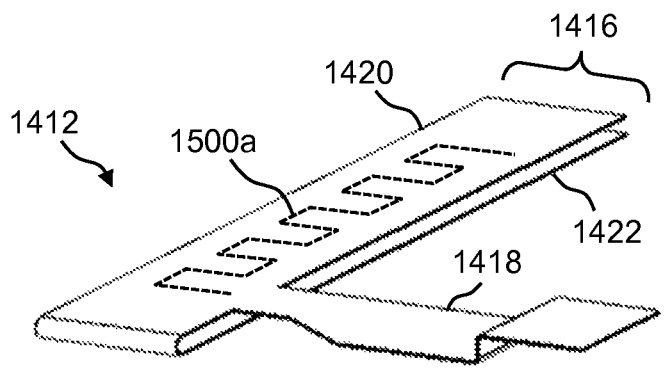
FIGS. 41A, 41B, and 41C illustrate other views showing more details of the flexible PCB heater of the fluidics assembly of the microfluidic cartridge assembly.
Figure 41B:
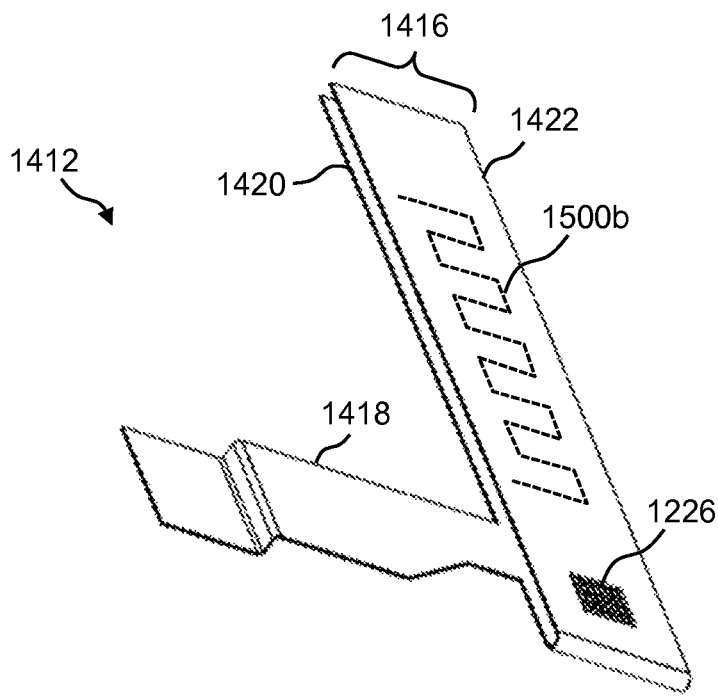
Figure 41C:
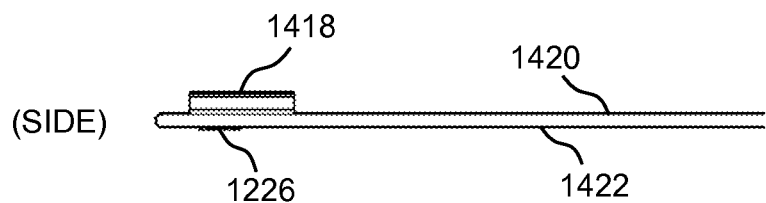

FIGS. 41A, 41B, and 41C illustrate various views showing more details of flexible PCB heater 1412 of fluidics assembly 1400 of microfluidic cartridge assembly 1200. Namely, FIGS. 41A and 41B show perspective views of each side, respectively, of flexible PCB heater 1412, while FIG. 41C shows a side view of flexible PCB heater 1412. Flexible PCB heater 1412 comprises a U-shaped wraparound panel 1416 and a side extension panel 1418, all formed using flexible PCB technology. The U-shaped wraparound panel 1416 comprises a panel 1420 and a panel 1422, each having a heater trace 1500 patterned therein, e.g., heater traces 1500$a$ and 1500$b$. An example of heater trace 1500 is shown in FIGS. 15A and 15B. The space between panel 1420 and panel 1422 is set so that flexible PCB heater 1412 can be press-fitted onto PCR region 270 of fluidics layers 200 and fitted into notch 1414, as shown in FIG. 40B. FIGS. 41B and 41C also show I/O pads 1226, which provide the electrical connections to the two heater traces 1500 as well as to CMOS image sensor 262.

Side extension panel 1418 extends from panel 1420 near the bend in the U-shaped wraparound panel 1416. Side extension panel 1418 is designed to extend towards CMOS image sensor 262. As shown in FIG. 40B, the end of side extension panel 1418 farthest from the U-shaped wraparound panel 1416 is shaped to be fitted against CMOS image sensor 262. The purpose of side extension panel 1418 is to provide the electrical connection to CMOS image sensor 262, which is assembled atop the rigid or flexible PCB.

Figure 42A:
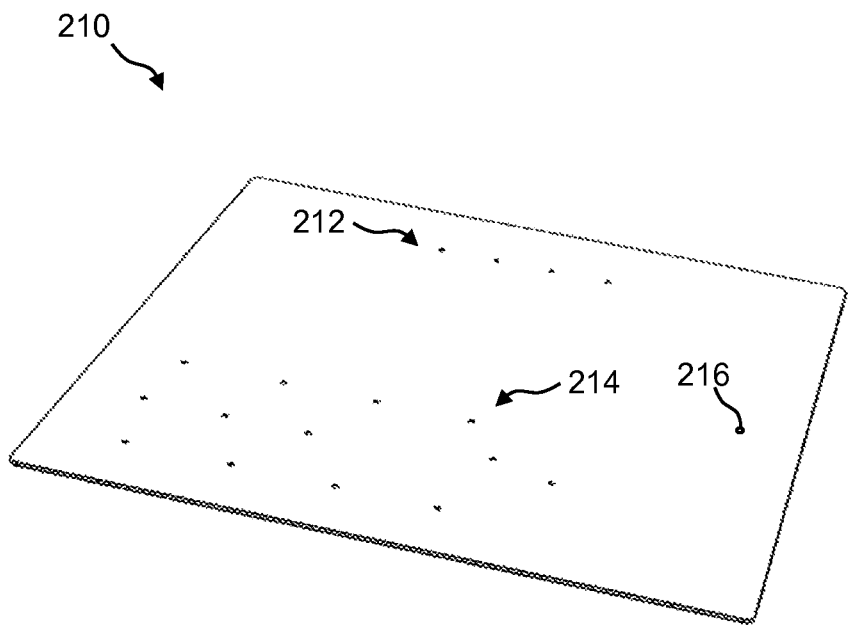
FIGS. 42A and 42B show a perspective view and plan view, respectively, of the inlet/outlet ports layer of the fluidics layers shown in FIG. 2 and FIG. 14.
Figure 42B:
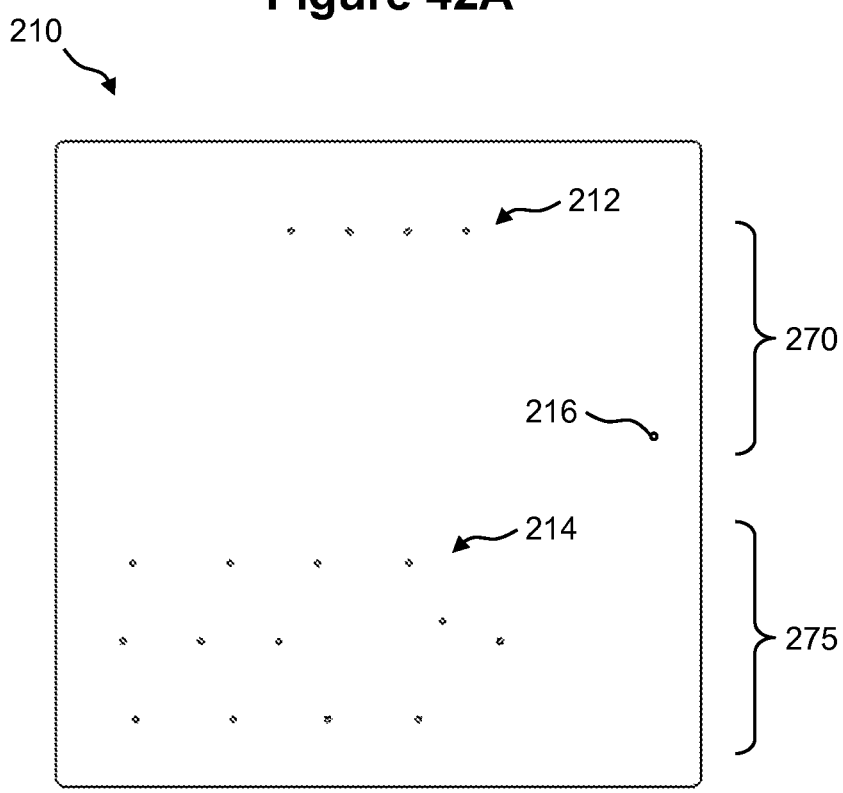

FIGS. 42A and 42B show a perspective view and plan view, respectively, of inlet/outlet ports layer 210 of fluidics layers 200 shown in FIG. 2 and FIG. 14. Again, inlet/outlet ports layer 210 can be formed of, for example, polycarbonate or any other materials that are suitable for use with a R2R process. Inlet/outlet ports layer 210 provides the interface between fluidics layers 200 and housing 1210 of microfluidic cartridge assembly 1200. Namely, inlet/outlet ports layer 210 provides the fluid paths from sample loading ports 1214, the thirteen reagent reservoirs 1216, and waste reservoir 1218 of housing 1210 to fluidics channels layer 220 of fluidics layers 200. For example, inlet/outlet ports layer 210 includes a set of openings 212 that substantially align with openings 1246 of sample loading ports 1214 in housing 1210. Inlet/outlet ports layer 210 includes a set of openings 214 that substantially align with openings 1248 of reagent reservoirs 1216 in housing 1210. Inlet/outlet ports layer 210 also includes an opening 216 that substantially align with opening 1250 of waste reservoir 1218 in housing 1210.

Figure 43A:
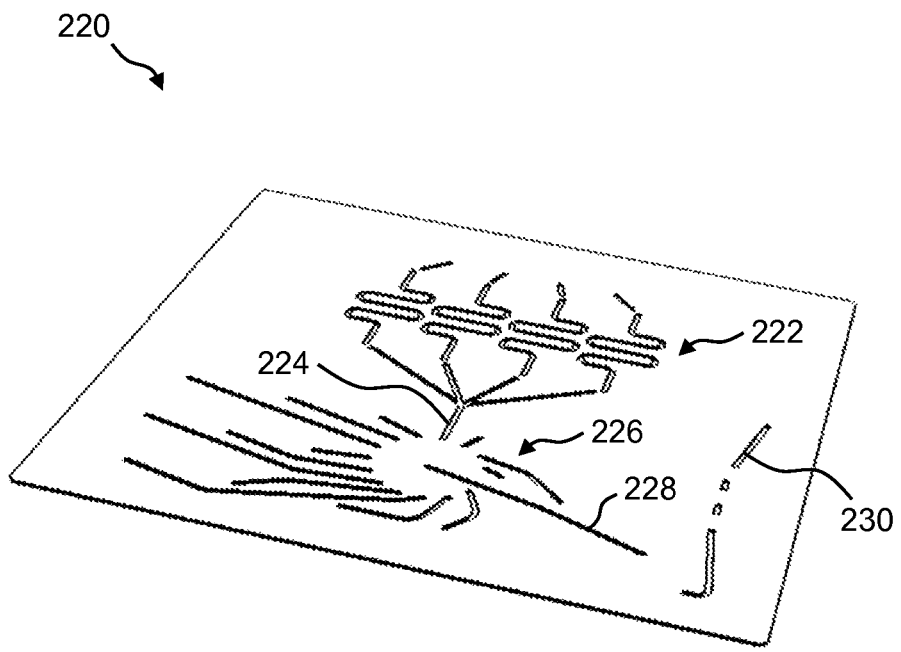
FIGS. 43A and 43B show a perspective view and plan view, respectively, of the fluidics channels layer of the fluidics layers shown in FIG. 2 and FIG. 14.
Figure 43B:
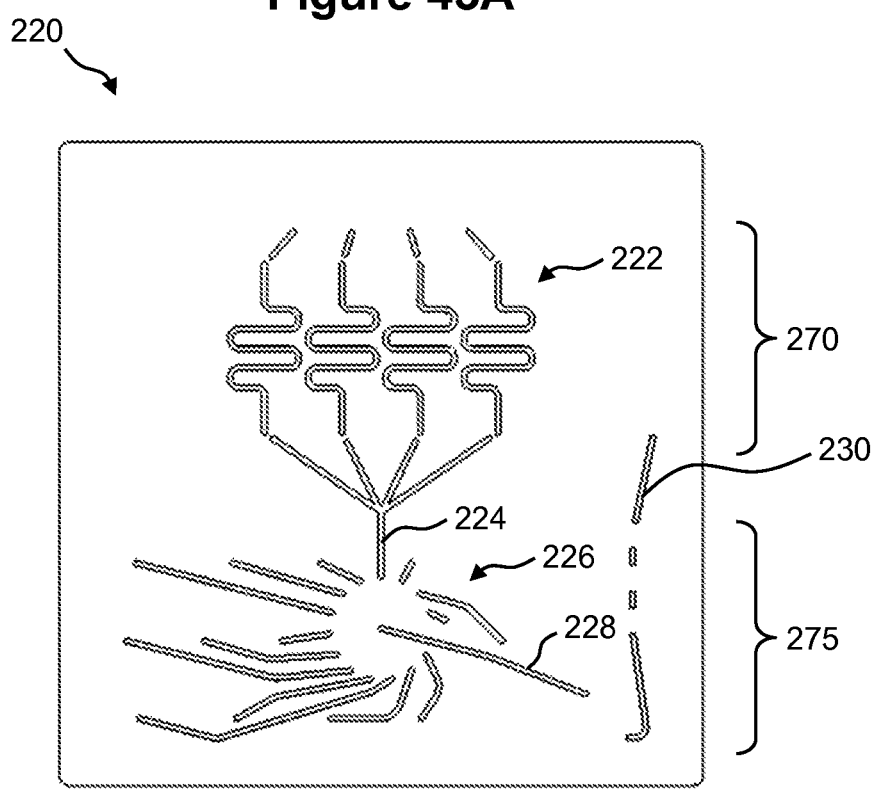

FIGS. 43A and 43B show a perspective view and plan view, respectively, of fluidics channels layer 220 of fluidics layers 200 shown in FIG. 2 and FIG. 14. Again, fluidics channels layer 220 can be formed of, for example, polycarbonate or any other materials that are suitable for use with a R2R process. Fluidics channels layer 220 is the layer of fluidics layers 200 at which the flow of all liquids is facilitated. Namely, all PCR and sequencing operations take place at fluidics channels layer 220. PCR operations take place in PCR channels 222 at PCR region 270. PCR output channel 224 supplies reagent mixing and distribution region 275. Reagent distribution takes place using reagent channels 226 at reagent mixing and distribution region 275. The thirteen reagent channels 226 are patterned to supply rotary valve assembly 1410. Sequencing feed channel 228 supplies the inlet of sequencing chamber 258 of sequencing chamber layer 250 shown in FIGS. 45A and 45B. Then, sequencing outlet channel 230 is fluidly connected to the outlet of sequencing chamber 258.

Figure 44A:
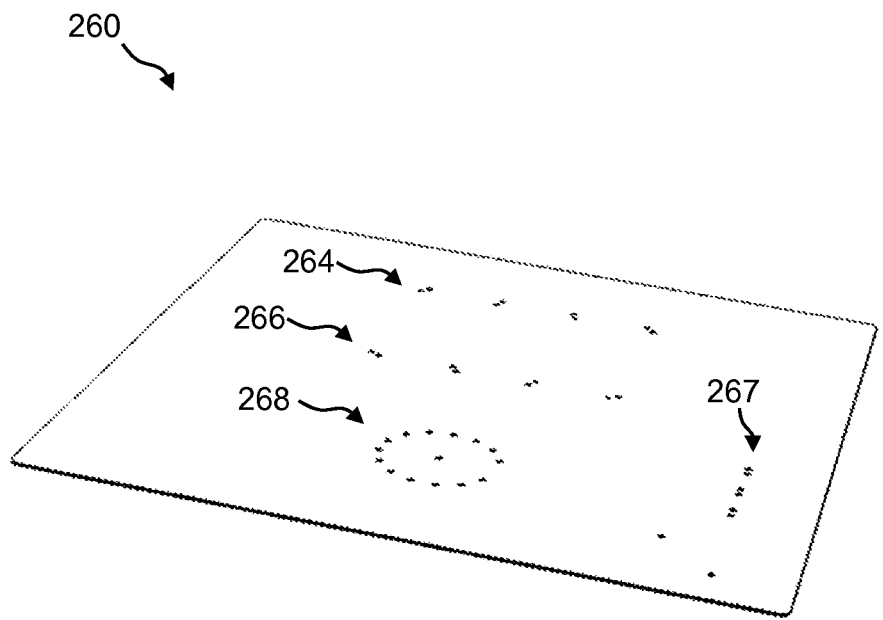
FIGS. 44A and 44B show a perspective view and plan view, respectively, of the flexible PCB layer of the fluidics layers shown in FIG. 2 and FIG. 14.
Figure 44B:
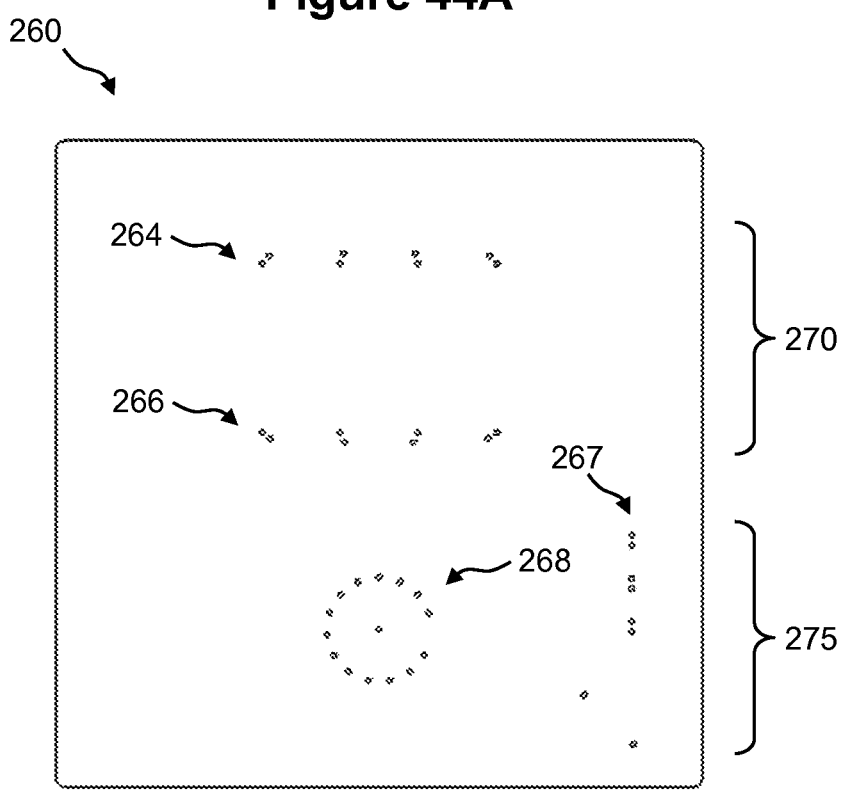

FIGS. 44A and 44B show a perspective view and plan view, respectively, of flexible PCB layer 260 of fluidics layers 200 shown in FIG. 2 and FIG. 14. Again, flexible PCB layer 260 can be formed of, for example, polyimide or any other materials that are suitable for use with a R2R process. Flexible PCB layer 260 includes a set of openings (or holes) 264 that correlate to the inlets/outlets of membrane valves 242. Flexible PCB layer 260 also includes a set of openings (or holes) 266 that correlate to the inlets/outlets of membrane valves 244. If membrane valves 246 are present, flexible PCB layer 260 includes a set of openings (or holes) 267 that correlate to the inlets/outlets of membrane valves 246. Further, flexible PCB layer 260 includes a set of openings 268 that substantially align with and provide fluid paths to rotary valve assembly 1410.

Figure 45A:
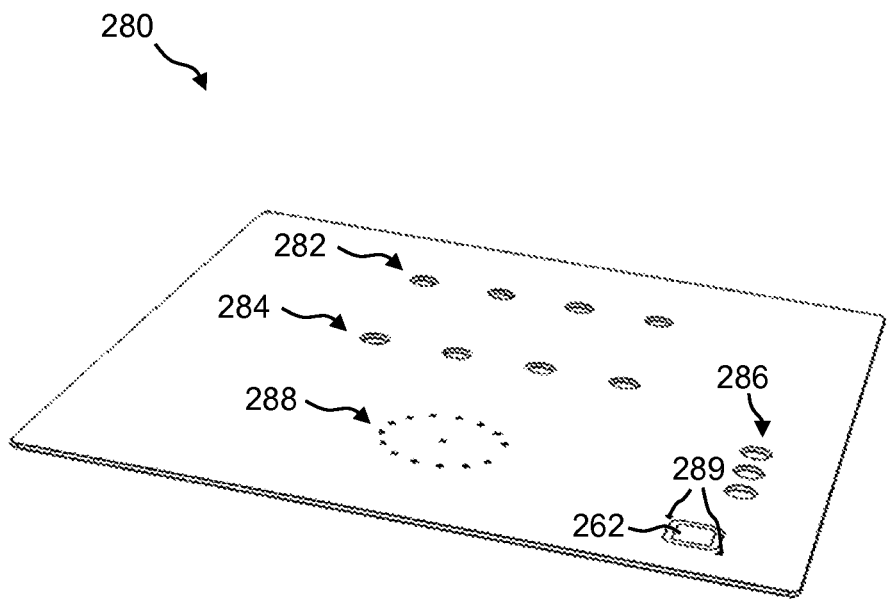
FIGS. 45A and 45B show a perspective view and plan view, respectively, of the sequencing chamber bottom layer of the fluidics layers shown in FIG. 2 and FIG. 14.
Figure 45B:
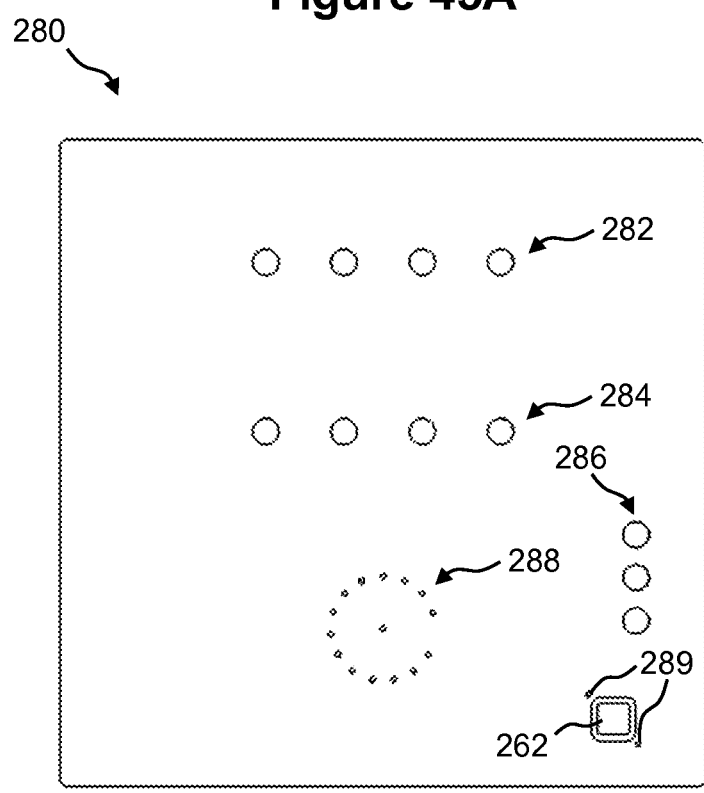

FIGS. 45A and 45B show a perspective view and plan view, respectively, of sequencing chamber bottom layer 280 of fluidics layers 200 shown in FIG. 2 and FIG. 14. Again, sequencing chamber bottom layer 280 can be formed of, for example, polycarbonate or any other materials that are suitable for use with a R2R process. Sequencing chamber bottom layer 280 includes a set of openings 282 for forming membrane valves 242 within the stack of fluidics layers 200. Sequencing chamber bottom layer 280 also includes a set of openings 284 for forming membrane valves 244 within the stack of fluidics layers 200. If membrane valves 246 are present, sequencing chamber bottom layer 280 includes a set of openings 286 for forming membrane valves 246 within the stack of fluidics layers 200. Further, sequencing chamber bottom layer 280 includes a set of openings 288 that substantially align with and provide fluid paths to rotary valve assembly 1410. Additionally, sequencing chamber bottom layer 280 includes a pair of openings 289, which fluidly couple to sequencing chamber 258 of sequencing chamber layer 250.

Sequencing chamber bottom layer 280 is the layer of fluidics layers 200 at which the CMOS technology is integrated. Namely, CMOS image sensor 262 is installed on sequencing chamber bottom layer 280. The position of CMOS image sensor 262 substantially corresponds to the position of sequencing chamber 258 of sequencing chamber layer 250.

Figure 46A:
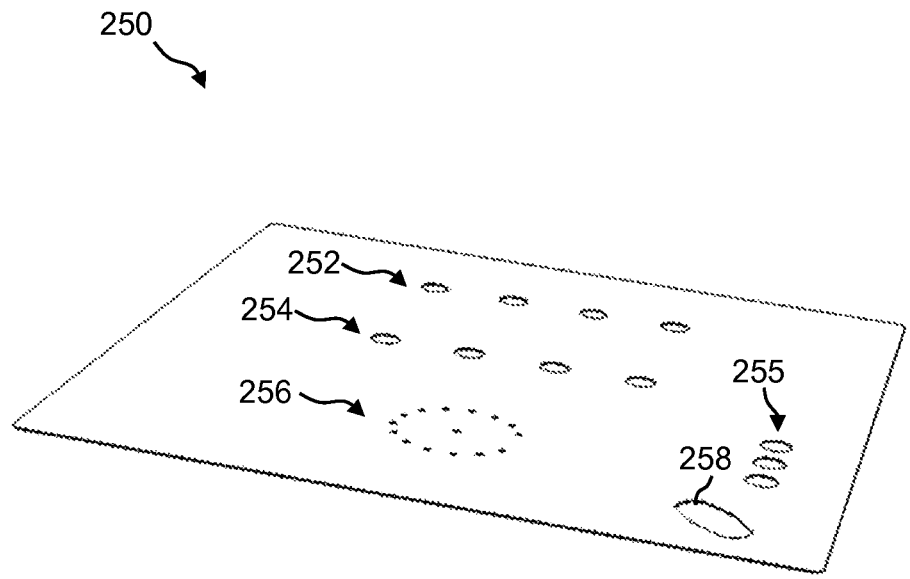
Figure 46B:
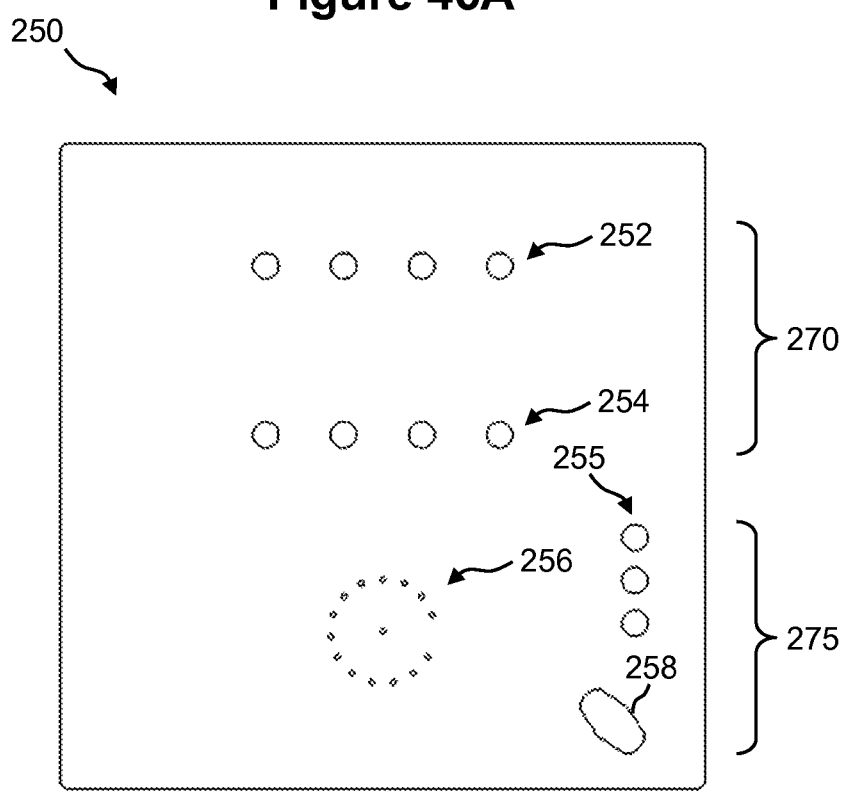

FIGS. 46A and 46B show a perspective view and plan view, respectively, of sequencing chamber layer 250 of fluidics layers 200 shown in FIG. 2 and FIG. 14. Again, sequencing chamber layer 250 can be formed of, for example, polycarbonate or any other materials that are suitable for use with a R2R process. Sequencing chamber layer 250 is the layer of fluidics layers 200 at which sequencing operations occur; namely, using sequencing chamber 258.

Sequencing chamber layer 250 includes a set of openings 252 for forming membrane valves 242 within the stack of fluidics layers 200. Sequencing chamber layer 250 also includes a set of openings 254 for forming membrane valves 244 within the stack of fluidics layers 200. If membrane valves 246 are present, sequencing chamber layer 250 includes a set of openings 255 for forming membrane valves 246 within the stack of fluidics layers 200. Further, sequencing chamber layer 250 includes a set of openings 256 that substantially align with and provide fluid paths to rotary valve assembly 1410.

Figure 47A:
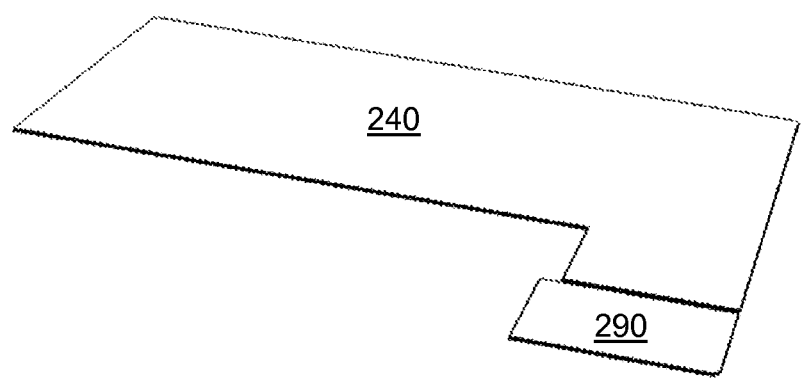
FIGS. 47A and 47B show a perspective view and plan view, respectively, of the membrane layer and the sequencing chamber top layer of the fluidics layers shown in FIG. 2 and FIG. 14.
Figure 47B:
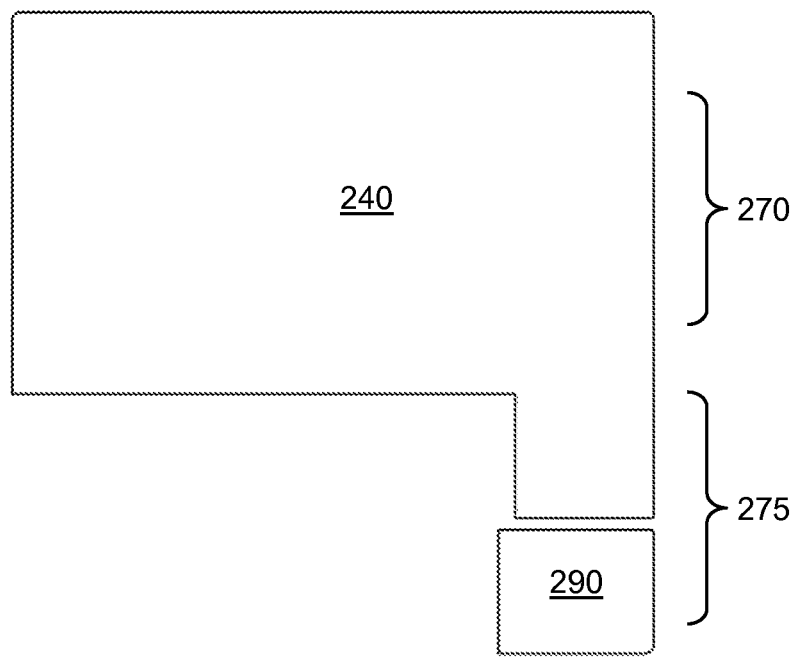

FIGS. 47A and 47B show a perspective view and plan view, respectively, of membrane layer 240 and sequencing chamber top layer 290 of fluidics layers 200 shown in FIG. 2 and FIG. 14. Membrane layer 240 can be formed of, for example, silicone elastomer, while sequencing chamber top layer 290 can be formed of, for example, COC. Membrane layer 240 serves as the elastic membrane for opening and closing membrane valves 242, 244, and 246 within the stack of fluidics layers 200, wherein membrane valves 242, 244, and 246 are created by the combination of, in order, flexible PCB layer 260, sequencing chamber bottom layer 280, sequencing chamber layer 250, and membrane layer 240. FIGS. 47A and 47B also shows sequencing chamber top layer 290, which is used to cover sequencing chamber 258 of sequencing chamber layer 250.

Figure 48A:
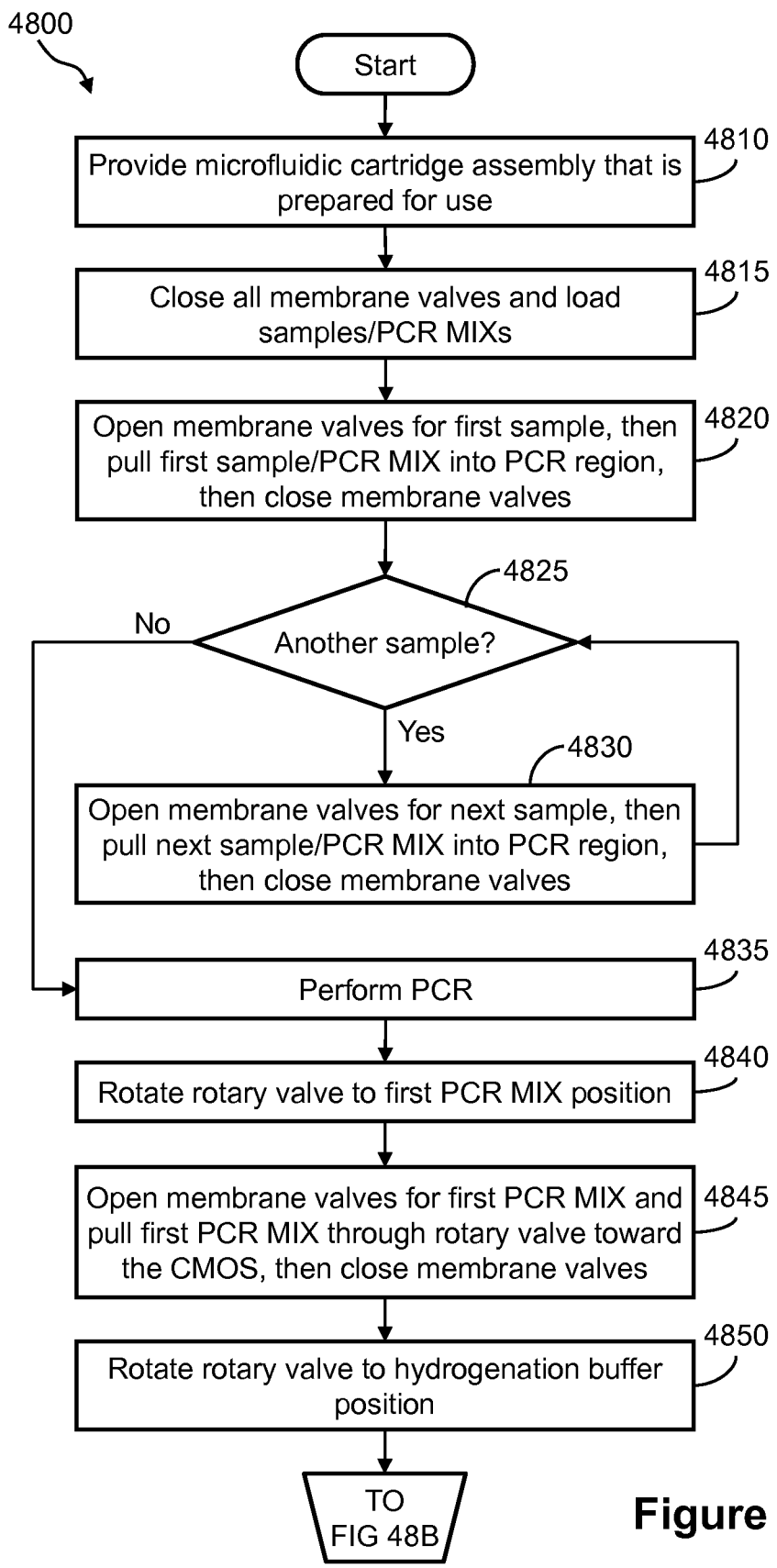
FIGS. 48A and 48B illustrate a flow diagram of an example of a method of using the microfluidic cartridge assembly to perform multiplex PCR and downstream mixing needed for sequencing.
Figure 48B:
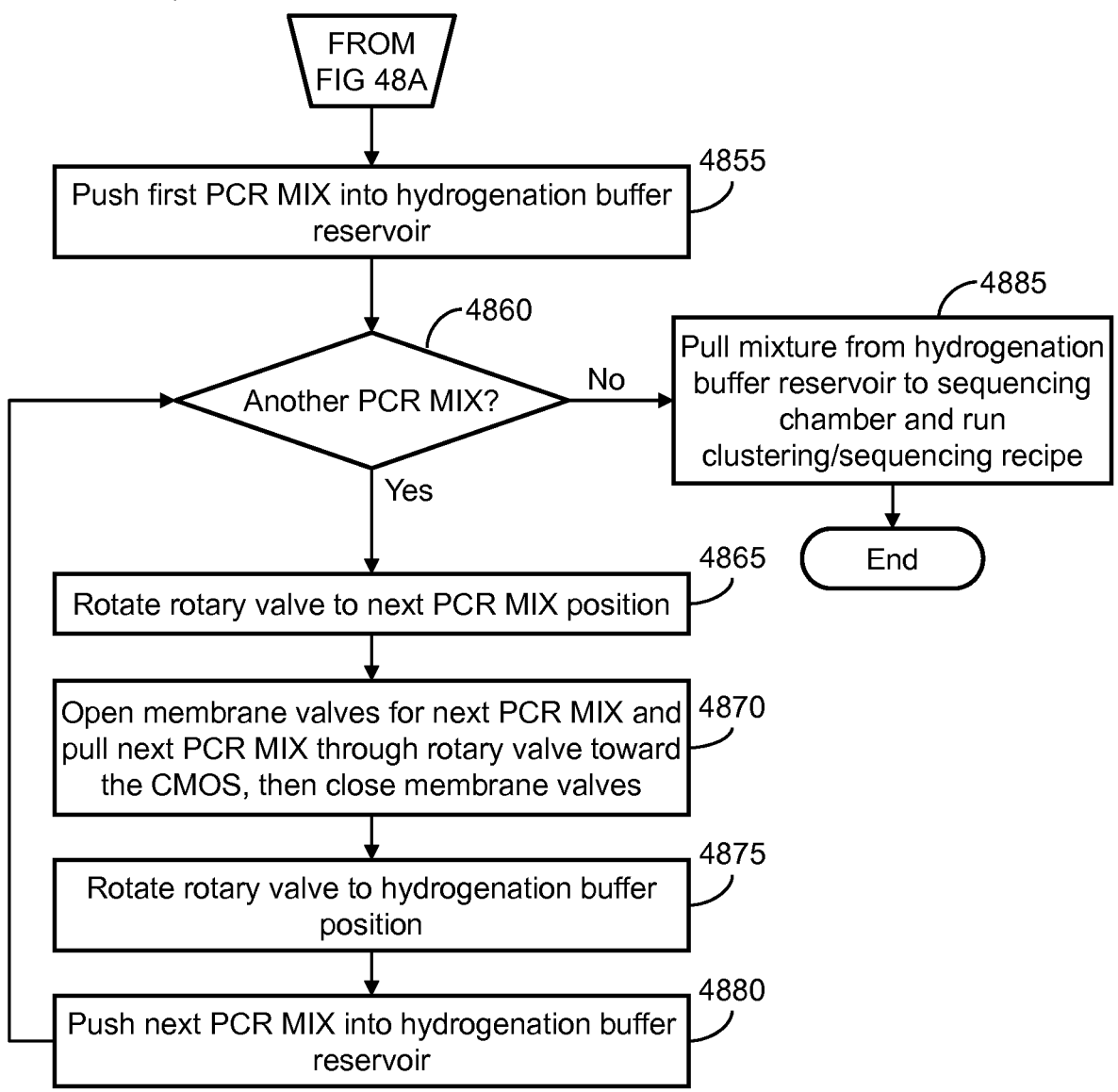

FIGS. 48A and 48B illustrate a flow diagram of an example of a method 4800 of using microfluidic cartridge assembly 1200 to perform multiplex PCR and the downstream mixing needed for sequencing. Because microfluidic cartridge assembly 1200 is based on microfluidic cartridge 1100 shown in FIG. 11, microfluidic cartridge assembly 1200 is configured for 4× sample multiplexing. Further, in method 4800 the thirteen reagent reservoirs 1216 are designated reagent reservoirs 1216a, 1216b, 1216c, 1216d, 1216e, 1216f, 1216g, 1216h, 1216i, 1216j, 1216k, 1216l, and 1216m. Further, method 4800 utilizes outlet pump 1114, which is fluidly connected to microfluidic cartridge assembly 1200. Outlet pump 1114 is positioned downstream of sequencing chamber 258. Outlet pump 1114 is capable of providing both positive pressure and negative pressure (i.e., vacuum pressure). Method 4800 includes, but is not limited to, the following steps.

At a step 4810, microfluidic cartridge assembly 1200 is provided that has been prepared for use. Namely, microfluidic cartridge assembly 1200 is provided with one or more of its reservoirs loaded with the desired liquids. For example, reagent reservoirs 1216 can be filled with the same or different reagent liquid. In one example, all of the reagent reservoirs 1216a-m are filled with hydrogenation buffer (HT1). Method 4800 proceeds to step 4815.

At a step 4815, all membrane valves are closed and then the samples/PCR MIX are loaded. "PCR MIX" means a PCR Master Mix that is optimized for use in routine PCR for amplifying DNA templates. In this step, membrane valves 242a and 244a are closed, membrane valves 242b and 244b are closed, membrane valves 242c and 244c are closed, and membrane valves 242d and 244d are closed. In this way, PCR channels 222a, 222b, 222c, and 222d are all completely sealed off. Then, a first sample liquid is mixed with a PCR MIX (hereafter called sample/PCR_MIX1) and loaded into sample loading port 1214a. A second sample liquid is mixed with a PCR MIX (hereafter called sample/PCR_MIX2) and loaded into sample loading port 1214b. A third sample liquid is mixed with a PCR MIX (hereafter called sample/PCR_MIX3) and loaded into sample loading port 1214c. A fourth sample liquid is mixed with a PCR MIX (hereafter called sample/PCR_MIX4) and loaded into sample loading port 1214d. At the completion of this step, a volume of sample/PCR MIX is sitting in each of the sample loading ports 1214 and ready for processing. Method 4800 proceeds to step 4820.

At a step 4820, the membrane valves for the first sample are opened. Then, the first sample is pulled into the PCR region. Then, the membrane valves for the first sample are closed. For example, membrane valves 242a and 244a for PCR channel 222a are opened. Then, using outlet pump 1114, sample/PCR_MIX1 is pulled into PCR channel 222a. Then, membrane valves 242a and 244a for PCR channel 222a are closed, wherein a volume of sample/PCR_MIX1 is now sealed inside of PCR channel 222a. Method 4800 proceeds to step 4825.

At a decision step 4825, it is determined whether another sample awaits to be loaded into the PCR region, i.e., into PCR region 270. If yes, then method 4800 proceeds to step 4830. If no, then method 4800 proceeds to step 4835.

At a step 4830, the membrane valves for the next sample are opened. Then, the next sample is pulled into the PCR region. Then, the membrane valves for the next sample are closed. In one example, membrane valves 242b and 244b for PCR channel 222b are opened. Then, using outlet pump 1114, sample/PCR_MIX2 is pulled into PCR channel 222b. Then, membrane valves 242b and 244b for PCR channel 222b are closed, wherein a volume of sample/PCR_MIX2 is now sealed inside of PCR channel 222b.

In another example, membrane valves 242c and 244c for PCR channel 222c are opened. Then, using outlet pump 1114, sample/PCR_MIX3 is pulled into PCR channel 222c. Then, membrane valves 242c and 244c for PCR channel 222c are closed, wherein a volume of sample/PCR_MIX3 is now sealed inside of PCR channel 222c.

In yet another example, membrane valves 242d and 244d for PCR channel 222d are opened. Then, using outlet pump 1114, sample/PCR_MIX4 is pulled into PCR channel 222d. Then, membrane valves 242d and 244d for PCR channel 222d are closed, wherein a volume of sample/PCR_MIX4 is now sealed inside of PCR channel 222d.

Method 4800 returns to step 4825.

At a step 4835, with sample/PCR_MIX1 in PCR channel 222a, sample/PCR_MIX2 in PCR channel 222b, sample/PCR_MIX3 in PCR channel 222c, and sample/PCR_MIX4 in PCR channel 222d, PCR operations are performed. Upon completion of the PCR operations, sample/PCR_MIX1 is now referred to as PCR_MIX1, sample/PCR_MIX2 is now referred to as PCR_MIX2, sample/PCR_MIX3 is now referred to as PCR_MIX3, and sample/PCR_MIX4 is now referred to as PCR_MIX4. Method 4800 proceeds to step 4840.

At a step 4840, the rotary valve is rotated to the first PRC MIX position. For example, by rotating grip portion 1240 of rotary valve assembly 1410, the position of rotary valve assembly 1410 is set to PCR channel 222a, which is holding PCR_MIX1. Method 4800 proceeds to step 4845.

At a step 4845, the membrane valves for the first PRC MIX are opened. Then, the first PCR MIX is pulled through the rotary valve toward the CMOS device. Then, the membrane valves for the first PRC MIX are closed. For example, membrane valves 242a and 244a for PCR channel 222a are opened. Then, using outlet pump 1114, PCR_MIX1 is pulled out of PCR channel 222a, into PCR output channel 224, and through rotary valve assembly 1410. Then, membrane valves 242a and 244a are closed. Method 4800 proceeds to step 4850.

At a step 4850, the rotary valve is rotated to the hydrogenation buffer (HT1) position, meaning to the reagent reservoir 1216 that is holding HT1. In method 4800, at least one reagent reservoir 1216 is holding a volume of HT1. By way of example, reagent reservoir 1216k is holding the volume of HT1. Therefore, by rotating grip portion 1240 of rotary valve assembly 1410, the position of rotary valve assembly 1410 is now set to reagent reservoir 1216k, which is holding the HT1. Method 4800 proceeds to step 4855.

At a step 4855, the first PCR MIX is pushed into the HT1 reservoir. For example, using outlet pump 1114, PCR_MIX1 is pushed through rotary valve assembly 1410 and into reagent reservoir 1216k and mixed with the HT1 therein. Method 4800 proceeds to step 4860.

At a decision step 4860, it is determined whether another PCR MIX awaits to be mixed with the HT1. If yes, then method 4800 proceeds to step 4865. If no, then method 4800 proceeds to step 4885.

At a step 4865, the rotary valve is rotated to the next PRC MIX position. In one example, by rotating grip portion 1240 of rotary valve assembly 1410, the position of rotary valve assembly 1410 is set to PCR channel 222b, which is holding PCR_MIX2. In another example, by rotating grip portion 1240 of rotary valve assembly 1410, the position of rotary valve assembly 1410 is set to PCR channel 222c, which is holding PCR_MIX3. In yet another example, by rotating grip portion 1240 of rotary valve assembly 1410, the position of rotary valve assembly 1410 is set to PCR channel 222d, which is holding PCR_MIX4. Method 4800 proceeds to step 4870.

At a step 4870, the membrane valves for the next PRC MIX are opened. Then, the next PCR MIX is pulled through the rotary valve toward the CMOS device. Then, the membrane valves for the next PRC MIX are closed. In one example, membrane valves 242b and 244b for PCR channel 222b are opened. Then, using outlet pump 1114, PCR_MIX2 is pulled out of PCR channel 222b, into PCR output channel 224, and through rotary valve assembly 1410. Then, membrane valves 242b and 244b are closed. In another example, membrane valves 242c and 244c for PCR channel 222c are opened. Then, using outlet pump 1114, PCR_MIX3 is pulled out of PCR channel 222c, into PCR output channel 224, and through rotary valve assembly 1410. Then, membrane valves 242c and 244c are closed. In yet another example, membrane valves 242d and 244d for PCR channel 222d are opened. Then, using outlet pump 1114, PCR_MIX4 is pulled out of PCR channel 222d, into PCR output channel 224, and through rotary valve assembly 1410. Then, membrane valves 242*d* and 244*d* are closed. Method 4800 proceeds to step 4875.

At a step 4875, the rotary valve is rotated to the HT1 position. For example, by rotating grip portion 1240 of rotary valve assembly 1410, the position of rotary valve assembly 1410 is returned to reagent reservoir 1216*k*, which is holding the HT1. Method 4800 proceeds to step 4880.

At a step 4880, the next PCR MIX is pushed into the HT1 reservoir. In one example, using outlet pump 1114, PCR_MIX2 is pushed through rotary valve assembly 1410 and into reagent reservoir 1216*k* and mixed with the HT1 therein. In another example, using outlet pump 1114, PCR_MIX3 is pushed through rotary valve assembly 1410 and into reagent reservoir 1216*k* and mixed with the HT1 therein. In yet another example, using outlet pump 1114, PCR_MIX4 is pushed through rotary valve assembly 1410 and into reagent reservoir 1216*k* and mixed with the HT1 therein. Method 4800 returns to step 4860.

At a step 4885, the mixture from the HT1 reservoir is pulled into the sequencing chamber and the clustering/sequencing recipe is executed. For example, with reagent reservoir 1216*k* now holding a mixture of the HT1, PCR_MIX1, PCR_MIX2, PCR_MIX3, and PCR_MIX4, this mixture is pulled out of reagent reservoir 1216*k*, then pulled along sequencing feed channel 228 and into sequencing chamber 258. Then, using CMOS image sensor 262, the clustering/sequencing recipe is executed. Method 4800 ends.

CMOS Flow Cell with Accessible Biosensor Active Area

A CMOS flow cell may be designed as a single use consumable item. Accordingly, it may be beneficial for the CMOS flow cell to be a small and inexpensive device. In a small CMOS flow cell it is important to use as much of the biosensor active area as possible. However, current CMOS flow cell designs do not allow for 100 percent utilization of the biosensor active area. Therefore, new approaches are needed to provide increased utilization of the biosensor active area in a CMOS flow cell. Various implementations of the present disclosure provides a CMOS flow cell, wherein most, or up to about 70%, 80%, 90%, 95%, 98%, 99%, or 100% of the biosensor active area is accessible for reagent delivery and illumination, as shown and described herein below with reference to FIGS. 49 through 62.

Figure 49:
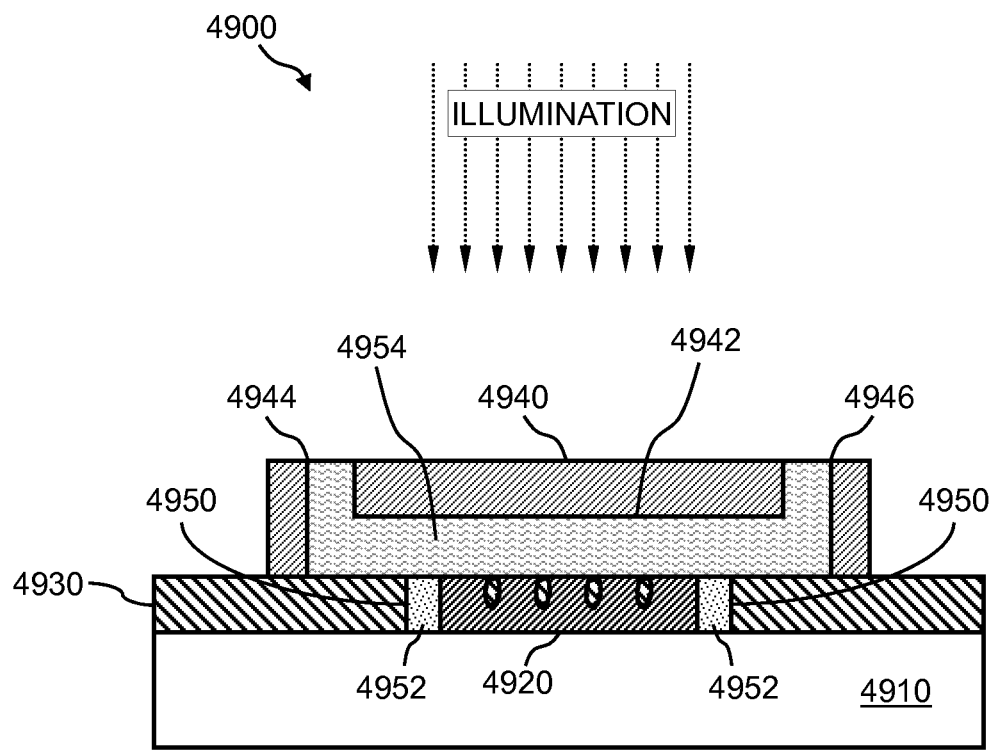
FIG. 49 illustrates a side view of an example of a CMOS flow cell, wherein up to about 100% of the biosensor active area is accessible for reagent delivery and illumination.

FIG. 49 illustrates a side view of an example of a CMOS flow cell 4900, wherein most or up to about 100% of the biosensor active area is accessible for reagent delivery and illumination. In some implementations, CCD or other image sensors may be used instead of or in addition to the CMOS sensor. CMOS flow cell 4900 includes a PCB substrate 4910, which is, for example, a flexible PCB substrate. As illustrated here, above PCB substrate 4910 is a CMOS biosensor device 4920. CMOS biosensor device 4920 is a CMOS image sensor with a biolayer thereon. Also above PCB substrate 4910 and surrounding CMOS biosensor device 4920 is a laminate film 4930. Laminate film 4930 can be formed, for example, of epoxy, polyimide or other plastic film, silicon, Kapton®, Bismaleimide-Triazine (BT) substrates, and the like. PCB substrate 4910 and laminate film 4930 can be formed using flexible PCB technology.

The purpose of laminate film 4930 is to provide an extended surface around the perimeter of CMOS biosensor device 4920 that is substantially planar with the top of CMOS biosensor device 4920. In one example, if the die thickness of CMOS biosensor device 4920 is about 100 µm, then the thickness of laminate film 4930 is about 100 µm±about 5 µm.

A slight gap between PCB substrate 4910 and laminate film 4930 forms a trench or channel 4950 around the perimeter of CMOS biosensor device 4920. The width of trench or channel 4950 can be, for example, from about 100 µm to about 1000 µm. Trench or channel 4950 is filled with filler material 4952 in order to form a substantially continuous planar surface across both CMOS biosensor device 4920 and laminate film 4930. Filler material 4952 is a material that does not interfere with the reactions that take place above CMOS biosensor device 4920. Filler material 4952 can be, for example, ultraviolet (UV)-cured epoxy, thermal-cured epoxy, or the like.

Above CMOS biosensor device 4920 and laminate film 4930 is a flow cell lid 4940 over a flow channel 4942. Further, flow cell lid 4940 includes a first port 4944 and a second port 4946 that provide inlet/outlet ports to flow channel 4942. Flow cell lid 4940 is formed of a material that is optically transparent and has low or no autoflourescence, such as, but not limited to, cyclic olefin copolymer (COC). The overall thickness of flow cell lid 4940 can be, for example, from about 300 µm to about 1000 µm. A bond area exists outside of flow channel 4942 for bonding flow cell lid 4940 to laminate film 4930. Bonding can be via a low autoflourescence adhesive.

Because a substantially continuous planar surface exists across both CMOS biosensor device 4920 and laminate film 4930, the area of flow channel 4942 within flow cell lid 4940 can be sized to span across the full CMOS biosensor device 4920; namely, it can span about 100% of the biosensor active area. In one example, if the die size of CMOS biosensor device 4920 is about 8 mm×9 mm, then the active area is about 7 mm×8 mm. However, the die size of CMOS biosensor device 4920 can range, for example, up to about 25 mm×25 mm, with a proportionately larger active area.

FIG. 49 shows, for example, a reagent fluid 4954 filling flow channel 4942. Chemical reactions take place in reagent fluid 4954 in flow channel 4942, which is atop CMOS biosensor device 4920. When illuminated through flow cell lid 4940, CMOS biosensor device 4920 is used to sense the chemical reactions that take place in flow channel 4942. Electrical connections (not shown) are provided through PCB substrate 4910 for acquiring the signals from CMOS biosensor device 4920. In CMOS flow cell 4900, about 100% of the biosensor active area of CMOS biosensor device 4920 is accessible for reagent delivery and illumination.

Figure 50:
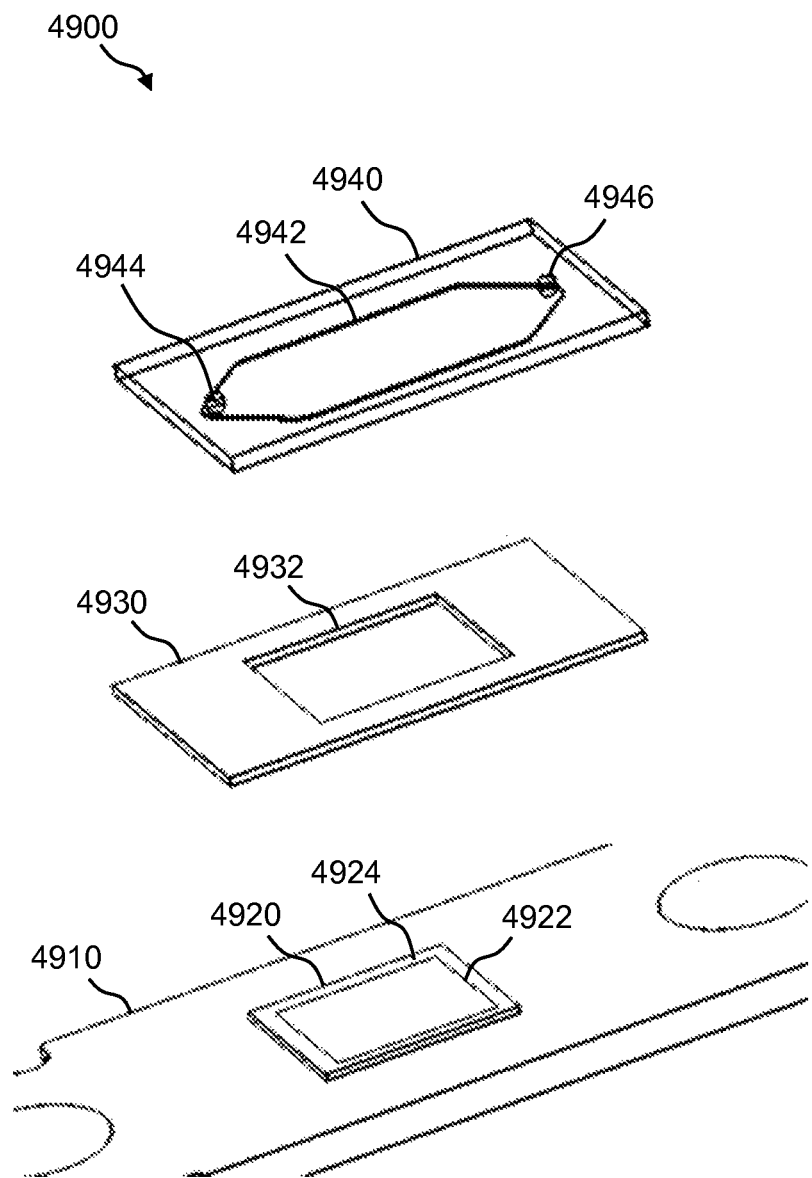
FIG. 50 illustrates an exploded view of an example of one implementation of the CMOS flow cell shown in FIG. 49.
Figure 51:
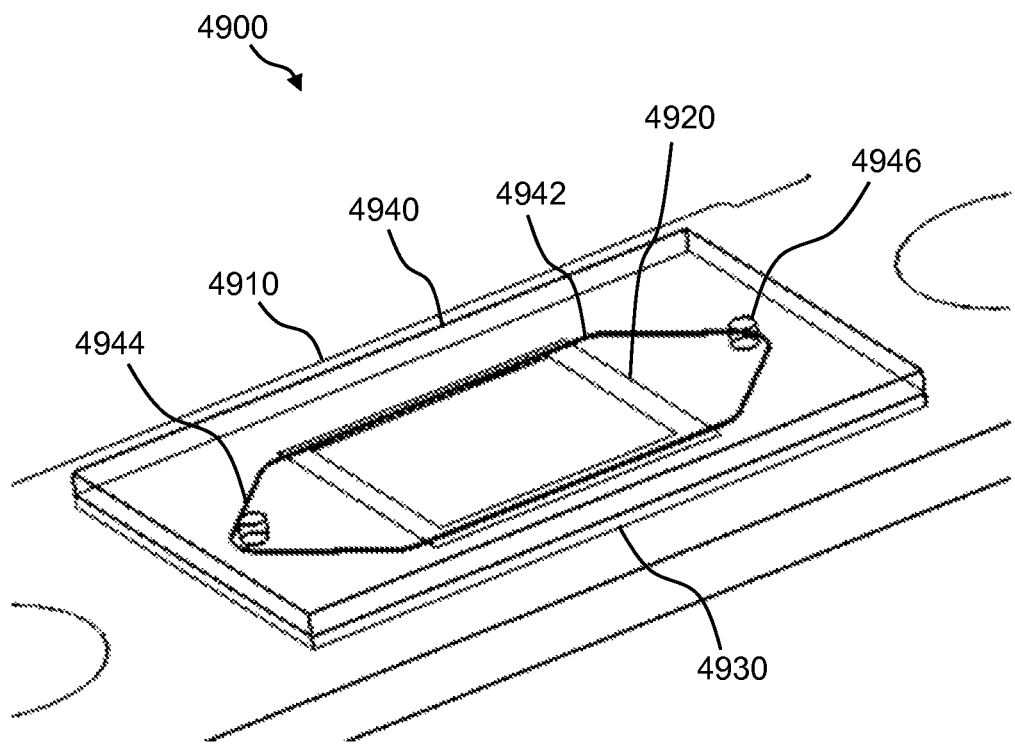
FIGS. 51 and 52 illustrate a perspective view and a side view, respectively, of the CMOS flow cell shown in FIG. 50 when fully assembled.
Figure 52:
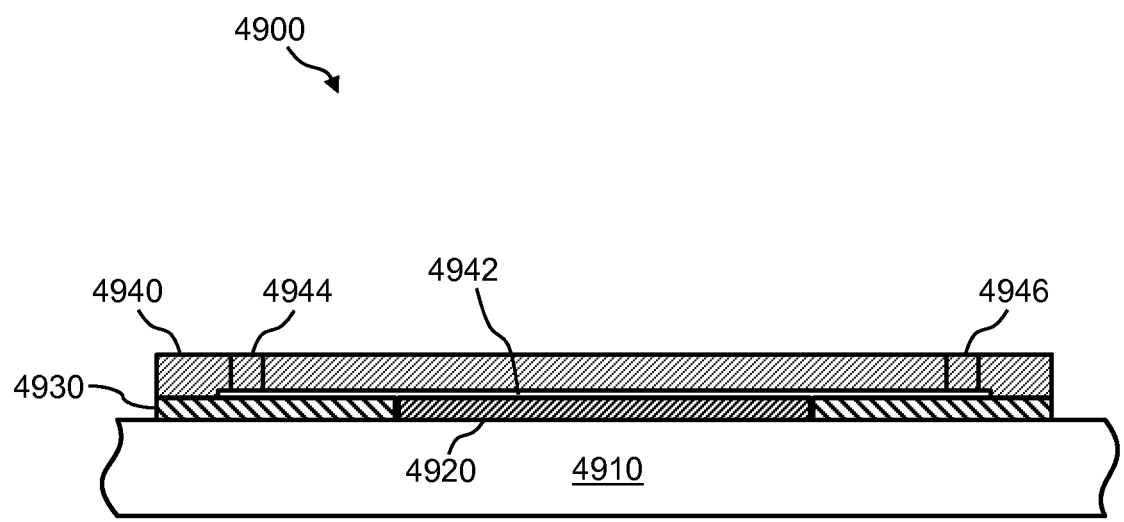

FIG. 50 illustrates an exploded view of an example of one instantiation of CMOS flow cell 4900 shown in FIG. 49. FIG. 50 shows that CMOS biosensor device 4920 includes an active area 4922. Any portion of CMOS biosensor device 4920 outside of active area 4922 is inactive area 4924. CMOS biosensor device 4920 can be attached to PCB substrate 4910 using, for example, flip-chip technology. Further, laminate film 4930 includes an opening or window 4932 that is sized for receiving CMOS biosensor device 4920 when laminated against PCB substrate 4910. Opening or window 4932 is provided in laminate film 4930 in advance of laminating laminate film 4930 to PCB substrate 4910. When flow cell lid 4940 is bonded to laminate film 4930, flow channel 4942 substantially aligns with CMOS biosensor device 4920 and its area extends beyond the area of CMOS biosensor device 4920. In FIG. 50, flow cell lid 4940 is shown as transparent. FIGS. 51 and 52 illustrate a perspective view and a side view, respectively, of CMOS flow cell 4900 shown in FIG. 50 when fully assembled.

Figure 53:
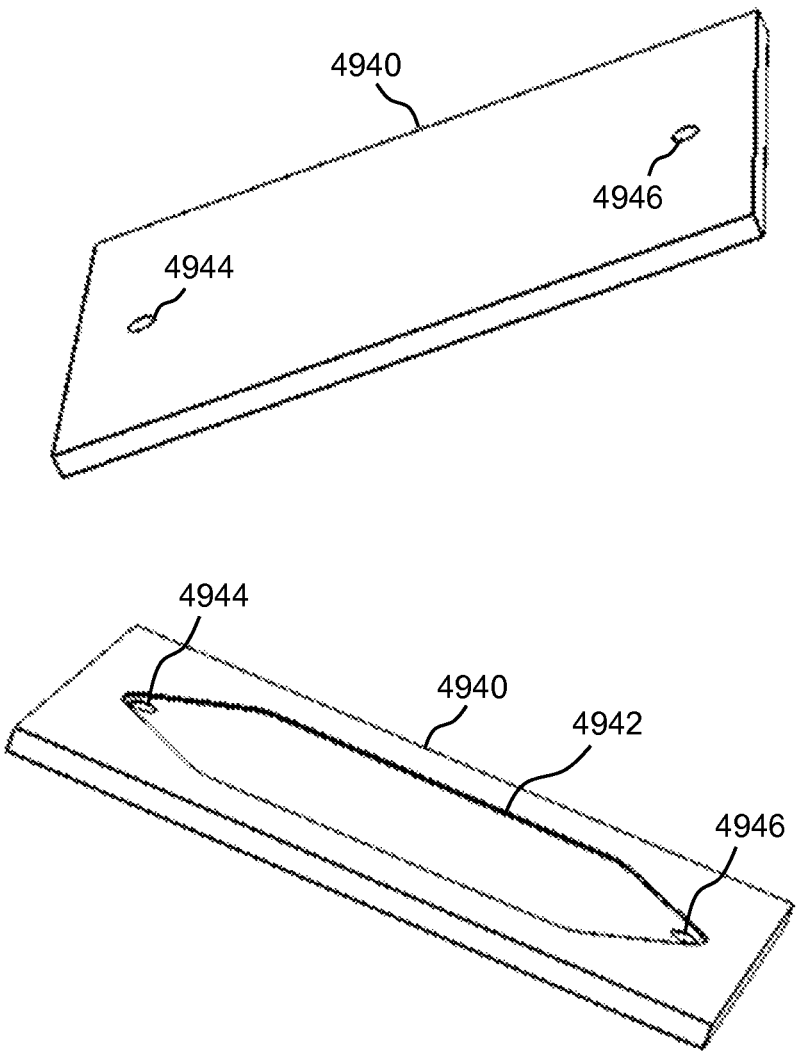
FIG. 53 illustrates perspective views of an example of the flow cell lid of the CMOS flow cell shown in FIGS. 50, 51, and 52.

FIG. 53 illustrates perspective views of an example of flow cell lid 4940 of CMOS flow cell 4900 shown in FIGS.

50, 51, and 52. Namely, FIG. 53 shows a top and bottom perspective view of flow cell lid 4940 of CMOS flow cell 4900 shown in FIGS. 50, 51, and 52. In this example, the diameter of first port 4944 and second port 4946 can be about 750 µm. Further, the depth or height of flow channel 4942 can be about 100 µm.

FIGS. 54, 55, 56, and 57 illustrate an example of a process of providing an extended planar surface in a CMOS flow cell, upon which a flow cell lid may be mounted.

Figure 54:
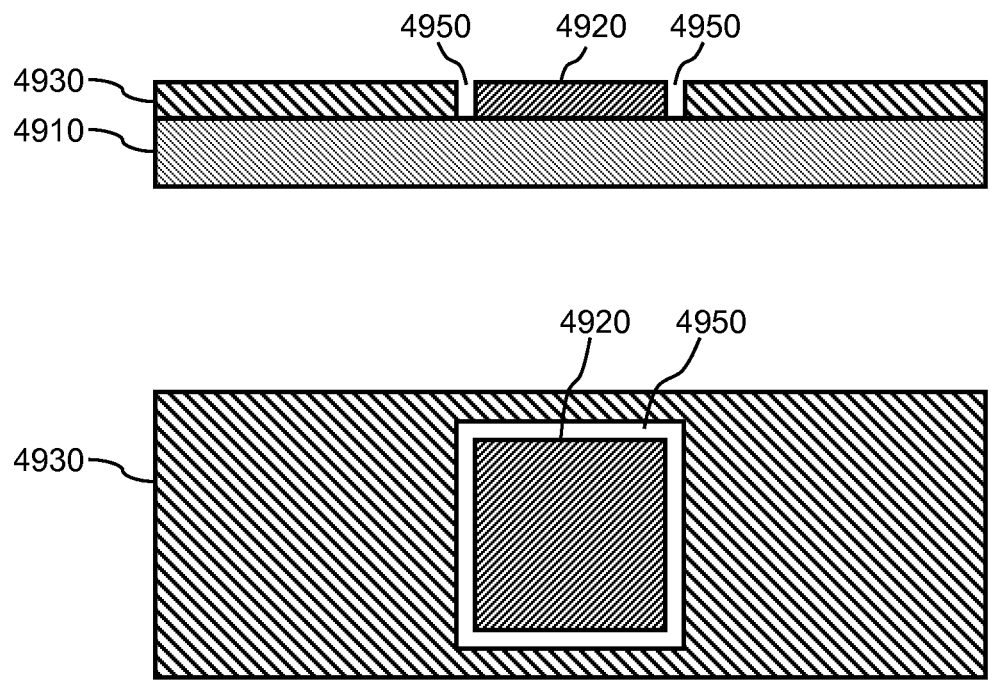
FIGS. 54, 55, 56, and 57 illustrate an example of a process of providing an extended planar surface in the CMOS flow cell, upon which the flow cell lid may be mounted.

In a first step and referring now to FIG. 54, laminate film 4930 and CMOS biosensor device 4920 are provide atop PCB substrate 4910. Trench or channel 4950 exists around the perimeter of CMOS biosensor device 4920. Trench or channel 4950 exists because opening or window 4932 in laminate film 4930 is slightly larger than CMOS biosensor device 4920.

Figure 55:
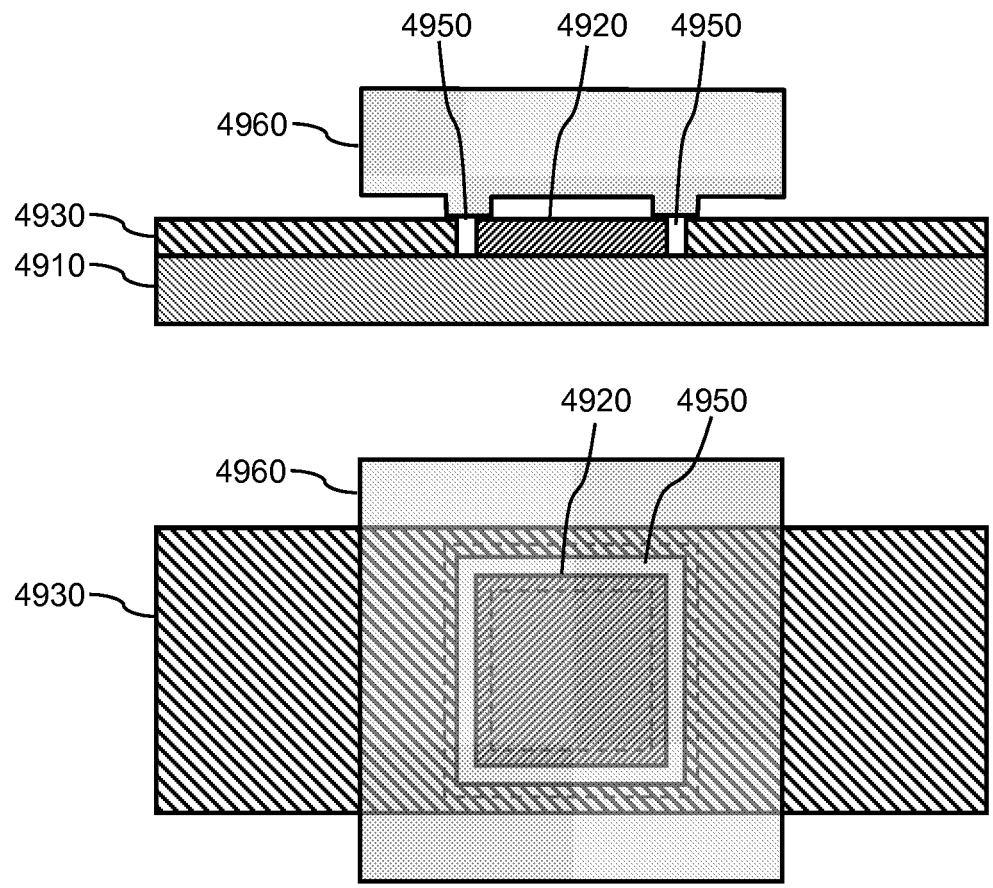

In a next step and referring now to FIG. 55, the upper side of trench or channel 4950 is sealed with, for example, an optically transparent elastomer 4960 that has features for fitting tightly against trench or channel 4950. Elastomer 4960 is optically transparent so that UV light can pass therethrough. The purpose of elastomer 4960 is to block the top of trench or channel 4950 in preparation for filling.

Figure 56:
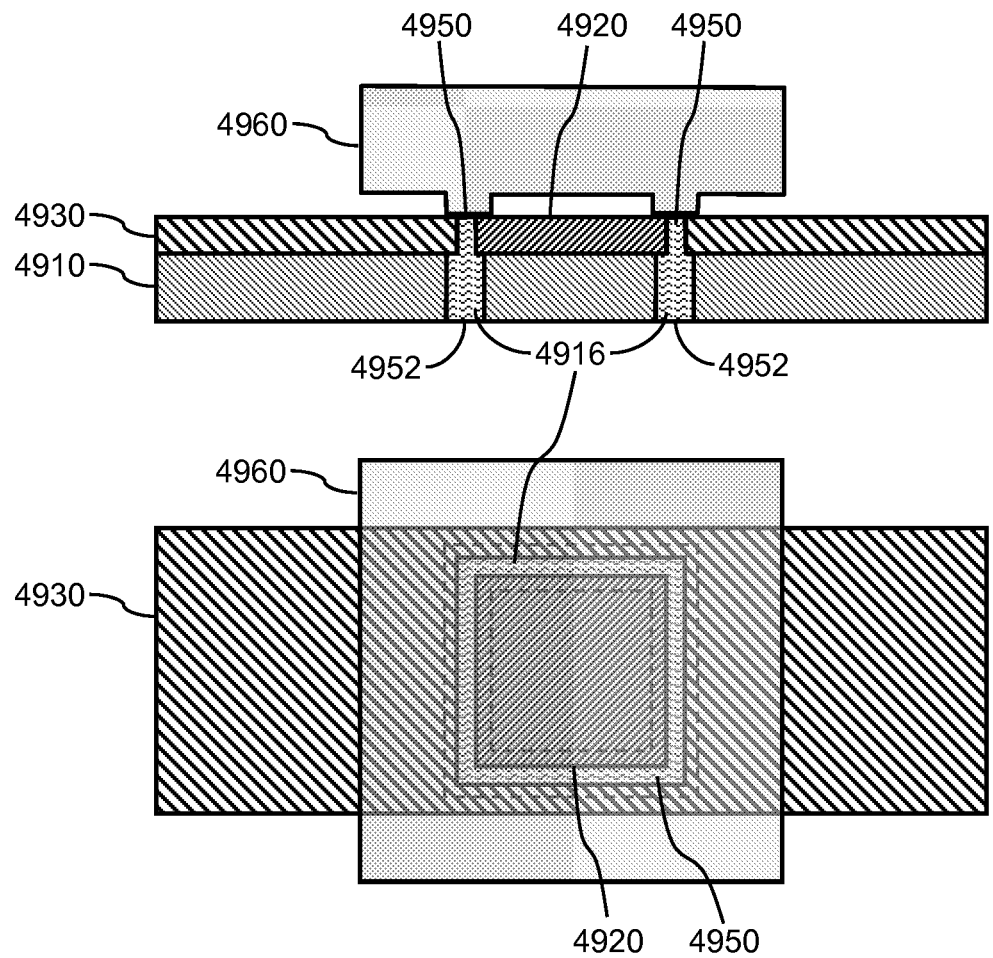

In a next step and referring now to FIG. 56, using, for example, a pair of through-holes 4916 in PCB substrate 4910, trench or channel 4950 is filled with filler material 4952, such as UV-cured epoxy, which is the reason that elastomer 4960 is optically transparent.

Figure 57:
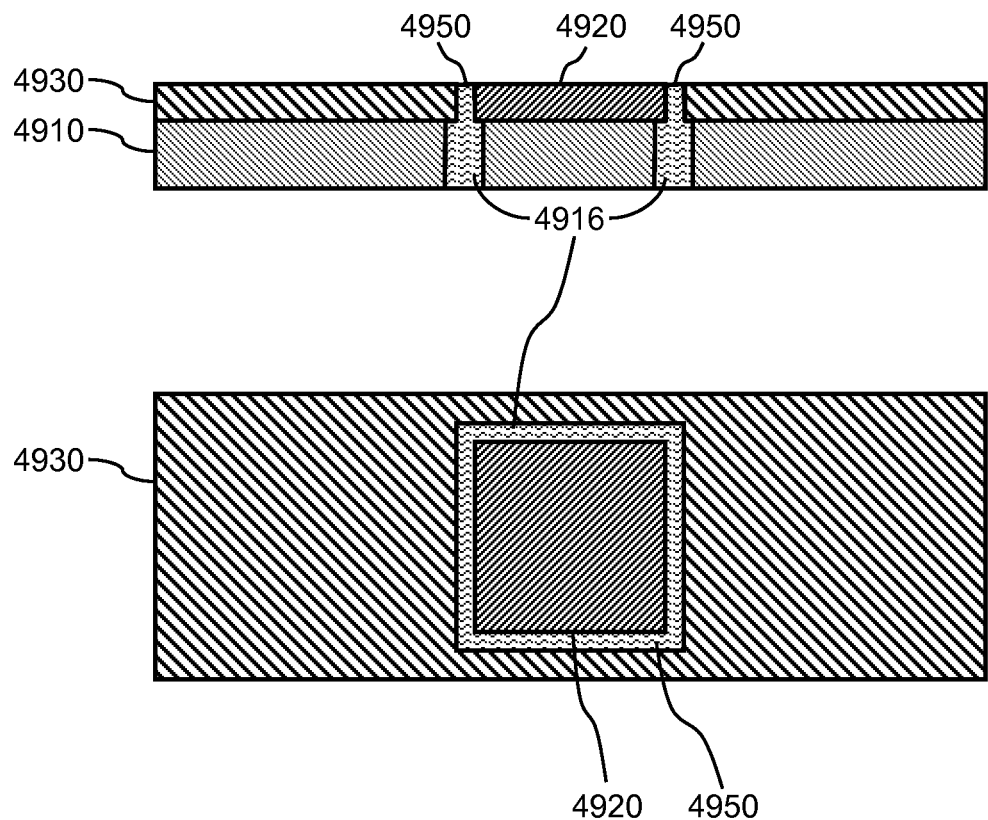

In a next step and referring now to FIG. 57, once filler material 4952 is cured, elastomer 4960 is removed and a substantially continuous planer surface is now present in the flow cell for receiving a flow cell lid, such as flow cell lid 4940.

FIGS. 58A, 58B, 58C, and 58D illustrate another example of a process of providing an extended planar surface in a CMOS flow cell, upon which a flow cell lid may be mounted.

Figure 58A:
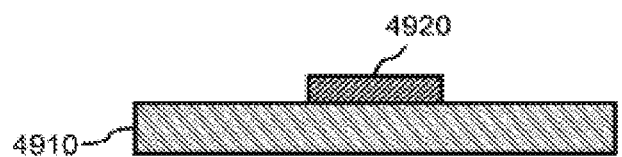
FIGS. 58A, 58B, 58C, and 58D illustrate another example of a process of providing an extended planar surface in the CMOS flow cell, upon which the flow cell lid may be mounted.

In a first step and referring now to FIG. 58A, CMOS biosensor device 4920 is provided atop PCB substrate 4910.

Figure 58B:
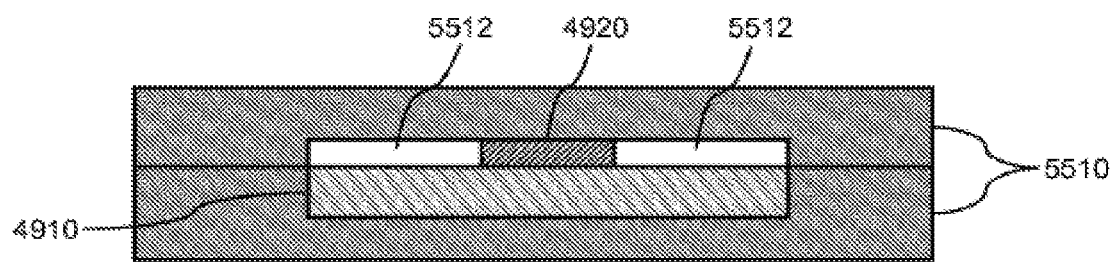

In a next step and referring now to FIG. 58B, a mold 5510 (e.g., a clamshell type mold) is provided around CMOS biosensor device 4920 and PCB substrate 4910. Mold 5510 provides a space or void 5512 atop PCB substrate 4910 and around the perimeter of CMOS biosensor device 4920.

Figure 58C:
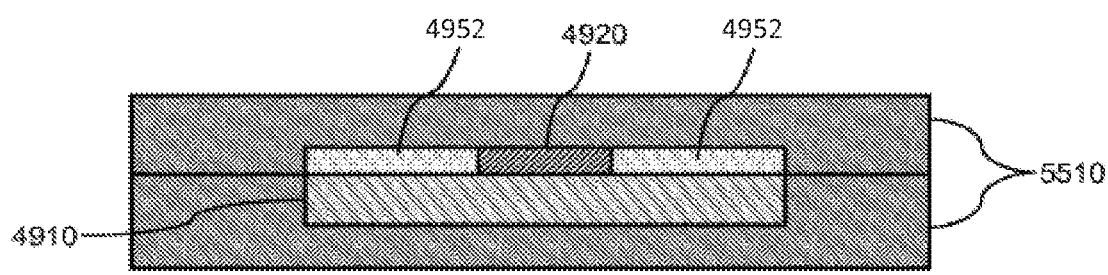

In a next step and referring now to FIG. 58C, using, for example, a low pressure injection molding process or a reaction injection molding process, space or void 5512 in mold 5510 is filled with filler material 4952, such as UV-cured or thermal-cured epoxy.

Figure 58D:
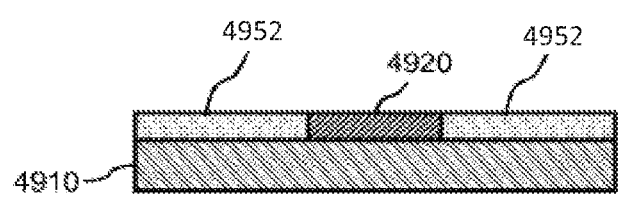

In a next step and referring now to FIG. 58D, once filler material 4952 is cured, mold 5510 is removed and a substantially continuous planer surface is now present in the flow cell for receiving a flow cell lid, such as flow cell lid 4940.

FIGS. 59, 60, 61, and 62 illustrate yet another example of a process of providing an extended planar surface in a CMOS flow cell, upon which a flow cell lid may be mounted.

Figure 59:
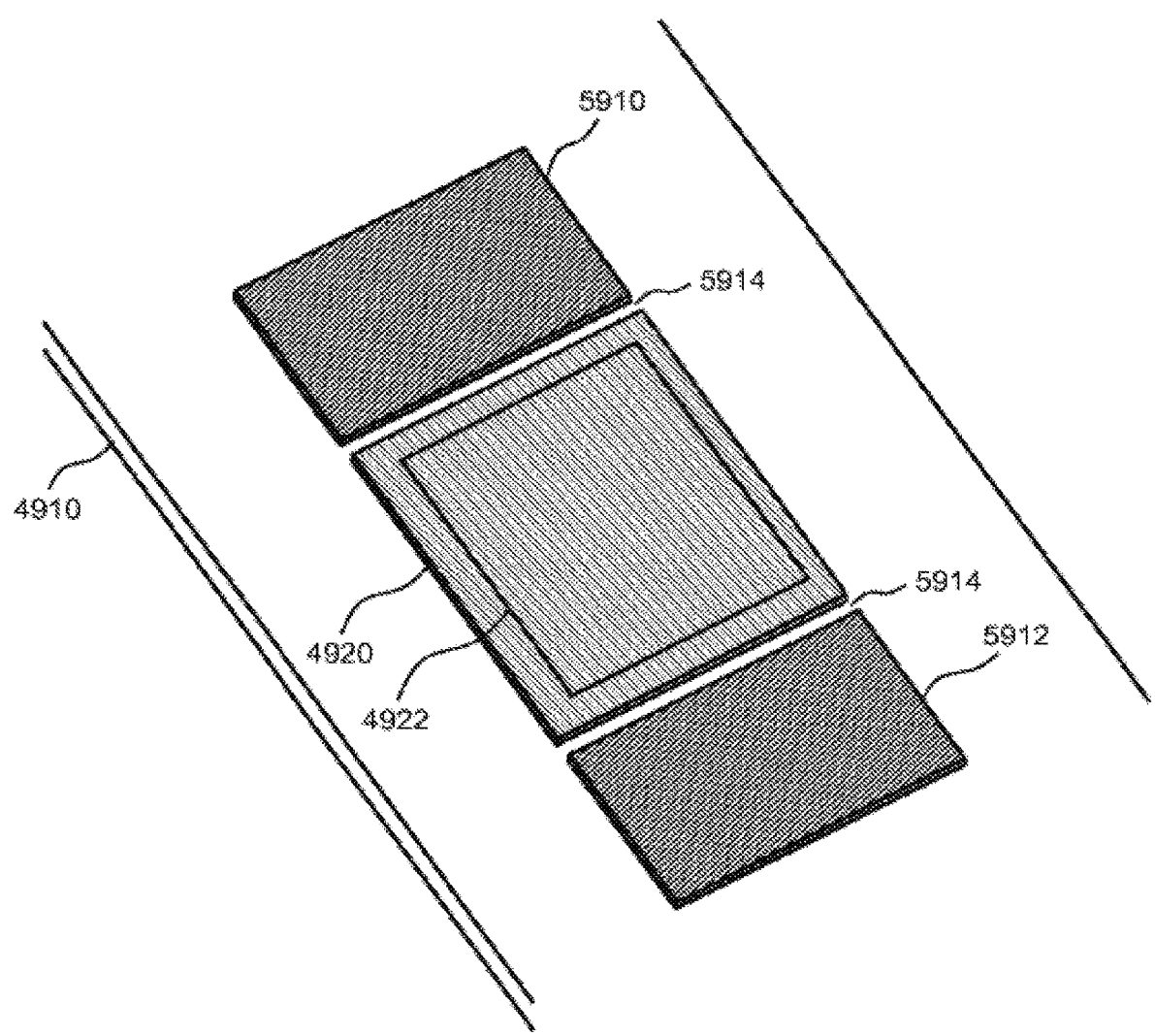
FIGS. 59, 60, 61, and 62 illustrate yet another example of a process of providing an extended planar surface in the CMOS flow cell, upon which the flow cell lid may be mounted.

In a first step and referring now to FIG. 59, CMOS biosensor device 4920 is provided atop PCB substrate 4910. Also, a mechanical material piece 5910 is provided atop PCB substrate 4910 and at one end of CMOS biosensor device 4920. Similarly, a mechanical material piece 5912 is provided atop PCB substrate 4910 and at the other end of CMOS biosensor device 4920. Mechanical material pieces 5910 and 5912 can be, for example, blank silicon, glass, or plastic. A trench or channel 5914 is between mechanical material piece 5910 and CMOS biosensor device 4920. Another trench or channel 5914 is between mechanical material piece 5912 and CMOS biosensor device 4920.

Figure 60:
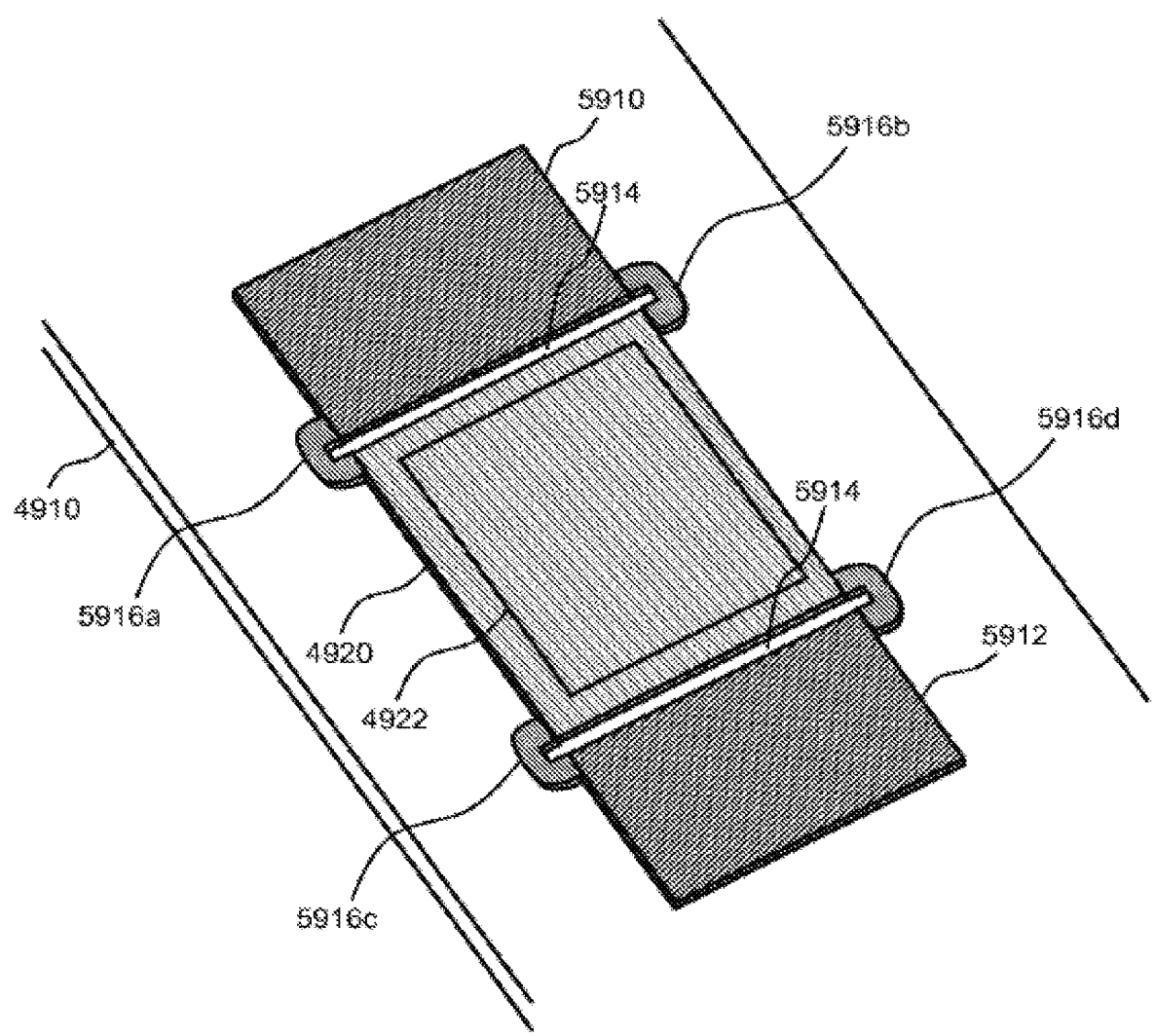

In a next step and referring now to FIG. 60, a set of barriers 5916 are provided at the ends of trenches or channels 5914. For example, barriers 5916a and 5916b are blocking the ends of one trench or channel 5914 and barriers 5916c and 5916d are blocking the ends of the other trench or channel 5914 in preparation for filling.

Figure 61:
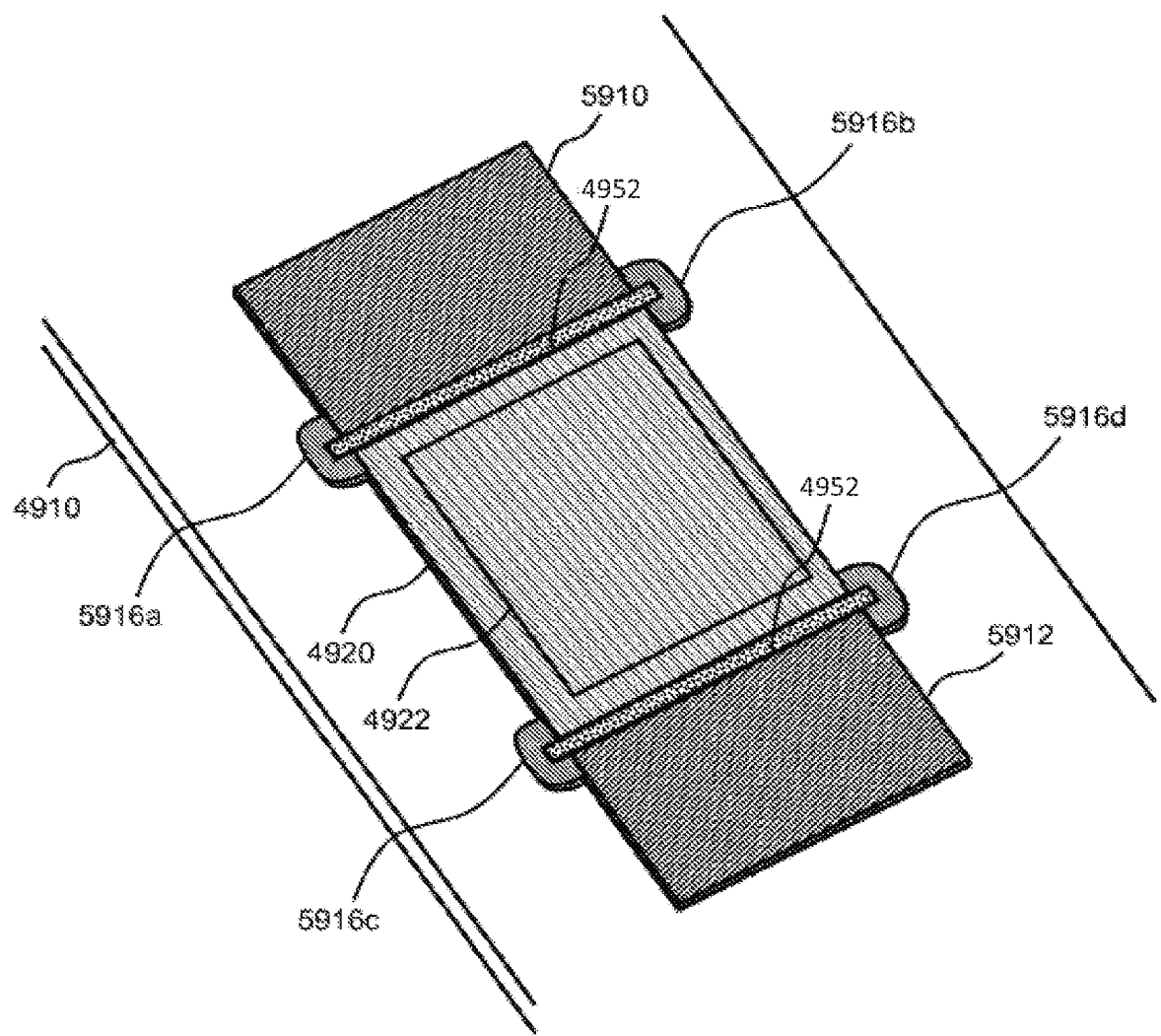

In a next step and referring now to FIG. 61, trenches or channels 5914 are filled with filler material 4952, such as UV-cured or thermal-cured epoxy. Filler material 4952 is retained between barriers 5916a and 5916b and between barriers 5916c and 5916d.

Figure 62:
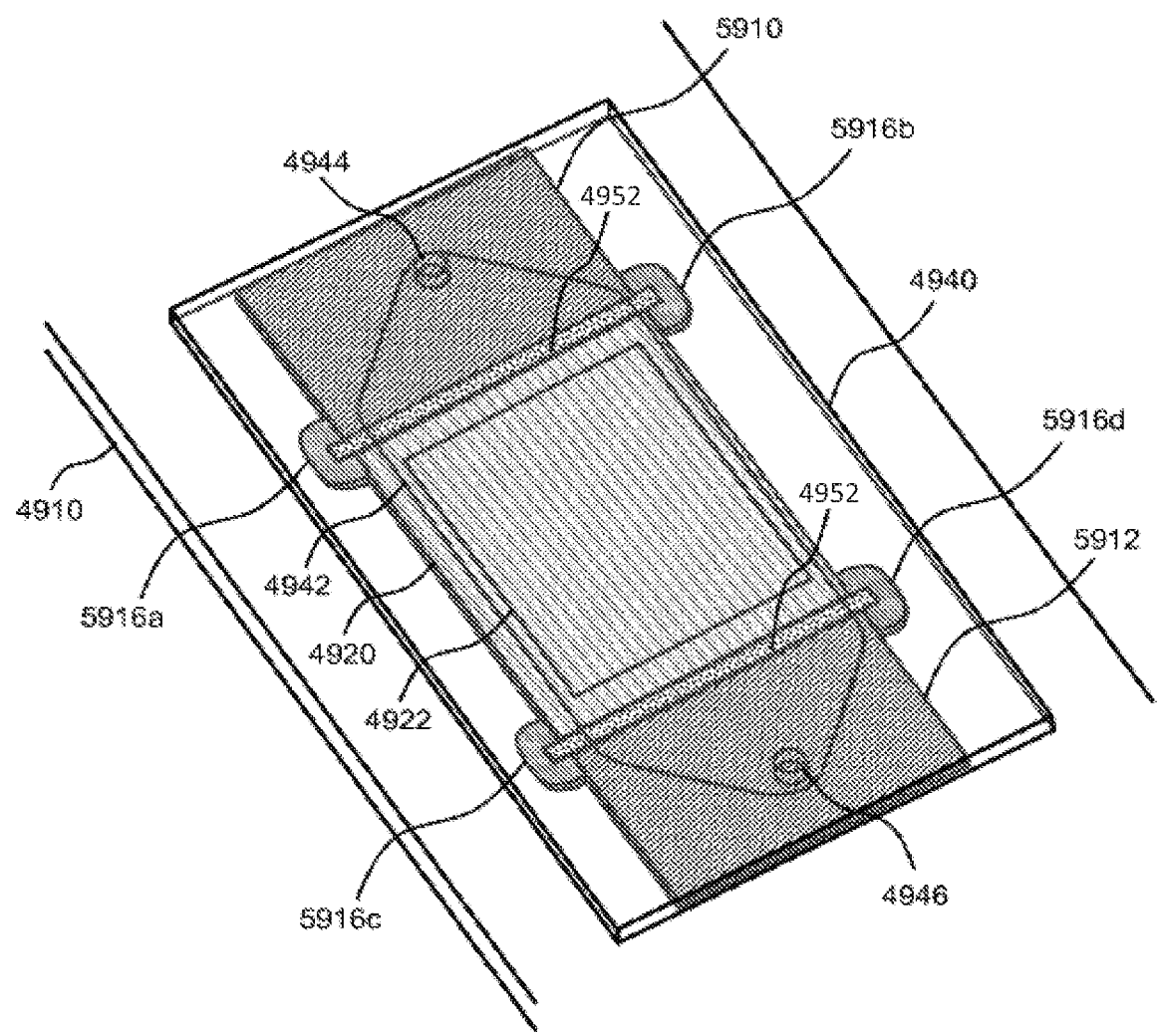

In a next step and referring now to FIG. 62, once filler material 4952 is cured, a substantially continuous planer surface is now present in the flow cell for receiving a flow cell lid, such as flow cell lid 4940.

Systems

It will be appreciated that various aspects of the present disclosure may be embodied as a method, system, computer readable medium, and/or computer program product. Aspects of the present disclosure may take the form of hardware embodiments, software embodiments (including firmware, resident software, micro-code, etc.), or embodiments combining software and hardware aspects that may all generally be referred to herein as a "circuit," "module," or "system." Furthermore, the methods of the present disclosure may take the form of a computer program product on a computer-usable storage medium having computer-usable program code embodied in the medium.

Any suitable computer useable medium may be utilized for software aspects of the present disclosure. The computer-usable or computer-readable medium may be, for example but not limited to, an electronic, magnetic, optical, electromagnetic, infrared, or semiconductor system, apparatus, device, or propagation medium. The computer readable medium may include transitory and/or non-transitory embodiments. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Program code for carrying out operations of the methods and apparatus set forth herein may be written in an object oriented programming language such as Java, Smalltalk, C++ or the like. However, the program code for carrying out operations of the methods and apparatus set forth herein may also be written in conventional procedural programming languages, such as the "C" programming language or similar programming languages. The program code may be executed by a processor, application specific integrated circuit (ASIC), or other component that executes the program code. The program code may be simply referred to as a software application that is stored in memory (such as the computer readable medium discussed above). The program code may cause the processor (or any processor-controlled device) to produce a graphical user interface ("GUI"). The graphical user interface may be visually produced on a display device, yet the graphical user interface may also have audible features. The program code, however, may operate in any processor-controlled device, such as a computer, server, personal digital assistant, phone, television, or any processor-controlled device utilizing the processor and/or a digital signal processor.

The program code may locally and/or remotely execute. The program code, for example, may be entirely or partially stored in local memory of the processor-controlled device. The program code, however, may also be at least partially remotely stored, accessed, and downloaded to the processor-controlled device. A user's computer, for example, may entirely execute the program code or only partly execute the program code. The program code may be a stand-alone software package that is at least partly on the user's computer and/or partly executed on a remote computer or entirely on a remote computer or server. In the latter scenario, the remote computer may be connected to the user's computer through a communications network.

The methods and apparatus set forth herein may be applied regardless of networking environment. The communications network may be a cable network operating in the radio-frequency domain and/or the Internet Protocol (IP) domain. The communications network, however, may also include a distributed computing network, such as the Internet (sometimes alternatively known as the "World Wide Web"), an intranet, a local-area network (LAN), and/or a wide-area network (WAN). The communications network may include coaxial cables, copper wires, fiber optic lines, and/or hybrid-coaxial lines. The communications network may even include wireless portions utilizing any portion of the electromagnetic spectrum and any signaling standard (such as the IEEE 802 family of standards, GSM/CDMA/TDMA or any cellular standard, and/or the ISM band). The communications network may even include powerline portions, in which signals are communicated via electrical wiring. The methods and apparatus set forth herein may be applied to any wireless/wireline communications network, regardless of physical componentry, physical configuration, or communications standard(s).

Certain aspects of present disclosure are described with reference to various methods and method steps. It will be understood that each method step can be implemented by the program code and/or by machine instructions. The program code and/or the machine instructions may create means for implementing the functions/acts specified in the methods.

The program code may also be stored in a computer-readable memory that can direct the processor, computer, or other programmable data processing apparatus to function in a particular manner, such that the program code stored in the computer-readable memory produce or transform an article of manufacture including instruction means which implement various aspects of the method steps.

The program code may also be loaded onto a computer or other programmable data processing apparatus to cause a series of operational steps to be performed to produce a processor/computer implemented process such that the program code provides steps for implementing various functions/acts specified in the methods of the present disclosure.

What is claimed is:

1. A microfluidic cartridge for detecting biological reactions, comprising:
(a) a flow cell including a reaction site area encompassing one or more reaction sites; (b) fluidics channels for delivering reactants to and/or removing reactants from the reaction site area; and (c) an image sensor having an active area configured to detect signals of biological reactions in the reaction site area,
wherein:
the reaction site area is proximal to the active area of the image sensor;
the reaction site area spans substantially all of the active area of the image sensor;
the fluidics channels do not substantially overlap with the active area of the image sensor; the flow cell comprises a sequencing chamber; the sequencing chamber is formed on a sequencing chamber layer; the image sensor is disposed in an opening of a sequencing chamber bottom layer under the sequencing chamber layer; and the fluidics channels are formed on a fluidics channels layer under the sequencing chamber bottom layer.

2. The microfluidic cartridge of claim 1, wherein
the microfluidic cartridge is configured to perform sequencing operations on a nucleic acid sample, and
the detected signals of biological reactions are indicative of nucleotide base types involved in the biological reactions.

3. The microfluidic cartridge of claim 2, wherein the flow cell comprises a substrate of hydrophilic regions for nucleic acid attachment and amplification surrounded by hydrophobic regions.

4. The microfluidic cartridge of claim 1, wherein the reaction site area spans all of the active area of the image sensor.

5. The microfluidic cartridge of claim 1, wherein the fluidics channels do not overlap with the active area of the image sensor.

6. The microfluidic cartridge of claim 1, wherein the image sensor comprises a photo detector.

7. The microfluidic cartridge of claim 6, wherein the photo detector comprises a CMOS/CCD sensor.

8. The microfluidic cartridge of claim 7, wherein the CMOS sensor is about 9200 µm long, about 8000 µm wide, and about 800-1000 µm thick.

9. The microfluidic cartridge of claim 1, further comprising: a PCR region, a reagent mixing and distributing region, and one or more membrane valves that are configured to reversibly stop the PCR region from fluidic communication with the reagent mixing and distribution region or the flow cell including the reaction site area.

10. The microfluidic cartridge of claim 9, wherein the PCR region comprises a plurality of PCR channels.

11. The microfluidic cartridge of claim 9, wherein the reagent mixing and distributing region comprises a plurality of reagent channels and/or reagent supplies.

12. The microfluidic cartridge of claim 9, further comprising a rotary valve that is configured to fluidly connect the PCR region to the reagent mixing and distributing region.

13. The microfluidic cartridge of claim 12, wherein the rotary valve is further configured to fluidly connect the reagent mixing and distributing region to the flow cell including a reaction site area.

* * * * *